US008993287B2

(12) United States Patent
Preston

(10) Patent No.: US 8,993,287 B2
(45) Date of Patent: Mar. 31, 2015

(54) BIOCATALYSTS AND METHODS FOR CONVERSION OF HEMICELLULOSE HYDROLYSATES TO BIOBASED PRODUCTS

(75) Inventor: James F. Preston, Micanopy, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 514 days.

(21) Appl. No.: 13/122,985

(22) PCT Filed: Nov. 17, 2009

(86) PCT No.: PCT/US2009/064773
§ 371 (c)(1),
(2), (4) Date: Apr. 7, 2011

(87) PCT Pub. No.: WO2010/059616
PCT Pub. Date: May 27, 2010

(65) Prior Publication Data
US 2011/0195464 A1   Aug. 11, 2011

Related U.S. Application Data

(60) Provisional application No. 61/115,722, filed on Nov. 18, 2008, provisional application No. 61/229,536, filed on Jul. 29, 2009.

(51) Int. Cl.
| | |
|---|---|
| *C12N 1/21* | (2006.01) |
| *C12P 7/54* | (2006.01) |
| *C12P 7/04* | (2006.01) |
| *C12P 7/10* | (2006.01) |
| *C12P 7/18* | (2006.01) |
| *C12P 7/40* | (2006.01) |
| *C12P 7/46* | (2006.01) |
| *C12P 7/56* | (2006.01) |
| *C12R 1/01* | (2006.01) |

(52) U.S. Cl.
CPC ... *C12P 7/54* (2013.01); *C12P 7/04* (2013.01); *C12P 7/10* (2013.01); *C12P 7/18* (2013.01); *C12P 7/40* (2013.01); *C12P 7/46* (2013.01); *C12P 7/56* (2013.01); *C12R 1/01* (2013.01); *Y02E 50/16* (2013.01); *Y02E 50/17* (2013.01)
USPC ............ 435/165; 435/161; 435/267; 435/252

(58) Field of Classification Search
None
See application file for complete search history.

(56) References Cited

U.S. PATENT DOCUMENTS

| 5,000,000 A | 3/1991 | Ingram et al. |
| 7,098,009 B2 | 8/2006 | Shanmugam et al. |
| 7,629,162 B2 | 12/2009 | Zhou et al. |
| 2007/0072280 A1 | 3/2007 | Cirino et al. |
| 2009/0148914 A1 | 6/2009 | Causey et al. |

FOREIGN PATENT DOCUMENTS

| WO | WO 2008/115958 | 9/2008 |
| WO | WO 2008/119009 | 10/2008 |

OTHER PUBLICATIONS

B.S. Dien et al. "Bacteria engineered for fuel ethanol production: current status", Allied Microbiology and Biotechnology 63:258-266 (2003).*
Bi, C. et al. "Genetic engineering of *Enterobacter asburiae* strain JDR-1 for efficient production of ethanol from hemicelluloses hydrolysate" *Applied and Environmental Microbiology*, Sep. 2009, pp. 5743-5749, vol. 75, No. 18.
Bi, C. et al. "Complete Fermentation of Xylose and Methylglucuronoxylose Derived from Methylglucuronoxylan by *Enterobacter asburiae* Strain JDR-1" *Applied and Environmental Microbiology*, Jan. 2009, pp. 395-404, vol. 75, No. 2.
Brenner, D. J. et al. "*Enterobacter asburiae* sp. nov., a New Species Found in Clinical Specimens, and Reassignment of *Erwinia dissolvens* and *Erwinia nimipressuralis* to the Genus *Enterobacter* as *Enterobacter dissolvens* comb. nov. and *Enterobacter nimipressuralis* comb. nov." *Journal of Clinical Microbiology*, Jun. 1986, pp. 1114-1120, vol. 23, No. 6.
Shin, J. H. et al. "In situ production of biohydrogen for fuel cell" *Annual Proceedings of the Korean Society for New and Renewable Energy*, Jun. 2006, pp. 470-473.
Debeire, P. et al. "Purification and properties of an endo-1,4-xylanase excreted by a hydrolytic thermophilic anaerobe, *Clostridium thermolacticum*" *European Journal of Biochemistry*, 1990, pp. 573-580, vol. 187.
Hurlbert, J. C. et al. "Functional Characterization of a Novel Xylanase from a Corn Strain of *Erwinia chrysanthemi*" *Journal of Bacteriology*, Mar. 2001, pp. 2093-2100, vol. 183, No. 6.
Bi, C. et al. "Genetic engineering of *Enterobacter asburiae* strain JDR-1 for efficient D(-) lactic acid production from hemicelluloses hydrolysate" *Biotechnology Letters*, 2009, pp. 1551-1557, vol. 31.
St John, F. et al. "*Paenibacillus* sp. Strain JDR-2 and XynA1: a Novel System for Methylglucuronoxylan Utilization" *Applied and Environmental Microbiology*, Feb. 2006, pp. 1496-1506, vol. 72, No. 2.
Zhou, S. et al. "Gene Integration and Expression and Extracellular Secretion of *Erwinia chrysanthemi* Endoglucanase CelY (celY) and CelZ (celZ) in Ethanologenic *Klebsiella oxytoca* P2" *Applied and Environmental Microbiology*, Jan. 2001, pp. 6-14, vol. 67, No. 1.
Moniruzzaman, M. et al. "Isolation and Molecular Characterization of High-Performance Cellobiose-Fermenting Spontaneous Mutants of Ethanologenic *Escherichia coli* KO11 Containing the *Klebsiella oxytoca* casAB Operon" *Applied and Environmental Microbiology*, Dec. 1997, pp. 4633-4637, vol. 63, No. 12.

(Continued)

*Primary Examiner* — Rebecca Prouty
(74) *Attorney, Agent, or Firm* — Saliwanchik, Lloyd & Eisenschenk

(57) ABSTRACT

The invention relates to processes and biocatalysts for producing ethanol and other useful products from biomass and/or other materials. Initial processing of lignocellulosic biomass frequently yields methylglucuronoxylose (MeGAX) and related products which are resistant to further processing by common biocatalysts. Strains of *Enterobacter asburiae* are shown to be useful in bioprocessing of MeGAX and other materials into useful bioproducts such as ethanol, acetate, lactate, and many others. Genetic engineering may be used to enhance production of desired bioproducts.

11 Claims, 13 Drawing Sheets

(56) References Cited

OTHER PUBLICATIONS

Written Opinion in International Application No. PCT/US2009/064773, May 11, 2010, pp. 1-5.

Database Genbank, Accession No. EU719655, Bi, C., "Genetic Engineering Enterobacter asburiae strain JDR-1 for efficient ethanol production from hemicellulose hydrolysate" Jun. 11, 2008, p. 1.

* cited by examiner

US 8,993,287 B2

BIOCATALYSTS AND METHODS FOR CONVERSION OF HEMICELLULOSE HYDROLYSATES TO BIOBASED PRODUCTS

CROSS-REFERENCE TO RELATED APPLICATIONS

This application is the U.S. national stage application of International Patent Application No. PCT/US2009/064773, filed Nov. 17, 2009, which claims the benefit of U.S. Provisional Patent Application Nos. 61/115,722, filed Nov. 18, 2008 and Ser. No. 61/229,536, filed Jul. 7, 2009, the disclosures of which are hereby incorporated by reference in their entireties, including all figures, tables and amino acid or nucleic acid sequences.

GOVERNMENT SUPPORT

This invention was made with government support under grants awarded as follows: Department of Energy grant numbers USDOE G012026-161, DE FC36-990010476, and DE FC36-00GO10594. The government has certain rights in this invention.

BACKGROUND OF THE INVENTION

The need for alternatives to petroleum resources for production of fuels and chemicals has become a major quest, generated from economic incentives associated with limited and diminishing supply (Kheshgi, H. S., R. C. Prince, and G. Marland. 2000. The potential of biomass fuels in the context of global climate change: focus on transportation fuels. *Annu. Rev. Energy Environ.* 25:199-244). The connection between increasing carbon dioxide and global warming has directed this quest toward formation of fermentation products derived from resources renewable through photosynthesis (McMillan J. D. (1997) Bioethanol production: status and prospects. Renew Energy 10:295-302). The development of yeast and bacterial biocatalysts has been applied to the commercial production of ethanol as an alternative fuel from starch and sucrose derived from commodity crops, e.g. corn and sugarcane (Dien, B. S., M. A. Cotta, and T. W. Jeffries. 2003. Bacteria engineered for fuel ethanol production: current status. Appl Microbiol Biotechnol 63:258-266). To expand production of ethanol and chemical feedstocks from renewable resources that do not economically impact these commodities, lignocellulosic resources, including forest and agricultural residues, have become targets for bioconversion cellulose and hemicellulose to fermentable sugars (Aden, A., M. Ruth, K. Ibsen, J. Jechura, K. Neeves, J. Sheehan, B. Wallace, L. Montague, A. Slayton, and J. Lukas. 2002. Lignocellulosic biomass to ethanol process design and economics utilizing co-current dilute acid prehydrolysis and enzymatic hydrolysis for corn stover. NREL/TP-510-32438. National Renewable Energy Laboratory, Golden, Colo. Available online at nrel.gov/docs/fy02osti/32438.pdf.

Cellulose comprises the major part of all plant biomass. The source of all cellulose is the structural tissue of plants. It occurs in close association with hemicellulose and lignin, which together comprise the major components of plant fiber cells. Cellulose consists of long chains of beta glucosidic residues linked through the 1,4 positions. These linkages cause the cellulose to have a high crystallinity and thus a low accessibility to enzymes or acid catalysts. Hemicellulose is an amorphous hetero-polymer which is easily hydrolyzed. Lignin, an aromatic three-dimensional polymer, is interspersed among the cellulose and hemicellulose within the plant fiber cell.

Previously reported processes for hydrolysing cellulose include biological and non-biological means of depolymerization. The biological methods involve the use a cellulase enzyme. The oldest and best known non-biological method of producing sugars from cellulose is the use of acid hydrolysis. The acid most commonly used in this process is sulfuric acid. In general, sulfuric acid hydrolysis can be categorized as either dilute acid hydrolysis or concentrated acid hydrolysis.

The dilute acid processes generally involve the use of 0.5% to 15% sulfuric acid to hydrolyze the cellulosic material. In addition, temperatures ranging from 90°-600° C., and pressure up to 800 psi are necessary to effect the hydrolysis. At high temperatures, the sugars degrade to form furfural and other undesirable by-products. The resulting glucose yields are generally low, less than 50%. Accordingly, the dilute acid processes have not been successful in obtaining sugars from cellulosic material in high yields at low cost.

In addition to these difficulties, it has been recognized that the fermentation of the sugars produced by dilute acid hydrolysis presents additional problems. The hydrolysis of cellulose and hemicellulose results in the production of pentose sugars for fermentation (Y. Y. Lee A1, Prashant Iyer, R. W. Torget. 1999. Dilute-Acid Hydrolysis of Lignocellulosic Biomass. Advances in Biochemical Engineering/Biotechnology Volume 65 pp. 93-115). The predominant structural polymer in the hemicellulose fraction of hardwoods and crop residues is methylglucuronoxylan (MeGAX$_n$), a β-1,4 linked xylan in which xylose residues are periodically substituted with a-1,2-linked 4-O-methyl-glucuronic acid (Preston, J. F., J. C. Hurlbert, J. D. Rice, A. Ragunathan, and F. J. St. John. 2003. Microbial strategies for the depolymerization of glucuronoxylan: leads to biotechnological applications of endoxylanases, p. 191-210, Applications of Enzymes to Lignocellulosics. American Chemical Society, Washington D.C.). Resistance of the a-1,2 glucuronosyl linkages to dilute acid hydrolysis results in the release of methylglucuronoxylose (MeGAX), which is not fermented by bacterial biocatalysts currently used to convert hemicellulose to ethanol, e.g. *E. coli* KO11. The frequency of MeGAX substitutions on the xylose residues of methylglucuronoxylan ranges from less than one in ten in crop residues to one in six to seven in hardwoods, e.g. sweetgum, and as much as 21% of the carbohydrate may reside in this unfermentable fraction following dilute acid pretreatment (Maria E. Rodriguez, Alfredo Martinez, Lonnie Ingram, Keelnatham T Shamugam and James F Preston. 2001. Properties of the hemicellulose fractions of lignocellulosic biomass affecting bacterial ethanol production. ASM National Meeting, 2001.). As a result of the sometimes large yield of MeGAX following dilute acid processes, the sugar yield is low and fermentation is hampered in producing useful biofuels and chemical feedstocks from renewable photosynthetic resources.

Thus, there is an urgent need for an economically viable, environmentally safe microorganism that can ferment MeGAX resulting from dilute acid hydrolysis of photosynthetic resources to produce useful biofuels (such as ethanol) and chemical feedstocks (such as acetate).

BRIEF SUMMARY OF THE INVENTION

The invention relates to processes and biocatalysts for producing ethanol and other useful products from biomass and/or other materials. Initial processing of lignocellulosic biomass frequently yields methylglucuronoxylose (MeGAX) and related products which are resistant to further processing by common biocatalysts. Strains of *Enterobacter asburiae* are shown to be useful in bioprocessing of MeGAX and other materials into useful bioproducts such as ethanol, acetate, lactate, and many others. Genetic engineering may be used to enhance production of desired bioproducts.

BRIEF DESCRIPTION OF THE FIGURES

FIG. 5A depicts *E. asburiae* JDR-1 in minimal medium; FIG. 5B depicts *E. asburiae* L1 in minimal medium; FIG. 5C depicts *E. asburiae* JDR-1 in LB; FIG. 5D depicts *E. asburiae* L1 in LB. Substrates and fermentation products: xylose (closed diamonds ♦), MeGAX (closed squares ■), acetic acid (open triangles △), ethanol (open squares □), lactic acid (open diamonds ◇).

FIG. 8A depicts *E. asburiae* JDR-1; FIG. 8B depicts *E. coli* KO11; FIG. 8C depicts *E. asburiae* JDR-1 (pLO1555); and FIG. 8D depicts *E. asburiae* E1 (pLO1555). Substrates and fermentation products: xylose (closed diamonds ♦), MeGAX (closed squares ■), acetic acid (open triangles △), formic acid (open circles ○), ethanol (open squares □).

DETAILED DESCRIPTION OF THE INVENTION

Figure 1:
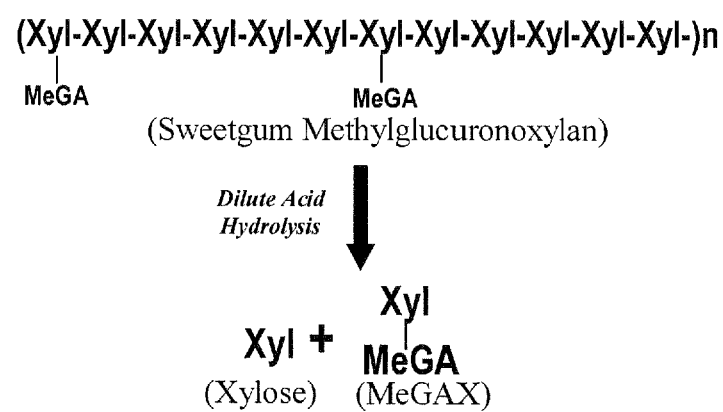
FIG. 1: Scheme for the release of xylose and MeGAX by dilute acid hydrolysis of sweetgum xylan.

The present invention provides novel microorganisms that are capable of fermenting by-products of acid hydrolysis of renewable biomass materials. According to the invention, the fermentation of MeGAX sugars produced from acid hydrolysis of biomass materials involves the use of bacteria, namely *Enterobacter asburiae*. Because MeGAX is not fermented by bacterial biocatalysts currently used to convert biomass materials into useful bioproducts, the presence of MeGAX retards the overall production rate and yield in a fermentation process.

There exist commercially available industrial microorganisms (e.g., *E. coli* KO11) that will ferment sugar by-products of acid hydrolysis, but not MeGAX, and this occasions the need for supplementation of the fermentation process with a microorganism having the ability to ferment MeGAX in order to avoid low ethanol production rates and low ethanol yields, or low production rates and yields of other desirable bioproducts.

According to the subject invention, *Enterobacter asburiae* has been found to ferment MeGAX very well, thereby assisting in providing higher bioproduct yield over other known fermenting methods following acid hydrolysis. In one embodiment of the invention, *Enterobacter asburiae* strain JDR-1 is applied to by-products following dilute acid hydrolysis of biomass materials to produce high yields and concentrations of ethanol or other bioproducts. In a related embodiment, thermochemical and bioconversion processes involving the use of the microorganisms or enzymes derived therefrom, may be used for processing lignocellulosics to MeGAX, hexoses (e.g. fructose, glucose, mannose, galactose) or pentoses (e.g. arabinose and mannose) in combination with *Enterobacter asburiae* to ferment acid hydrolysis by-products of biomass materials. Other embodiments provide for the utilization of *Enterobacter asburiae* strains in combination with other bacterial strains for the simultaneous saccharification and fermentation of hexoses and pentoses to targeted biobased products.

Although the biocatalysts of the invention are particularly suited to facile bioprocessing of MeGAX-containing materials derived from biomass, the biocatalysts are by no means limited to bioprocessing of MeGAX-containing materials or materials derived from biomass. As would be appreciated by one of skill in the art, the biocatalysts of the invention may be used to convert a wide variety of different substrates into useful products regardless of the source of the substrates. In one embodiment, the substrate comprises a monsaccharide, disaccharide, trisaccharide, or oligosaccharide (wherein the oligosaccharide contains 4, 5, 6, 7, 8, or more simple sugars). In one embodiment, the substrate comprises a monosaccharide selected from xylose, glucose, mannose, galactose, arabinose, fructose, or rhamnose. In one embodiment, the substrate comprises glucuronic acid (or its conjugate base) and/or MeGAX. In one embodiment the substrate comprises an aldopentose, a ketopentose, an aldohexose, or a ketopentose. In one embodiment, the substrate comprises a sugar acid or a sugar alcohol.

The subject invention provides microorganisms useful in the production of ethanol, lactate, and other resources from recyclable photosynthetic resources. According to the subject invention, a means for fermenting aldobiuronate methylglucuronoxylose (MeGAX) is provided. In one embodiment, MeGAX is fermented following dilute acid hydrolysis of hemicellulose containing materials, thereby providing an inexpensive, effective, and improved bioproduct production rate than that observed with previous methods for fermenting acid-treated hemicellulose materials.

In one embodiment, *Enterobacter asburiae* strain is used following dilute acid treatment of materials containing hemicellulose for the large-scale bioconversion of MeGAX along with hexoses and pentoses to valuable resources such as ethanol, acetate, lactate, and other bioproducts. By using *Enterobacter asburiae* strain, either alone or in combination with other bacteria useful in the breakdown of sugars following dilute acid hydrolysis of hemicellulose containing materials, the subject invention provides improved rates and yields of ethanol and other bioproducts.

One aspect of the present invention is therefore related to a process for fermenting MeGAX to produce improved ethanol yields from biomass materials following acid hydrolysis comprising the steps of:
(a) forming a substrate from biomass materials containing hemicellulose;
(b) subjecting the substrate to acid hydrolysis;
(c) selecting and isolating a strain of *Enterobacter asburiae* that has the ability to ferment MeGAX to ethanol;
(d) inoculating the substrate with the selected strain of *Enterobacter asburiae* to ferment MeGAX under conditions favorable for cell viability and conversion of MEGAX to ethanol; and
(e) optionally, recovering ethanol produced through the fermentation process.

In one embodiment of the method of the present invention, the substrate is inoculated with other strains of bacteria such as *E. coli* KO11 or other ethanogenic strains of bacteria in addition to *Enterobacter asburiae*.

Additional advantages of this invention will become readily apparent from the ensuing description.

A species of the genus was isolated from a soil sample and maintained on an agar plate. This specific strain was biologically pure and is identified as namely *Enterobacter asburiae* strain JDR-1 (NRRL B-S0074).

Biomass materials that are applied to the process described herein are any known materials containing hemicellulose. Examples of biomass materials that can be used as described herein include, but are not limited to, materials comprising: sweetgum wood as representative of forest energy crops, wood preprocessed for cellulose production, rice straw, wood prunings, wood, wood waste, newspaper and/or other paper products, plant materials and/or tree cuttings obtained from, for example, miscanthus, switchgrass, elephant grass, energy cane, hemp, corn, *Eucalyptus* spp., poplar (including, for example, yellow poplar or tulip tree (*Lirodendron tulipifera*) or cottonwood), willow, sorghum, sugarcane, sugarcane bagasse, corn stalks, corn stover, wheat straw and/or various combinations thereof.

The culture medium used for fermentation in the present process can be any known culturing composition with suitable nitrogen sources, mineral supplements, vitamins, and carbon sources. In certain embodiments, the culture medium comprises MeGAX. Carbon sources may include D-glucose, D-xylose, D-xylobiose, D-xylotriose, D-mannose, L-arabinose, D-galactose, glucuronate and various combinations of such carbon sources.

Conditions suitable for cell viability and conversion of hydrolysates to ethanol and other bioproducts are well known to the skilled artisan. For example, oxygen tension for the fermentation process may vary widely and the oxygen tension can be either microaerophilic for batch fermentation, or the inoculated substrate may be sparged with a small amount of air in continuous fermentation techniques. Moreover, anaerobic fermentation may also be used. The technique will depend on the initial cell density, the substrate concentration, and the incubation condition of the inoculum. In certain embodiments, the pH of the fermentation medium can range from a pH of about 5.0-7.0. Other embodiments provide for the fermentation of MeGAX and/or other carbon sources at a pH greater than, or equal to, 5.0. The temperature of the fermentation process of the present invention can also vary considerably (from about 28° C. to about 37° C.). In various embodiments, the temperature can range from about 28° C. to about 35° C., 28° C. to about 33° C. or be maintained around about 30° C.

Additional embodiments relate to *Enterobacter asburiae* strains genetically modified to facilitate production of xylitol. Genetic modifications suitable for this purpose are set forth in U.S. patent application Ser. No. 11/523,403, published as US-2007-0072280-A1, the disclosures of which are incorporated herein by reference in their entirety. The genetically modified *Enterobacter* asburiae strains may contain, for example, one or more genetic modifications selected from the group consisting of:
  (a) incorporation and/or overexpression of a gene encoding CRP*;
  (b) incorporation and/or overexpression of a gene encoding xylose reductase;
  (c) incorporation and/or overexpression of a gene encoding xylitol dehydrogenase; and
  (d) inactivation of a gene encoding xylulokinase.

Combinations of these modifications suitable to the invention include: (a), (b), (c), (d), (a)&(b), (a)&(c), (a)&(d), (b)&(c), (b)&(d), (c)&(d), (a)&(b)&(c), (a)&(b)&(d), (a)&(c)&(d), (b)&(c)&(d), and (a)&(b)&(c)&(d). The genes encoding CRP*, xylose reductase, and xylitol dehydrogenase are independently native to *Enterobacter asburiae* or are exogenous, but preferably are exogenous. The inactivated gene is a native gene or is an exogenous gene previously introduced into the *Enterobacter asburiae* strain.

Additional embodiments relate to *Enterobacter asburiae* strains genetically modified to facilitate production of lactic acid (D(−)-lactic acid and/or L(+)-lactic acid). Genetic modifications suitable for this purpose are set forth in U.S. Pat. No. 7,098,009 and U.S. patent application Ser. No. 11/501,137 (published as US-2007-0037265-A1), the disclosures of which are incorporated herein by reference in their entirety. The genetically modified *Enterobacter asburiae* strains may contain, for example, one or more genetic modifications selected from the group consisting of:
  (a) incorporation and/or overexpression and/or inactivation of a gene encoding L-lactate dehydrogenase;
  (b) incorporation and/or overexpression and/or inactivation of a gene encoding D-lactate dehydrogenase;
  (c) inactivation of a gene encoding fumarate reductase (frd);
  (d) inactivation of a gene encoding alcohol/aldehyde dehydrogenase (adh);
  (e) inactivation of a gene encoding pyruvate formate lyase (pfl);
  (f) inactivation of a gene encoding acetate kinase (ack); and
  (g) inactivation of a gene encoding methylglyoxal synthase (mgs).

Combinations of these modifications suitable to the invention include: (a), (b), (e), (d), (e), (f), (g), (a)&(b), (a)&(c), (a)&(d), (a)&(e), (a)&(f), (a)&(g), (b)&(c), (b)&(d), (b)&(e), (b)&(f), (b)&(g), (c)&(d), (c)&(e), (c)&(f), (c)&(g), (d)&(e), (d)&(f), (d)&(g), (e)&(f), (e)&(g), (f)&(g), (a)&(b)&(c), (a)&(b)&(d), (a)&(b)&(e), (a)&(b)&(f), (a)&(b)&(g), (a)&(c)&(d), (a)&(c)&(e), (a)&(c)&(f), (a)&(c)&(g), (a)&(d)&(e), (a)&(d)&(f), (a)&(d)&(g), (a)&(e)&(f), (a)&(e)&(g), (a)&(f)&(g), (b)&(c)&(d), (b)&(c)&(e), (b)&(c)&(f), (b)&(c)&(g), (b)&(d)&(e), (b)&(d)&(f), (b)&(d)&(g), (b)&(e)&(f), (b)&(e)&(g), (b)&(f)&(g), (c)&(d)&(e), (c)&(d)&(f), (c)&(d)&(g), (c)&(e)&(f), (c)&(e)&(g), (c)&(f)&(g), (d)&(e)&(f), (d)&(e)&(g), (d)&(f)&(g), (e)&(f)&(g), (a)&(b)&

(c)&(d), (a)&(b)&(c)&(e), (a)&(b)&(c)&(f), (a)&(b)&(c)& (g), (a)&(b)&(d)&(e), (a)&(b)&(d)&(f), (a)&(b)&(d)&(g), (a)&(b)&(e)&(f), (a)&(b)&(e)&(g), (a)&(b)&(f)&(g), (a)& (c)&(d)&(e), (a)&(c)&(d)&(f), (a)&(c)&(d)&(g), (a)&(c)& (e)&(f), (a)&(c)&(e)&(g), (a)&(c)&(f)&(g), (a)&(d)&(e)& (f), (a)&(d)&(e)&(g), (a)&(d)&(f)&(g), (a)&(e)&(f)&(g), (b)&(c)&(d)&(e), (b)&(c)&(d)&(f), (b)&(c)&(d)&(g), (b)& (c)&(e)&(f), (b)&(c)&(e)&(g), (b)&(c)&(f)&(g), (b)&(d)& (e)&(f), (b)&(d)&(e)&(g), (b)&(d)&(f)&(g), (b)&(e)&(f)& (g), (c)&(d)&(e)&(f), (c)&(d)&(e)&(g), (c)&(d)&(f)&(g), (c)&(e)&(f)&(g), (d)&(e)&(f)&(g), (a)&(b)&(c)&(d)&(e), (a)&(b)&(c)&(d)&(f), (a)&(b)&(c)&(d)&(g), (a)&(b)&(c) &(e)&(f), (a)&(b)&(c)&(e)&(g), (a)&(b)&(c)&(f)&(g), (a)&(b)&(d)&(e)&(f), (a)&(b)&(d)&(e)&(g), (a)&(b)&(d) &(f)&(g), (a)&(b)&(e)&(f)&(g), (a)&(c)&(d)&(e)&(f), (a)&(c)&(d)&(e)&(g), (a)&(c)&(d)&(f)&(g), (a)&(c)&(e)& (f)&(g), (a)&(d)&(e)&(f)&(g), (b)&(c)&(d)&(e)&(f), (b)& (c)&(d)&(e)&(g), (b)&(c)&(d)&(f)&(g), (b)&(c)&(e)&(f)& (g), (b)&(d)&(e)&(f)&(g), (c)&(d)&(e)&(f)&(g), (a)&(b)& (c)&(d)&(e)&(f), (a)&(b)&(c)&(d)&(e)&(g), (a)&(b)&(c)& (d)&(f)&(g), (a)&(b)&(c)&(e)&(f)&(g), (a)&(b)&(d)&(e)& (f)&(g), (a)&(c)&(d)&(e)&(f)&(g), (b)&(c)&(d)&(e)&(f)& (g), and (a)&(b)&(c)&(d)&(e)&(f)&(g).

The genes L-lactate dehydrogenase and D-lactate dehydrogenase are independently native to *Enterobacter asburiae* or exogenous. It is understood, for example, that when L(+)-lactate production is desired, and the native lactate dehydrogenase is D-lactate dehydrogenase then the native lactate dehydrogenase may be inactivated and replaced with an exogenous L-lactate dehydrogenase, and so on. It is thus understood that the strains may be engineered to produce D-lactate, L-lactate, or a mixture of the two. The inactivated genes are native gene(s) and/or are exogenous gene(s) previously introduced into the *Enterobacter asburiae* strain.

Additional embodiments relate to *Enterobacter asburiae* strains genetically modified to facilitate production of ethanol. Genetic modifications suitable for this purpose are set forth in U.S. Pat. No. 7,098,009 and U.S. Pat. No. 5,000,000, the disclosures of which are incorporated herein by reference in their entirety. The genetically modified *Enterobacter asburiae* strains may contain, for example, one or more genetic modifications selected from the group consisting of:

(a) insertion and/or overexpression of a gene encoding pyruvate decarboxylase;
(b) insertion and/or overexpression of a gene encoding alcohol dehydrogenase;
(c) inactivation of a gene encoding lactate dehydrogenase;
(d) inactivation of a gene encoding phosphoenolpyruvate carboxylase;
(e) inactivation of a gene encoding acetate kinase; and
(f) inactivation of a gene encoding pyruvate formate lyase.

Combinations of these modifications suitable to the invention include: (a), (b), (c), (d), (e), (f), (a)&(b), (a)&(c), (a)& (d), (a)&(e), (a)&(f), (b)&(c), (b)&(d), (b)&(e), (b)&(f), (c)& (d), (c)&(e), (c)&(f), (d)&(e), (d)&(f), (e)&(f), (a)&(b)&(c), (a)&(b)&(d), (a)&(b)&(e), (a)&(b)&(f), (a)&(c)&(d), (a)& (c)&(e), (a)&(c)&(f), (a)&(d)&(e), (a)&(d)&(f), (a)&(e)& (f), (b)&(c)&(d), (b)&(c)&(e), (b)&(c)&(f), (b)&(d)&(e), (b)&(d)&(f), (b)&(e)&(f), (c)&(d)&(e), (c)&(d)&(f), (c)& (e)&(f), (d)&(e)&(f), (a)&(b)&(c)&(d), (a)&(b)&(c)&(e), (a)&(b)&(c)&(f), (a)&(b)&(d)&(e), (a)&(b)&(d)&(f), (a)& (b)&(e)&(f), (a)&(c)&(d)&(e), (a)&(c)&(d)&(f), (a)&(c)& (e)&(f), (a)&(d)&(e)&(f), (b)&(c)&(d)&(e), (b)&(c)&(d) (f), (b)&(c)&(e)&(f), (b)&(d)&(e)&(f), (c)&(d)&(e)&(f), (a)&(b)&(c)&(d)&(e), (a)&(b)&(c)&(d)&(f), (a)&(b)&(c)& (e)&(f), (a)&(b)&(d)&(e)&(f), (a)&(c)&(d)&(e)&(f), (b)& (c)&(d)&(e)&(f), and (a)&(b)&(c)&(d)&(e)&(f).

Preferably, a gene encoding pyruvate decarboxylase is supplied. In one embodiment, a gene encoding pyruvate decarboxylase and a gene encoding alcohol dehydrogenase are supplied, and preferably the two genes are *Z. mobilis* genes such as those contained within the PET operon. The inactivated genes are native gene(s) and/or are exogenous gene(s) previously introduced into the *Enterobacter asburiae* strain.

Additional embodiments relate to *Enterobacter asburiae* strains genetically modified to facilitate production of succinate and/or malate. Genetic modifications suitable for this purpose are set forth in PCT/US2008/057439 (published as WO2008/115958A3) and U.S. Pat. App. 61/166,093, the disclosures of which are incorporated herein by reference in their entirety. The genetically modified *Enterobacter asburiae* strains may contain, for example, one or more genetic modifications selected from the group consisting of:

(a) overexpression of a gene encoding PEP carboxykinase;
(b) inactivation of a gene encoding pyruvate formate lyase; and
(c) inactivation of a PEP-dependent phosphotransferase system gene.

Combinations of these modifications suitable to the invention include: (a), (b), (c), (a)&(b), (a)&(c), (b)&(c), and (a)& (b)&(c). The PEP carboxykinase gene may be native to *Enterobacter asburiae* or may be an exogenous gene. In one embodiment, the PEP carboxykinase gene is from *Escherichia coli*. The inactivated genes are native gene(s) and/or are exogenous gene(s) previously introduced into the *Enterobacter asburiae* strain.

For any strain modified to contain a combination of overexpression of a PEP carboxykinase gene, inactivation of a pyruvate formate lyase gene, and/or inactivation of a PEP-dependent phosphotransferase system gene, as set forth immediately above, additional genetic modifications are also suitable to the invention. The genetically modified *Enterobacter asburiae* strains may contain, for example, one or more further genetic modifications selected from the group consisting of:

(d) inactivation of a gene encoding acetate kinase;
(e) inactivation of a gene encoding alcohol dehydrogenase;
(f) inactivation of a gene encoding aspartate aminotransferase;
(g) inactivation of a gene encoding citrate lyase;
(h) inactivation of a gene encoding lactate dehydrogenase;
(i) inactivation of a gene encoding methylglyoxal synthase;
(j) inactivation of a gene encoding pyruvate oxidase;
(k) inactivation of a gene encoding phosphate acetyltransferase;
(l) inactivation of a gene encoding malic enzyme; and
(m) inactivation of a gene encoding threonine dehydratase.

Examples of various combinations of the above referenced genetic modifications include, and are not limited to:: d only, e only, f only, g only, h only, i only, j only, k only, l only, m only, d.e, d.f, d.g, d.h, d.i, d.j, d.k, d.l, d.m, e.f, e.g, e.h, e.i, e.j, e.k, e.l, e.m, f.g, f.h, f.i, fj, f.k, f.l, f.m, g.h, g.i, g.j, g.k, g.l, g.m, h.i, h.j, h.k, h.l, h.m, i.j, i.k, i.l, i.m, j.k, j.l, j.m. k.l, k.m, l.m, d.e.f, d.e.g, d.e.h, d.e.i, d.e.j, d.e.k, d.e.l, d.e.m, d.f.g, d.f.h, d.f.i, d.f.j, d.f.k, d.f.1, d.f.m, d.g.h, d.g.i, d.g.j, d.g.k, d.g.l, d.g.m, d.h.i, d.h.j, d.h.k, d.h.l, d.h.m, d.i.j, d.i.k, d.i.l, d.i.m, d.j.k, d.j.l, d.j.m, d.k.l, d.k.m, d.l.m, e.f.g, e.f.h, e.f.i, e.f.j, e.f.k, e.f.1, e.f.m, e.g.h, e.g.i, e.g.j, e.g.k, e.g.l, e.g.m, e.h.i, e.h.j, e.h.k, e.h.l, e.h.m, e.i.j, e.i.k, e.i.l, c.i.m, e.j.k, e.j.l, e.j.m, e.k.l, e.k.m, e.l.m, f.g.h, f.g.i, f.g.j, f.g.k, f.g.l, f.g.m, f.h.i, fh.j, f.h.k, f.h.l, f.h.m, f.i.j, f.i.k, f.i.l, f.i.m, f.j.k, f.j.l, f.j.m, f.k.l, f.k.m, f.l.m, g.h.i, g.h.j, g.h.k, g.h.l, g.h.m, g.i.j, g.i.k, g.i.l, g.i.m, g.j.k, g.j.l, g.j.m, g.k.l, g.k.m, g.l.m, h.i.j, h.i.k, h.i.l, h.i.m, h.j.k, h.j.l, h.j.m, h.k.l, h.k.m, h.l.m, i.j.k, i.j.l, i.j.m, i.k.l, i.k.m, l.l.m, j.k.l, j.k.m, j.l.m, k.l.m, d.e.f.g, d.e.f.h, d.e.f.i, d.e.f.j, d.e.f.k, d.e.f.l, d.e.f.m, d.e.g.h, d.e.g.i, d.e.g.j, d.e.g.k, d.e.g.l, d.e.g.m, d.e.h.i, d.e.h.j, d.e.h.k, d.e.h.l, d.e.h.m, d.e.i.j, d.e.i.k, d.e.i.l, d.e.i.m, d.e.j.k, d.e.j.l, d.e.j.m, d.e.k.l, d.e.k.m, d.e.l.m, d.f.g.h, d.f.g.i, d.f.g.j, d.f.g.k, d.f.g.l, d.f.g.m, d.f.h.i, d.f.h.j, d.f.h.k, d.f.h.l, d.f.h.m, d.f.i.j, d.f.i.k, d.f.i.l, d.f.i.m, d.f.j.k, d.f.j.l, d.f.j.m, d.f.k.l, d.f.k.m, d.f.l.m, d.g.h.i, d.g.h.j, d.g.h.k, d.g.h.l, d.g.h.m, d.g.i.j, d.g.i.k, d.g.i.l, d.g.i.m, d.g.j.k, d.g.j.l, d.g.j.m, d.g.k.l, d.g.k.m, d.g.l.m, d.h.i.j, d.h.i.k, d.h.i.l, d.h.i.m, d.h.j.k, d.h.j.l, d.h.j.m, d.h.k.l, d.h.k.m, d.h.l.m, d.i.j.k, d.i.j.l, d.i.j.m, d.i.k.l, d.i.k.m, d.i.l.m, d.j.k.l, d.j.k.m, d.j.l.m, d.k.l.m, e.f.g.h, e.f.g.i, e.f.g.j, e.f.g.k, e.f.g.l, e.f.g.m, e.f.h.i, e.f.h.j, e.f.h.k, e.f.h.l, e.f.h.m, e.f.i.j, e.f.i.k, e.f.i.l, e.f.i.m, e.f.j.k, e.f.j.l, e.f.j.m, e.f.k.l, e.f.k.m, e.f.l.m, e.g.h.i, e.g.h.j, e.g.h.k, e.g.h.l, e.g.h.m, e.g.i.j, e.g.i.k, e.g.i.l, e.g.i.m, e.g.j.k, e.g.j.l, e.g.j.m, e.g.k.l, e.g.k.m, e.g.l.m, e.h.i.j, e.h.i.k, e.h.i.l, e.h.i.m, e.h.j.k, e.h.j.l, e.h.j.m, e.h.k.l, e.h.k.m, e.h.l.m, e.i.j.k, e.i.j.l, e.i.j.m, e.i.k.l, e.i.k.m, e.i.l.m, e.j.k.l, e.j.k.m, e.k.l.m, f.g.h.i, f.g.h.j, f.g.h.k, f.g.h.l, f.g.h.m, f.g.i.j, f.g.i.k, f.g.i.l, f.g.i.m, f.g.j.k, f.g.j.l, f.g.j.m, f.g.k.l, f.g.k.m, f.g.l.m, f.h.i.j, f.h.i.k, f.h.i.l, f.h.i.m, f.h.j.k, f.h.j.l, f.h.j.m, f.h.k.l, f.h.k.m, f.h.l.m, f.i.j.k, f.i.j.l, f.i.j.m, f.i.k.l, fi.k.m, f.j.k.l, f.j.k.m, f.j.l.m, f.k.l.m, g.h.i.j, g.h.i.k, g.h.i.l, g.h.i.m, g.h.j.k, g.h.j.l, g.h.j.m, g.h.k.l, g.h.k.m, g.h.l.m, g.i.j.k, g.i.j.l, g.i.j.m, g.i.k.l, g.i.k.m, g.i.l.m, g.j.k.l, g.j.k.m, g.j.l.m, g.k.l.m, h.i.j.k, h.i.j.l, h.i.j.m, h.i.k.l, h.i.k.m, h.i.l.m, h.j.k.l, h.j.k.m, h.k.l.m, i.j.k.l, i.j.k.m, i.j.l.m, i.k.l.m, j.k.l.m, d.e.f.g.h, d.e.f.g.i, d.e.f.g.j, d.e.f.g.k, d.e.f.g.l, d.e.f.g.m, d.e.f.h.i, d.e.f.h.j, d.c.f.h.k, d.e.f.h.l, d.e.f.h.m, d.e.f.i.j, d.e.f.i.k, d.e.f.i.l, d.e.f.i.m, d.e.f.j.k, d.e.f.j.l, d.e.f.j.m, d.e.f.k.l, d.e.f.k.m, d.e.f.l.m, d.e.g.h.i, d.e.g.h.j, d.e.g.h.k, d.c.g.h.l, d.e.g.h.m, d.e.g.i.j, d.e.g.i.k, d.e.g.i.l, d.e.g.i.m, d.e.g. j.k, d.e.g. j.l, d.e.g. j.m, d.e.g. k.l, d.e.g. k.m, d.e.g. l.m, d.e.h.i.j, d.e.h.i.k, d.e.h.i.l, d.e.h.i.m, d.e.h.j.k, d.e.h.j.l, d.e.h.j.m, d.e.h.k.l, d.e.h.k.m, d.e.h.l.m, d.e.i.j.k, d.e.i.j.l, d.e.i.j.m, d.e.i.k.l, d.e.i.k.m, d.e.i.l.m, d.e.j.k.l, d.e.j.k.m, d.e.j.l.m, d.e.k.l.m, d.f.g.h.i, d.f.g.h.j, d.f.g.h.k, d.f.g.h.l, d.f.g.h.m, d.f.g.i.j, d.f.g.i.k, d.f.g.i.l, d.f.g.i.m, d.f.g.j.k, d.f.g.j.l, d.f.g.j.m, d.f.g.k.l, d.f.g.k.m, d.f.g.l.m, d.f.h.i.j, d.f.h.i.k. d.f.h.i.l, d.f.h.i.m, d.f.h.j.k, d.f.h.j.l, d.f.h.j.m, d.f.h.k.l, d.f.h.k.m, d.f.h.l.m, d.f.i.j.k, d.f.i.j.l, d.f.i.j.m, d.f.i.k.l, d.f.i.k.m, d.f.i.l.m, d.f.j.k.l, d.f.j.k.m, d.f.j.l.m, d.f.k.l.m, d.g.h.i.j, d.g.h.i.k, d.g.b.i.l, d.g.h.i.m, d.g.h.j.k, d.g.h.j.l, d.g.h.j.m, d.g.h.k.l, d.g.h.k.m, d.g.h.l.m, d.g.i.j.k, d.g.i.j.l, d.g.i.j.m, d.g.i.k.l, d.g.i.k.m, d.g.i.l.m, d.g.j.k.l, d.g.j.k.m, d.g.j.l.m, d.g.k.l.m, d.h.i.j.l, d.h.i.j.m, d.h.i.k.l, d.h.i.k.m, d.h.i.l.m, d.h.j.k.l, d.h.j.k.m, d.h.j.l.m, d.h.k.l.m, d.i.j.k.l, d.i.j.k.m, d.i.j.l.m, d.i.k.l.m, d.j.k.l.m, e.f.g.h.i, e.f.g.h.j, e.f.g.h.k, e.f.g.h.l, e.f.g.h.m, e.f.g.i.j, e.f.g.i.k, e.f.g.i.l, e.f.g.i.m, e.f.g.j.k, e.f.g.j.l, e.f.g.j.m, e.f.g.k.l, e.f.g.k.m, e.f.g.l.m, e.f.h.i.j, e.f.h.i.k, e.f.h.i.l, e.f.h.i.m, e.f.h.j.k, e.f.h.j.l, e.f.h.j.m, e.f.h.k.l, c.f.h.k.m, e.f.h.l.m, e.f.i.j.k, e.f.i.j.l, e.f.i.j.m, e.f.i.k.l, e.f.i.k.m, e.f.i.l.m, e.f.j.k.l, e.f.j.k.m, e.f.j.l.m, e.f.k.l.m, e.g.h.i.j, e.g.h.i.k, e.g.h.i.l, e.g.h.i.m, e.g.h.j.k, e.g.h.j.l, e.g.h.j.m, e.g.h.k.l, e.g.h.k.m, e.g.h.l.m, e.g. i.j.k, e.g. i.j.l, e.g. i.j.m, e.g. i.k.l, e.g. i.k.m, e.g. i.l.m, e.g. j.k.l, e.g. j.k.m, e.g. k.l.m, e.h.i.j.k, e.h.i.j.l, e.h.i.j.m, e.h.i.k.l, e.h.i.k.m, e.h.i.l.m, e.h.j.k.l, e.h.j.k.m, e.h.j.l.m, e.h.k.l.m, e.i.j.k.l, e.i.j.k.m, e.i.j.l.m, e.i.k.l.m, e.j.k.l.m, f.g.h.i.j, f.g.h.i.k, f.g.h.i.l, f.g.h.i.m, f.g.h.j.k, f.g.h.j.l, f.g.h.j.m, f.g.h.k.l, f.g.h.k.m, f.g.h.l.m, f.g.i.j.l, f.g.i.j.m, f.g.i.k.l, f.g.i.k.m, f.g.i.l.m, f.g.j.k.l, f.g.j.k.m, f.g.j.l.m, f.g.k.l.m, f.h.i.j.k, f.h.i.j.l, f.h.i.j.m, f.h.i.k.l, f.h.i.k.m, f.h.i.l.m, f.h.j.k.l, f.h.j.k.m, f.h.j.l.m, f.h.k.l.m, f.i.j.k.m, f.i.j.l.m, fi.k.l.m, f.j.k.l.m, g.h.i.j.k, g.h.i.j.m, g.h.i.k.l, g.h.i.k.m, g.h.i.l.m, g.h.j.k.l, g.h.j.k.m, g.h.j.l.m, g.h.k.l.m, g.i.j.k.l, g.i.j.k.m, g.i.j.l.m, g.i.k.l.m, g.j.k.l.m, h.i.j.k.l, h.i.j.k.m, h.i.j.l.m, h.i.k.l.m, h.j.k.l.m, i.j.k.l.m, d.e.f.g.h.i, d.e.f.g.h.j, d.e.f.g.h.k, d.e.f.g.h.l, d.e.f.g.h.m, d.e.f.g.i.j, d.e.f.g.i.k, d.e.f.g.i.l, d.e.f.g.i.m, d.e.f.g.j.k, d.e.f.g.j.l, d.e.f.g.j.m, d.e.f.g.k.l, d.e.f.g.k.m, d.e.f.g.l.m, d.e.f.h.i.j, d.e.f.h.i.k, d.e.f.h.i.l, d.e.f.h.i.m, d.e.f.h.j.k, d.e.f.h.j.l, d.e.f.h.j.m, d.e.f.h.k.l, d.e.f.h.k.m, d.e.f.h.l.m, d.e.f.i.j.k, d.e.f.i.j.l, d.e.f.i.j.m, d.e.f.i.k.l, d.e.f.i.k.m, d.e.f.i.l.m, d.e.f.j.k.l, d.e.f.j.k.m, d.e.f.j.l.m, d.e.f.k.l.m, d.e.g.h.i.j, d.e.g.h.i.k, d.e.g.h.i.l, d.e.g.h.i.m, d.e.g.h.j.k, d.e.g.h.j.l, d.e.g.h.j.m, d.e.g.h.k.l, d.e.g.h.k.m, d.e.g.h.l.m, d.e.g.i.j.k, d.e.g.i.j.l, d.e.g.i.j.m, d.e.g.i.k.l, d.e.g.i.k.m, d.e.g.i.l.m, d.e.g. j.k.l, d.e.g. j.k.m, d.e.g. j.l.m, d.e.g. k.l.m, d.e.h.i.j.k, d.e.h.i.j.l, d.e.h.i.j.m, d.e.h.i.k.l, d.e.h.i.k.m, d.e.h.i.l.m, d.e.h.j.k.l, d.e.h.j.k.m, d.e.h.j.l.m, d.e.h.k.l.m, d.e.i.j.k.l, d.e.i.j.k.m, d.e.i.j.l.m, d.e.i.k.l.m, d.e.j.k.l.m, d.f.g.h.i.j, d.f.g.h.i.k, d.f.g.h.i.l, d.f.g.h.i.m, d.f.g.h.j.k, d.f.g.h.j.l, d.f.g.h.j.m, d.f.g.h.k.l, d.f.g.h.k.m, d.f.g.h.l.m, d.f.g.i.j.k, d.f.g.i.j.l, d.f.g.i.j.m, d.f.g.i.k.l, d.f.g.i.k.m, d.f.g.i.l.m, d.f.g.j.k.l, d.f.g.j.k.m, d.f.g.j.l.m, d.f.g.k.l.m, d.f.h.i.j.k, d.f.h.i.j.l, d.f.h.i.j.m, d.f.h.i.k.l, d.f.h.i.k.m, d.f.h.i.l.m, d.f.h.j.k.l, d.f.h.j.l.m, d.f.h.k.l.m, d.f.i.j.k.l, d.f.i.j.k.m, d.f.i.j.l.m, d.f.i.k.l.m, d.f.j.k.l, d.f.j.k.m, d.g.h.i.j.k, d.g.h.i.j.l, d.g.h.i.j.m, d.g.h.i.k.l, d.g.h.i.k.m, d.g.h.i.l.m, d.g.h.j.k.l, d.g.h.j.k.m, d.g.h.j.l.m, d.g.h.k.l.m, d.g.i.j.k.l, d.g.i.j.k.m, d.g.i.j.l.m, d.g.i.k.l.m, d.g.j.k.l.m, d.h.i.j.k.l, d.h.i.j.l.m, d.i.j.k.l.m, e.f.g.h.i.j, e.f.g.h.i.k, e.f.g.h.i.l, e.f.g.h.i.m, e.f.g.h.j.k, e.f.g.h.j.l, e.f.g.h.j.m, e.f.g.h.k.l, c.f.g.h.k.m, e.f.g.h.l.m, e.f.g.i.j.k, e.f.g.i.j.l, e.f.g.i.j.m, e.f.g.i.k.l, e.f.g.i.k.m, e.f.g.i.l.m, e.f.g.j.k.l, e.f.g.j.k.m, e.f.g.j.l.m, e.f.g.k.l.m, e.f.h.i.j.k, e.f.h.i.j.l, e.f.h.i.j.m, e.f.h.i.k.l, e.f.h.i.k.m, e.f.h.i.l.m, e.f.h.j.k.l, e.f.h.j.k.m, e.f.h.j.l.m, e.f.h.k.l.m, e.f.i.j.k.l, e.f.i.j.k.m, e.f.i.j.l.m, e.f.i.k.l.m, e.f.j.k.l.m, e.g.h.i.j.k, e.g.h.i.j.l, e.g.h.i.j.m, e.g.h.i.k.l, e.g.h.i.k.m, e.g.h.i.l.m, e.g.h.j.k.l, e.g.h.j.k.m, e.g.h.j.l.m, e.g.h.k.l.m, e.g. i.j.k.l, e.g. i.j.k.m, e.g. i.j.l.m, e.g. i.k.l.m, e.g.j.k.l.m, e.h.i.j.k.l, e.h.i.j.k.m, e.h.i.j.l.m, e.h.i.k.l.m, c.h.j.k.l.m, e.i.j.k.l.m, f.g.h.i.j.k, f.g.h.i.j.l, f.g.h.i.j.m, f.g.h.i.k.l, f.g.h.i.k.m, f.g.h.i.l.m, f.g.h.j.k.l, f.g.h.j.k.m, f.g.h.j.l.m, f.g.h.k.l.m, f.g.i.j.k.l, f.g.i.j.k.m, f.g.i.j.l.m, f.g.i.k.l.m, f.g.j.k.l.m, f.h.i.j.k.l, f.h.i.j.k.m, f.h.i.j.l.m, f.h.i.k.l.m, f.h.j.k.l.m, f.i.j.k.l.m, g.h.i.j.k.l, g.h.i.j.k.m, g.h.i.j.l.m, g.h.i.k.l.m, g.h.j.k.l.m, g.i.j.k.l.m, h.i.j.k.l.m, d.e.f.g.h.i.j, d.e.f.g.h.i.k, d.e.f.g.h.i.l, d.e.f.g.h.i.m, d.e.f.g.h.j.k, d.e.f.g.h.j.l, d.e.f.g.h.j.m, d.e.f.g.h.k.l, d.e.f.g.h.k.m, d.c.f.g.h.l.m, d.e.f.g.i.j.k, d.e.f.g.i.j.l, d.e.f.g.i.j.m, d.e.f.g.i.k.l, d.e.f.g.i.k.m, d.e.f.g.i.l.m, d.e.f.g.j.k.l, d.e.f.g.j.k.m, d.e.f.g.j.l.m, d.e.f.g.k.l.m, d.e.f.h.i.j.k, d.e.f.h.i.j.l, d.e.f.h.i.j.m, d.e.f.h.i.k.l, d.e.f.h.i.k.m, d.e.f.h.i.l.m, d.e.f.h.j.k.l, d.e.f.h.j.k.m, d.e.f.h.j.l.m, d.e.f.h.k.l.m, d.e.f.i.j.k.l, d.e.f.i.j.k.m. d.e.f.i.j.l.m, d.e.f.i.k.l.m, d.e.f.j.k.l.m, d.e.g.h.i.j.k, d.e.g.h.i.j.l, d.e.g.h.i.j.m, d.e.g.h.i.k.l, d.e.g.h.i.k.m, d.e.g.h.i.l.m, d.e.g.h.j.k.l, d.e.g.h.j.k.m, d.e.g.h.j.l.m, d.e.g.h.k.l.m, d.e.g.i.j.k.l, d.e.g.i.j.k.m, d.e.g.i.j.l.m, d.e.g.i.k.l.m, d.e.g. j.k.l.m, d.e.h.i.j.k.l, d.e.h.i.j.k.m, d.c.h.i.j.l.m, d.e.h.i.k.l.m, d.c.h.j.k.l.m, d.e.i.j.k.l.m, d.f.g.h.i.j.k, d.f.g.h.i.j.l, d.f.g.h.i.k.l, d.f.g.h.i.k.m, d.f.g.h.i.l.m, d.f.g.h.j.k.l, d.f.g.h.j.k.m, d.f.g.h.j.l.m, d.f.g.h.k.l.m, d.f.g.i.j.k.l, d.f.g.i.j.k.m, d.f.g.i.j.l.m, d.f.g.i.k.l.m, d.f.gj.k.l.m, d.f.h.i.j.k.l, d.f.h.i.j.k.m, d.f.h.i.j.l.m, d.f.h.i.k.l.m, d.f.h.j.k.l.m, d.f.i.j.k.l.m, d.g.h.i.j.k.l, d.g.h.i.j.k.m, d.g.h.i.j.l.m, d.g.h.i.k.l.m, d.g.h.j.k.l.m, d.g.i.j.k.l.m, d.h.i.j.k.l.m, e.f.g.h.i.j.k, e.f.g.h.i.j.l, e.f.g.h.i.j.m, e.f.g.h.i.k.l, e.f.g.h.i.k.m, e.f.g.h.i.l.m, e.f.g.h.j.k.l, e.f.g.h.j.k.m, e.f.g.h.j.l.m, e.f.g.h.k.l.m, e.f.g.i.j.k.l, e.f.g.i.j.k.m, e.f.g.i.j.l.m, e.f.g.i.k.l.m, e.f.gj.k.l.m, e.f.h.i.j.k.l, e.f.h.i.j.k.m, e.f.h.i.j.l.m, e.f.h.i.k.l.m, e.f.h.j.k.l.m, e.f.i.j.k.l.m, e.g.h.i.j.k.l, e.g.h.i.j.k.m, e.g.h.i.j.l.m, e.g.h.i.k.l.m, e.g.h.j.k.l.m, e.g. ij.k.l.m, e.h.i.j.k.l.m, f.g.h.i.j.k.l, f.g.h.i.j.k.m, f.g.h.i.j.l.m, f.g.h.i.k.l.m, f.g.h.j.k.l.m, f.g.i.j.k.l.m, f.h.i.j.k.l.m, g.h.i.j.k.l.m, d.e.f.g.h.i.j.k, d.e.f.g.h.i.j.l, d.e.f.g.h.i.j.m, d.e.f.g.h.i.k.l, d.e.f.g.h.i.k.m, d.e.f.g.h.i.l.m, d.e.f.g.h.j.k.l, d.e.f.g.h.j.k.m, d.e.f.g.h.j.l.m, d.e.f.g.h.k.l.m, d.e.f.g.i.j.k.l, d.e.f.g.i.j.k.m, d.e.f.g.i.j.l.m, d.e.f.g.i.k.l.m, d.e.f.g.j.k.l.m, d.e.f.h.i.j.k.l, d.e.f.h.i.j.k.m, d.e.f.h.i.j.l.m, d.e.f.h.i.k.l.m, d.e.f.h.j.k.l.m, d.e.f.i.j.k.l.m, d.e.g.h.i.j.k.l, d.e.g.h.i.j.k.m, d.e.g.h.i.j.l.m, d.e.g.h.i.k.l.m, d.e.g.h.j.k.l.m, d.e.g.i.j.k.l.m, d.e.h.i.j.k.l.m, d.f.g.h.i.j.k.l, d.f.g.h.i.j.k.m, d.f.g.h.i.j.l.m, d.f.g.h.i.k.l.m, d.f.g.h.j.k.l.m, d.f.g.i.j.k.l.m, d.f.h.i.j.k.l.m, d.g.h.i.j.k.l.m, e.f.g.h.i.j.k.l, e.f.g.h.i.j.k.m, e.f.g.h.i.j.l.m, e.f.g.h.i.k.l.m, e.f.g.h.j.k.l.m, e.f.g.i.j.k.l.m, e.f.h.i.j.k.l.m, e.g.h.i.j.k.l.m, f.g.h.i.j.k.l.m, d.e.f.g.h.i.j.k.l, d.e.f.g.h.i.j.k.m, d.e.f.g.h.i.j.l.m, d.e.f.g.h.i.k.l.m, d.e.f.g.h.j.k.l.m, d.e.f.g.i.j.k.l.m, d.e.f.h.i.j.k.l.m, d.e.g.h.i.j.k.l.m, d.fg.h.i.j.k.l.m, e.f.g.h.i.j.k.l.m, and d.e.f.g.h.i.j.k.l.m, wherein commas separate the individual combinations. Optionally, a gene encoding formate transporter may also be inactivated. The inactivated genes are native gene(s) and/or are exogenous gene(s) previously introduced into the *Enterobacter asburiae* strain.

Additional embodiments relate to *Enterobacter asburiae* strains genetically modified to facilitate production of alanine. Genetic modifications suitable for this purpose are set forth in PCT/US2008/058410 (published as WO2008/119009A2), the disclosures of which are incorporated herein by reference in their entirety. The genetically modified *Enterobacter asburiae* strains may contain, for example, one or more genetic modifications selected from the group consisting of:

(a) incorporation and/or overexpression of a gene encoding alanine dehydrogenase;
(b) inactivation of a gene encoding alanine racemase;
(c) inactivation of a gene encoding lactate dehydrogenase;
(d) inactivation of a gene encoding alcohol dehydrogenase;
(e) inactivation of a gene encoding fumarate reductase;
(f) inactivation of a gene encoding pyruvate formate lyase;
(g) inactivation of a gene encoding acetate kinase; and
(h) inactivation of a gene encoding methylglyoxal synthase.

Combinations of these modifications suitable to the invention include: a, b, c, d, e, f, g, h, a.b, a.c, a.d, a.e, a.f, a.g, a.h, b.c, b.d, b.e, b.f, b.g, b.h, c.d, c.e, c.f, c.g, c.h, d.e, d.f, d.g, d.h, e.f, e.g, e,h, f.g, f.h, g.h, a.b.c, a.b.d, a.b.e, a.b.f, a.b.g, a.b.h, a.c,d, a.c.e, a.c.f, a.c.g, a.c.h, a.d.e, a.d.f, a.d.g, a.d.h, a.e.f, a.e.g, a.e.h, a.f.h, a.g.h, b.c.d, b.c.e, b.c.f, b.c.g, b.c.h, b.d.e, b.d.f, b.d.g, b.d.h, b.e.f, b.e.g, b.e.h, b.f.g, b.f.h, b.g.h, c.d.e, c.d.f, c.d.g, c.d.h, c.e.f, c.e.g, c.e.h, c.f.g, c.f.h, c.g.h, d.e.f, d.e.g, d.e.h, d.f.g, d.f.h, d.g.h, e.f.h, e.g.h, f.g.h, a.b.c.d, a.b.c.e, a.b.c.f, a.b.c.g, a.b.c.h, a.b.d.e, a.b.d.f, a.b.d.g, a.b.d.h, a.b.e.f, a.b.e.g, a.b.e.h, a.b.f.g, a.b.f.h, a.b.g.h, a.c.d.e, a.c.d.f, a.c.d.g, a.c.d.h, a.c.e.f, a.c.e.g, a.c.e.h, a.c.f.g, a.c.f.h, a.c.g.h, a.d.e.f, a.d.e.g, a.d.e.h, a.d.f.g, a.d.f.h, a.d.g.h, a.e.f.g, a.e.f.h, a.e.g.h, a.f.g.h, b.c.d.e, b.c.d.f, b.c.d.g, b.c.d.h, b.c.e.f, b.c.e.g, b.c.e.h, b.c.fg, b.c.f.h, b.c.g.h, b,d.e.f, b.d.e.g, b.d.e.h, b.d.f.g, b.d.f.h, b.d.g.h, b.e.f.g, b.e.f.h, b.e.g.h, b.f.g.h, c.d.e.f, c.d.e.g, c.d.e.h, c.d.f.g, c.d.f.h, c.d.g.h, c.e.f.g, c.e.f.h, c.e.g.h, c.f.g.h, d.e.f.g, d.e.f.h, d.e.g.h, d.f.g.h, e.f.g.h, a.b.c.d.e, a.b.c.d.f, a.b.c.d.g, a.b.c.d.h, a.b.c.e.f, a.b.c.e.g, a.b.c.e.h, a.b.c.f.g, a.b.c.f.h, a.b.c.g.h, a.b.d.e.f, a.b.d.e.g, a.b.d.e.h, a.b.d.f.g, a.b.d.f.h, a.b.d.g.h, a.b.e.f.g, a.b.e.f.h, a.b.e.g.h, a.b.f.g.h, a.c.d.e.f, a.c.d.e.g, a.c.d.e.h, a.c.d.f.g, a.c.d.f.h, a.c.d.g.h, a.c.e.f.g, a.c.e.f.h, a.c.e.g.h, a.c.f.g.h, a.d.e.f.h, a.d.e.g.h, a.d.f.g.h, a.e.f.g.h, b.c.d.e.f, b.c.d.e.g, b.c.d.e.h, b.c.d.f.g, b.c.d.f.h, b.c.d.g.h, b.c.e.f.g, b.c.e.f.h, b.c.e.g.h, b.c.f.g.h,
b.d.e.f.g, b.d.e.f.h, b.d.e.g.h, b.d.f.g.h, b.e.f.g.h, c.d.e.f.g, c.d.e.g.h, c.d.f.g.h, c.e.f.g.h, d.e.f.g.h, a.b.c.d.e.f, a.b.c.d.e.g, a.b.c.d.e.h, a.b.c.d.f.g, a.b.c.d.f.h, a.b.c.d.g.h, a.b.c.e.f.g, a.b.c.e.f.h, a.b.c.e.g.h, a.b.c.f.g.h, a.b.d.e.f.g, a.b.d.f.g.h, a.b.e.f.g.h, a.c.d.e.f.g, a.c.d.e.f.h, a.c.d.e.g.h, a.c.d.f.g.h, a.c.e.f.g.h, a.d.e.f.g.h, b.c.d.e.f.g, b.c.d.e.f.h, b.c.d.e.g. b.c.d.f.g.h, b.c.e.f.g.h, b.d.e.f.g.h, c.d.e.f.g.h, a.b.c.d.e.f.g, a.b.c.d.e.f.h, a.b.c.d.e.g.h, a.b.c.d.f.g.h, a.b.c.e.f.g.h, a.b.d.e.f.g.h, a.c.d.e.f.g.h, b.c.d.e.f.g.h, and a.b.c.d.e.f.g.h. Preferably incorporation and/or overexpression of a gene encoding alanine dehydrogenase is present in the genetically modified *Enterobacter asburiae* strain intended for the production of alanine. In one embodiment, the gene encoding alanine dehydrogenase is from *Geobacillus stearothermophilus* or from another thermophilic microorganism. The inactivated genes are native gene(s) and/or are exogenous gene(s) previously introduced into the *Enterobacter asburiae* strain.

Additional embodiments relate to *Enterobacter asburiae* strains genetically modified to enhance their capacity to utilize lignocellulose. Genetic modifications suitable for this purpose are set forth in PCT/US2008/058410 (published as WO2008/119009A2); in Ingrain et al., *Appl Environ Microbiol* 67(1): 6-14 (2001); and in Ingram et al., *Appl Environ Microbiol* 63(12): 4633-4637 (1997); the disclosures of which are incorporated herein by reference in their entirety. The genetically modified *Enterobacter asburiae* strains may contain, for example, one or more genetic modifications selected from the group consisting of:

(a) incorporation and/or overexpression of a gene encoding cellobiose utilizing enzyme;
(b) incorporation and/or overexpression of a gene encoding phospho-β-glucosidase; and
(c) incorporation and/or overexpression of a gene encoding an endoglucanase or cellulase.

Combinations of these modifications suitable to the invention include: a; b; c; a&b; a &c; h&c; and a&b&c. In one embodiment, the gene encoding cellobiose utilizing enzyme and/or the gene encoding phospho-β-glucosidase are genes from *Klebsiella*, and preferably are *Klebsiella oxytoca* casAB. In one embodiment the gene encoding an endoglucanase or cellulase is a gene from *Erwinia*, and preferably is *Erwinia chrysanthemi* celY or *Erwinia chrysanthemi* celZ. In one embodiment the genes are integrated such that transcription is via a promoter native to *Enterobacter* generally or to *Enterobacter asburiae* specifically.

Additional embodiments relate to *Enterobacter asburiae* strains genetically modified to facilitate production of acetate and/or pyruvate. Genetic modifications suitable for this purpose are set forth in U.S. patent application Ser. No. 10/703, 812, the disclosure of which is incorporated herein by reference in its entirety. The genetically modified *Enterobacter asburiae* strains may contain, for example, one or more genetic modifications selected from the group consisting of:

(a) inactivation of a gene encoding lactate dehydrogenase;
(b) inactivation of a gene encoding pyruvate formatelyase;
(c) inactivation of a gene encoding fumarate reductase;
(d) inactivation of a gene encoding $(F_1F_0)H^+$-ATP synthase;
(e) inactivation of a gene encoding alcohol/aldehyde dehydrogenase; and
(f) inactivation of a gene encoding 2-ketoglutarate dehydrogenase.

Combinations of these modifications suitable to the invention include: a; h; c; d; e; f; a&b; a&c; a&d; a&e; a&f; b&c; b&d; b&e; b&f; c&d; c&e; c&f; d&e; d&f; e&f; a&b&c; a&b&d; a&b&e; a&b&f; a&c&d; a&c&e; a&c&f; a&d& e;

a&d&f; a&e&f; b&c&d; b&c&e; b&c&f; b&d&e; b&d&f; b&e&f; c &d&e; c&d&f; c&e&f; d&e&f; a&b&c&d; a&b&c&e; a&b&c&f; a&b &d&e; a&b&d&f; a&b&e&f; a&c&d&e; a&c&d&f; a&c&d&e&f; a&d& e&f; b&c&d&e; b&c&d&f; b&c&e&; b&d&e&f; c&d&e&f; a&b&c &d&e; a&b&c&d&f; a&b&c&e&f; a&b&d&e&f; a&c&d&e&f&b&c &d&e&f; and a&b&c&d&e&f. Any strain containing any of these combinations of modifications may be further modified to inactivate a gene encoding formate transporter, for example focA.

In one embodiment, the inactivation of the gene encoding $(F_1F_0)H^+$-ATP synthase preserves the hydrolytic activity of F1-ATPase in the cytoplasm while disrupting oxidative phosphorylation. In one embodiment, the gene encoding $(F_1F_0)$ HtATP synthase is atpF or atpH or both. In one embodiment, the gene encoding lactate dehydrogenase is ldhA. In one embodiment, the gene encoding pyruvate formate lyase is pflB. In one embodiment, the gene encoding fumarate reductase is one or more of the component genes of frdABCD, for example frdBC or frdCD. In one embodiment the gene encoding alcohol/aldehyde dehydrogenase is adhE. In one embodiment, the gene encoding 2-ketoglutarate dehydrogenase is sucA.

For any strain modified to contain any combination of inactivation of a gene encoding lactate dehydrogenase, inactivation of a gene encoding pyruvate formate lyase, inactivation of a gene encoding fumarate reductase, inactivation of a gene encoding $(F_1F_0)H^+$-ATP synthase, inactivation of a gene encoding alcohol/aldehyde dehydrogenase, and/or inactivation of a gene encoding 2-ketoglutarate dehydrogenase, as set forth immediately above (and optionally including inactivation of a gene encoding formate transporter), additional genetic modifications are also suitable to the invention, and may serve, for example, to increase amounts of pyruvate that can be harvested. The genetically modified *Enterobacter asburiae* strains may contain, for example, one or more further genetic modifications selected from the group consisting of:

(g) inactivation of a gene encoding acetate kinase; and
(h) inactivation of a gene encoding pyruvate oxidase.

Combinations of these further modifications suitable to the invention include: g; h; and g&h. In one embodiment of the invention, the gene encoding acetate kinase is ackA. In one embodiment of the invention, the gene encoding pyruvate oxidase is poxB.

Additional embodiments relate to *Enterobacter asburiae* strains genetically modified to facilitate production of propanediols. Genetic modifications suitable for this purpose are set forth in U.S. Pat. No. 7,098,009, the disclosure of which is incorporated herein by reference in its entirety. The genetically modified *Enterobacter asburiae* strains may contain, for example, one or more genetic modifications selected from the group consisting of:

(a) incorporation and/or overexpression of a gene encoding glycerol-3-phosphate dehydrogenase;
(b) incorporation and/or overexpression of a gene encoding glycerol-3-phosphatase;
(c) incorporation and/or overexpression of a gene encoding glycerol dehydratase;
(d) incorporation and/or overexpression of a gene encoding 1,3-propanediol oxidoreductase:
(e) incorporation and/or overexpression of a gene encoding aldose reductase; and
(f) incorporation and/or overexpression of a gene encoding glycerol dehydrogenase.

Combinations of these modifications suitable to the invention include: a; b; c; d; e; f; a&b; a&c; a&d; a&e; a&f; b&c; b&d; b&e; b&f; c&d; c&e; c&f; d&e; d&f; e&f; a&b&c; a&b&d; a&b&e; a&b&f; a&c&d; a&c&e; a&c&f; a&d& e; a&d&f; a&e&f; b&c&d; b&c&e; b&c&f; b&d&e; b&d&f; b&e&f; c &d&e; c&d&f; c&e&f; d&e&f; a&b&c&d; a&b&c&e; a&b&c&f; a&b &d&e; a&b&d&f; a&b&e&f; a&c&d&e; a&c&d&f; a&c&e&f; a&d& e&f; b&c&d&e; b&c&d&f; b&c&e&f& b&d&e&f; c&d&e&f; a&b&c &d&e; a&b&c&d&f; a&b&c&c&f; a&b&d&e&f; a&c&d&e&f; b&c &d&e&f; and a&b&c&d&e&f. In one embodiment, *E. coli* host cell W1485 harboring plasmids pDT20 and pAH42 (Accession Number ATCC 98188 and deposited in the ATCC under the terms of the Budapest Treaty) can be used as sources of nucleic acids that encode glycerol-3-phosphate dehydrogenase (G3PDH), glycerol-3-phosphatase (G3P phosphatase), glycerol dehydratase (dhaB), and 1,3-propanediol oxidoreductase (dhaT). In one embodiment, *S. cerevisiae* YPH500 (deposited as ATCC 74392 under the terms of the Budapest Treaty) harboring plasmids pMCK10, pMCK17, pMCK30 and pMCK35 containing genes encoding glycerol-3-phosphate dehydrogenase (G3PDH), glycerol-3-phosphatase (G3P phosphatase), glycerol dehydratase (dhaB), and 1,3-propanediol oxidoreductase (dhaT) can be used as a source of nucleic acid(s) that encode the enzymes. Yet another source of readily available genetic material for the production of recombinant organisms capable of producing 1,3-propanediol is *E. coli* DH5a containing pKP1 which has about 35 kb insert of a *Klebsiella* genome which contains glycerol dehydratase, protein X and proteins 1, 2 and 3 (deposited with the ATCC under the terms of the Budapest Treaty and designated ATCC 69789); *E. coli* DH5a cells containing pKP4 comprising a portion of the *Klebsiella* genome encoding diol dehydratase enzyme, including protein X was deposited with the ATCC under the terms of the Budapest Treaty and was designated ATCC 69790. Preferred enzymes for the production of 1,2-propanediol are aldose reductase, glycerol dehydrogenase, or both. In one embodiment, the gene encoding aldose reductase is the gene for rat lens aldose reductase. In one embodiment, the gene encoding glycerol dehydrogenase is the *E. coli* gene that encodes glycerol dehydrogenase. Aldose reductase sequences are highly conserved, thus the source of the aldose reductase gene is not critical to the present invention. The source of the glycerol dehydrogenase gene also is not critical.

Various aspects of the invention provide the following non-limiting embodiments:

1. A process for fermenting MeGAX comprising:
(a) forming a substrate from biomass materials;
(b) subjecting the substrate to acid hydrolysis;
(c) selecting and isolating a strain of *Enterobacter asburiae* that has the ability to ferment MeGAX;
(d) inoculating the acid hydrolyzed substrate with the selected strain of *Enterobacter* asburiae to ferment MeGAX under conditions favorable for cell viability and conversion of MEGAX to a fermentation product; and
(e) optionally, recovering said fermentation product.

2. The process of embodiment 1, wherein the *Enterobacter asburiae* is the *Enterobacter asburiae* strain JDR-1, E1, or L1.

3. The process of any preceding embodiment, wherein the biomass materials contain hemicellulose.

4. The process of any preceding embodiment, wherein the biomass materials comprise sweetgum.

5. The process of any preceding embodiment, wherein the acid hydrolysis is dilute acid hydrolysis.

6. A process for fermenting MeGAX comprising:
(a) selecting and/or isolating a strain of *Enterobacter asburiae* that has the ability to ferment MeGAX;

(b) inoculating culture media comprising MeGAX with the selected strain of *Enterobacter* asburiae to ferment MeGAX under conditions favorable for cell viability and conversion of MEGAX to a fermentation product; and (e) optionally, recovering fermentation product from the substrate.

7. The process of embodiment 6, wherein the *Enterobacter asburiae* is the *Enterobacter asburiae* strain JDR-1, E1, or L1.

8. The process of any embodiments 6-7, wherein the culture media contains hemicellulose.

9. The process of embodiments 6-8, wherein the culture media comprises sweetgum or other biomass.

10. The process according to embodiments 6-9, wherein said fermentation product is acetate/acetic acid; ethanol; methanol; succinate/succinic acid; lactate/lactic acid; formate/formic acid; acetate/acetic acid; 2,3-butanediol; or combinations thereof 11. A process for fermenting a substrate comprising:
(a) selecting and isolating a strain of *Enterobacter asburiae* that has the ability to ferment a substrate;
(b) inoculating culture media comprising said substrate with the selected strain of *Enterobacter asburiae* and fermenting said substrate under conditions favorable for cell viability and conversion of the substrate to a fermentation product; and
(e) optionally, recovering fermentation product from the substrate.

12. The process of embodiment 11, wherein the *Enterobacter asburiae* is the *Enterobacter asburiae* strain JDR-1, E1, or L1.

13. The process of embodiments 11-12, wherein said fermentation product acetate/acetic acid; ethanol; methanol; succinate/succinic acid; lactate/lactic acid; formate/formic acid; acetate/acetic acid; 2,3-butanediol; or combinations thereof 14. The process of embodiments 11-13, wherein said substrate is D-glucose, D-xylose, D-mannose, L-arabinose, D-galactose, glucuronate, or various combinations thereof.

15. An isolated strain of *Enterobacter asburiae*.

16. The isolated *E. asburiae* strain according to embodiment 15, wherein said strain is selected from the group consisting of JDR-1, E1, and L1.

17. The isolated *E. asburiae* strain of embodiments 15-16, wherein said strain comprises one or more genetic modifications selected from the group consisting of:
incorporation and/or overexpression of a gene encoding CRP*;
incorporation and/or overexpression of a gene encoding xylose reductase;
incorporation and/or overexpression of a gene encoding xylitol dehydrogenase; and
inactivation of a gene encoding xylulokinase.

18. The isolated *E. asburiae* strain of embodiments 15-17, wherein said strain comprises one or more genetic modifications selected from the group consisting of:
incorporation and/or overexpression and/or inactivation of a gene encoding L-lactate dehydrogenase;
incorporation and/or overexpression and/or inactivation of a gene encoding D-lactate dehydrogenase;
inactivation of a gene encoding fumarate reductase (frd);
inactivation of a gene encoding alcohol/aldehyde dehydrogenase (adh);
inactivation of a gene encoding pyruvate formate lyase (pfl);
inactivation of a gene encoding acetate kinase (ack); and
inactivation of a gene encoding methylglyoxal synthase (mgs).

19. The isolated *E. asburiae* strain of embodiments 15-18, wherein said strain comprises one or more genetic modifications selected from the group consisting of:
insertion and/or overexpression of a gene encoding pyruvate decarboxylase;
insertion and/or overexpression of a gene encoding alcohol dehydrogenase;
inactivation of a gene encoding lactate dehydrogenase;
inactivation of a gene encoding phosphoenolpyruvate carboxylase; inactivation of a gene encoding acetate kinase; and
inactivation of a gene encoding pyruvate formate lyase.

20. The isolated *E. asburiae* strain of embodiments 15-19, wherein said strain comprises one or more genetic modifications selected from the group consisting of:
overexpression of a gene encoding PEP carboxykinase;
inactivation of a gene encoding pyruvate formate lyase; and
inactivation of a PEP-dependent phosphotransferase system gene.

21. The isolated *E. asburiae* strain of embodiments 15-20, wherein said strain comprises one or more further genetic modifications selected from the group consisting of:
inactivation of a gene encoding acetate kinase;
inactivation of a gene encoding alcohol dehydrogenase;
inactivation of a gene encoding aspartate aminotransferase;
inactivation of a gene encoding citrate lyase;
inactivation of a gene encoding lactate dehydrogenase;
inactivation of a gene encoding methylglyoxal synthase;
inactivation of a gene encoding pyruvate oxidase;
inactivation of a gene encoding phosphate acetyltransferase;
inactivation of a gene encoding malic enzyme; and
inactivation of a gene encoding threonine dehydratase.

22. The isolated. *E. asburiae* strain of embodiments 15-21, wherein said strain comprises one or more genetic modifications selected from the group consisting of:
incorporation and/or overexpression of a gene encoding alanine dehydrogenase;
inactivation of a gene encoding alanine racemase;
inactivation of a gene encoding lactate dehydrogenase;
inactivation of a gene encoding alcohol dehydrogenase;
inactivation of a gene encoding fumarate reductase;
inactivation of a gene encoding pyruvate formate lyase;
inactivation of a gene encoding acetate kinase; and
inactivation of a gene encoding methylglyoxal synthase.

23. The isolated *E. asburiae* strain of embodiments 15-22, wherein said strain comprises one or more genetic modifications selected from the group consisting of:
incorporation and/or overexpression of a gene encoding cellobiose utilizing enzyme;
incorporation and/or overexpression of a gene encoding phospho-β-glucosidase; and
incorporation and/or overexpression of a gene encoding an endoglucanase or cellulase.

24. The isolated *E. asburiae* strain of embodiments 15-23, wherein said strain comprises one or more genetic modifications selected from the group consisting of:
inactivation of a gene encoding lactate dehydrogenase;
inactivation of a gene encoding pyruvate formatelyase;
inactivation of a gene encoding fumarate reductase;
inactivation of a gene encoding $(F_1F_0)H^+$-ATP synthase;
inactivation of a gene encoding alcohol/aldehyde dehydrogenase; and
inactivation of a gene encoding 2-ketoglutarate dehydrogenase.

25. The isolated *E. asburiae* strain of embodiments 15-24, wherein said strain comprises one or more further genetic modifications selected from the group consisting of:
   inactivation of a gene encoding acetate kinase; and
   inactivation of a gene encoding pyruvate oxidase.

26. The isolated *E. asburiae* strain of embodiments 15-25, wherein said strain comprises one or more genetic modifications selected from the group consisting of:
   incorporation and/or overexpression of a gene encoding glycerol-3-phosphate dehydrogenase;
   incorporation and/or overexpression of a gene encoding glycerol-3-phosphatase;
   incorporation and/or overexpression of a gene encoding glycerol dehydratase;
   incorporation and/or overexpression of a gene encoding 1,3-propanediol oxidoreductase;
   incorporation and/or overexpression of a gene encoding aldose reductase; and
   incorporation and/or overexpression of a gene encoding glycerol dehydrogenase.

27. The isolated *E. asburiae* strain of embodiments 15-26, wherein said strain comprises one or more genetic modifications selected from the group consisting of:
   inactivation of a gene encoding pyruvate foi mate lyase; and
   inactivation of a gene encoding acetolactate synthase.

28. The process according to embodiments 1-14, wherein said biomass comprises sweetgum, wood preprocessed for cellulose production, rice straw, wood prunings, wood, wood waste, newspaper, paper products, plant materials and/or tree cuttings, miscanthus, switchgrass, elephant grass, energy cane, hemp, corn, *Eucalyptus* spp., poplar, yellow poplar, cottonwood, willow, sorghum, sugarcane, sugarcane bagasse, corn stalks, corn stover, wheat straw and combinations thereof.

Following are examples that illustrate procedures for practicing the invention. These examples should not be construed as limiting. All percentages are by weight and all solvent mixture proportions are by volume unless otherwise noted.

Example 1

Strain Isolation and Characterization

Preparation of Substrates and Culture Media

Sweetgum methylglucuronoxylan (MeGAX$_n$) was prepared from sweetgum stem wood (*Liquidambar styraciflua*) as previously described and characterized by $^{13}$C-NMR (Hurlbert & Preston *J Bacterial* 183:2093-2100 (2001); Kardosova et al. *Carbohydr Res* 308:99-105 (1998)). Dilute acid hydrolysates of methylglucuronoxylan were prepared by hydrolysis with 0.1 N H$_2$SO$_4$ (4 g methylglucuronoxylan in 400 ml 0.1 NH$_2$SO$_4$) at 121° C. for 60 min, followed by neutralization with BaCO$_3$. Anion exchange resin (Bio-Rad AG2-X8) in the acetate form was used to adsorb the charged aldouronates; the uncharged xylose and xylooligosaccharides, mainly small amounts of xylobiose, were eluted with water. The aldouronates were then eluted with 20% (v/v) acetic acid. After concentration under vacuum at 50° C., aldouronates were separated on a 2.5 cm×160 cm BioGel P-2 column (BioRad, Hercules, Calif.) with 50 mM formic acid as the eluent. The formic acid was removed from the purified sugar sample fractions by lyophilization. MeGAX and MeGAX$_2$ were identified by thin layer chromatography (TLC) analysis using MeGAX and MeGAX$_2$ standards structurally defined by $^{13}$C and $^1$H-NMR spectrometry (Zuobi-Hasona et al. *ASM National Meeting* (2001)). Xylobiose and xylotriose were obtained and purified from MeGAX$_n$ digested with *Paenibacillus* sp. strain JDR-2 XynA$_1$ catalytic domain (CD), a recombinant GH10 endoxylanase XynA$_1$ CD overexpressed in *E. coli* (St. John et al. *Appl Environ Microbiol* 72:1496-1506 (2006)). The substrate containing 30 mg/ml MeGAX$_n$ was prepared with 10 mM sodium phosphate buffer, pH 6.5. Digestions were initiated by the addition of 3.5 U of XynA$_1$ CD into 50 ml substrate and incubated with rocking at 30° C. for 24 h. An additional 1 U was added after 24 h and incubation was continued for 40 h. Aldouronates, xylobiose, and xylotriose were separated with the P2 column and identified by TLC. Total carbohydrate concentrations related to substrate preparations were determined by the phenol-sulfuric acid assay (Dubois et al. *Anal Chem* 28:350-356 (1956)), with xylose as the reference. The conditions of acid hydrolysis generated mostly MeGAX and a small amount of MeGAX$_2$ from MeGAX$_n$, with no aldouronates larger than MeGAX$_2$ detected. MeGAX$_3$ was prepared from GH10 endoxylanase-catalyzed depolymerization of sweetgum MeGAX$_n$ and then purified by gel filtration on BioGel P4 (St. John et al. *Appl Environ Microbial* 72:1496-1506 (2006)).

Minimal medium containing the substrates described above was prepared upon mixing sterile substrate solutions (2× concentration) with the same volume of a 2× solution of Zucker and Hankin mineral salts (ZH salts) at pH 7.4 (Zucker & Hankin *J Bacterial* 104:13-18 (1970)). Neutralized MeGAX$_n$ acid hydrolysate (0.5% w/v) was also added to ZH salts directly as a growth substrate. Where indicated, some media preparations were supplemented with 0.1% yeast extract (YE medium).

Isolation and Identification of *E. asburiae* JDR-1

*E. asburiae* JDR-1 was isolated from discs of sweetgum stem wood (*Liquidambar styraciflua*) buried, soon after cutting, about one inch below the soil surface in a sweetgum stand for approximately three weeks. Discs were suspended in 50 ml sterile deionized water and sonicated in a 125 Watt Branson Ultrasonic Cleaner water bath for 10 min. The sonicate was inoculated into 0.2% (w/v) MeGAX YE medium and incubated at 37° C. Cultures were streaked on MeGAX minimal medium agar plates. Isolated colonies were passed several times between MeGAX broths and agars until pure. Exponential phase cultures growing on 0.2% MeGAX minimal media were cryostored in 25% sterile glycerol at −70° C.

The purified isolate was submitted to MIDI Labs (world wide web site: midilabs.com) for partial 16s rRNA sequencing and FAME analysis. BBL Enterotube™ II (Becton, Dickinson and Company, USA) inoculation was also used to identify the isolate based upon metabolic capability using the standard protocol. Differential Interference Contrast (DIC) micrographs of *E. asburiae* JDR-1 growing in MeGAX minimal medium at exponential phase were obtained with a Zeiss DIC microscope at 40×15-fold magnification. Negative stain electron micrographs were obtained with a Zeiss EM10A electron microscope.

Substrate Utilization and Fermentation Product Analysis

Growth and substrate utilization analysis was performed in cultures aerated by shaking. For preparing inocula, cultures of *E. coli* B (ATCC 11303) and *E. asburiae* JDR-1 from cryostored samples were directly streaked on Luria-Bertani (LB) agar plates. After overnight incubation at 37° C., isolated colonies were picked to inoculate liquid media specified for a particular experiment. Growth studies were performed at 37° C. in 16 mm×100 mm test tubes containing 6 ml medium. Optical densities of cultures were measured at 600 nm (OD$_{600}$) with a Beckman DU500 series spectrophotometer. The relationship of cell density and OD$_{600}$ was experimentally determined as CDW/L (g cell dry weight/L)

=0.49OD$_{600}$+0.02. Sample dilutions were made to obtain OD$_{600}$ readings between 0.2 and 0.8 absorbance units which, corrected for dilution factors, provided turbidity values for growth studies. Individual 6 ml cultures for study were inoculated with 12 µl (0.2% volume) of overnight cultures and maintained at 37° C. with constant shaking (Eberbach shaker set at "low").

Batch fermentations under anaerobic conditions at 37° C. were conducted in 13 mm×100 mm screw cap tubes containing 3.0 ml medium. Inocula (0.5% [v/v]) were from overnight aerobic cultures grown in the same medium. After inoculation, nitrogen gas was used to flush and saturate the sealed batch culture. The tubes were set in a Glas-Col minirotator at 60 rpm.

For analysis of substrates and fermentation products, cells were removed by centrifugation and supernatants were passed through 0.22 um filters and subjected to HPLC analysis. Products were resolved on a Bio-Rad HPX-87H column with 0.01 N H$_2$SO$_4$ as the eluent at 65° C. Samples were delivered with a 710B WISP automated injector and chromatography controlled with a Waters 610 solvent delivery system at flow rate of 0.5 ml/min. Products were detected by differential refractometry with a Waters 2410 RI detector. Data analysis was performed with Waters Millennium Software. To determine and quantify methanol, unfiltered supernatants from fermentation cultures were also analyzed by gas chromatography (6890N Network GC system, Agilent Technologies), using isopropanol as an internal standard. This detection method was used since diffusion during HPLC precluded quantitative detection of methanol by differential refractometry.

Determination of Metabolic Pathways by $^{13}$C-NMR

The central metabolic pathways utilized by *E. asburiae* JDR-1 during glucose and xylose fermentation were evaluated with $^{13}$C-NMR (Scott & Baxter *Annu Rev Biophys Bioeng* 10:151-174 (1981)). Cultures were grown in LB medium to mid-exponential phase at 37° C. Cultures (0.5 ml) were centrifuged and the cells washed with 2×ZH salts solution. The cell pellets were suspended in 1.0 ml 0.5% [2-$^{13}$C] xylose (99% enrichment; Omicron Biochemicals Inc, IN) in ZH minimal medium. Similar fermentations were also prepared with 1.0 ml 0.5% [1-$^{13}$C]glucose, or 1.0 ml 0.5% [6-$^{13}$C]glucose ZH minimal medium using D-[1-$^{13}$C]glucose or D[6-$^{13}$C]glucose (99% enrichment; Cambridge Isotope Laboratories, Andover, Mass.). Fermentations were carried out under anaerobic conditions at 37° C. for 8 hours. Cells were removed by centrifugation, and the supernatants analyzed by HPLC (after filtration) and $^{13}$C-NMR spectrometry. NMR spectra were obtained using a VXR300 NMR spectrometer (NMR facility of the Department of Chemistry, University of Florida) operating in the Fourier transform mode as follows: 75.46 MHz; excitation pulse width, 7.0 s; spectral width, 16502; 256 acquisitions. Acetone (30 µl) containing $^{13}$C at natural abundance in 700 µl sample was used as an internal reference of 31.07 ppm for the $^{13}$C methyl carbon (Kardosova et al. *Carbohydr Res* 308:99-105 (1998)). Individual carbon atoms for fermentation products were identified by shift assignments and quantified by comparison with standards ($^{13}$C at natural abundance) of known concentrations.

Determination of Molar Cell Dry Weight Yield

For molar growth yield experiments (Smalley et al. *J Bacteriol* 96:1595-1600 (1968); Bauchop & Elsden *J Gen Microbiol* 23:457-469 (1960); Gunsalus & Shuster in *The Bacteria* (1961)), anaerobic growth was performed in 50 ml minimal medium containing either 0.26% glucose, 0.36% xylose, 0.35% glucuronate and 0.2% MeGAX as sole carbon sources with the fermentation conditions described above. After 24 hours of growth and complete utilization of the carbon source, cells were harvested by centrifugation and the resulting pellets were washed twice with deionized water. The pellets were dried to constant weight in a Sargent vacuum dryer at 60° C. for up to 36 hours. The culture supernatants were analyzed by HPLC to determine substrate consumption. The molar cell dry weight yield was calculated as cell dry weight (gram) divided by consumed substrate (mole).

Results

Identification and Characteristics of *E. asburiae* JDR-1

A novel bacterial strain able to grow on MeGAX minimal medium was obtained and subsequently identified with three tests. The partial 16S rRNA sequence (accession number EU117142, Gene Bank, NCBI), amplified using primers corresponding to *E. coli* 16S rRNA positions 005 and 531 (526 bp), provided an alignment with 99.5% identity within the sequence of *Enterobacter asburiae* (MIDI Aerobic Bacteria Database version 4.0, January 1999). Results of FAME (fatty acid methyl ester) analysis indicated this strain had the greatest similarity index with *Enterobacter asburiae* species (0.766) compared with any other entry in the MIDI database. A biocode of 32061, obtained from the Enterotube II (BBL) test, also corresponded to *Enterobacter asburiae* species. Based upon these three criteria, the isolate was identified within *Enterobacter asburiae* species and designated as *Enterobacter* asburiae strain JDR-1. The strain has been deposited with the Agriculture Research Service Patent Culture Collection of the USDA, Peoria, Ill., under NRRL number NRRL B-S0074.

When exponential phase cultures were observed by optical DIC microscopy, *E. asburiae* JDR-1 appeared as short motile rods. Negative stain electron microscopy revealed 3 µm×1 µm cells with peritrichous flagella. These morphological characteristics were similar to those of other isolates of *Enterobacter asburiae* (Hoffman et al. *Syst Appl Microbiol* 28:196-205 (2005)). When grown on LB agar plates, colonies of *E. asburiae* JDR-1 were morphologically indistinguishable from *E. coli* colonies.

Utilization of Acid Hydrolysates of Methylgluronoxylan by *E. asburiae* JDR-1

Figure 2A:
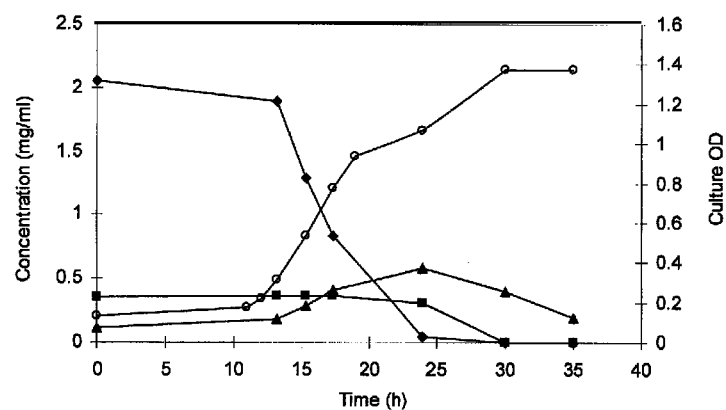
FIGS. 2A-2B: Aerobic growth, substrate utilization, and formation of products from acid hydrolysates of MeGAX$_n$ by A) *E. asburiae* JDR-1 and B) *E. coli* B. Xylose (diamonds), MeGAX (squares), and acetic acid (triangles) were determined in media by HPLC. Growth was determined by measuring turbidity as $OD_{600}$ (open circles).
Figure 2B:
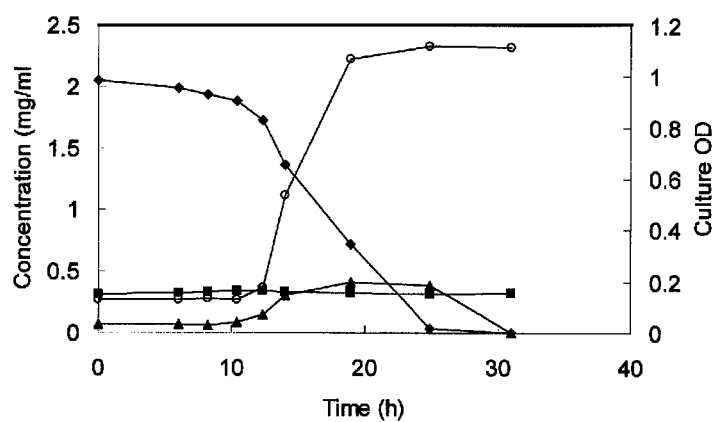

The unique ability of *E. asburiae* JDR-1 to grow on the aldobiuronate MeGAX as the sole carbon source suggested a potential for the complete metabolism of the carbohydrates generated by the dilute acid pretreatment currently applied for the release and fermentation of xylose in hemicellulose fractions. To evaluate this potential, *E. asburiae* JDR-1 was grown aerobically in minimal medium comprised of neutralized MeGAX$_n$ acid hydrolysate and Zucker and Hankin mineral salts. Based upon HPLC analysis of media samples taken at different stages of growth, *E. asburiae* JDR-1 utilized MeGAX completely in minimal media containing MeGAX hydrolysate after it depleted xylose (FIG. 2A). Biphasic growth occurred as *E. asburiae* JDR-1 switched from utilizing xylose to MeGAX (FIG. 2B). In contrast to *E. asburiae* JDR-1, *E. coli* B consumed only the free xylose with the MeGAX concentration in the medium remaining constant. Concentrations of xylose and MeGAX in MeGAX$_n$ hydrolysate medium, as determined by HPLC, were 0.206% w/v and 0.036% w/v, respectively. Therefore, *E. asburiae* JDR-1 utilized 17.5% more substrate (mass amount) than *E. coli* B, which was unable to utilize MeGAX (FIG. 2B). Under aerobic conditions, both *E. asburiae* JDR-1 and *E. coli* B formed acetic acid during exponential growth phase that was metabolized upon complete utilization of the carbon sources in the MeGAX hydrolysates. *E. asburiae* JDR-1 was also able to grow in xylobiose and xylotriose minimal medium, which *E.*

*coli* B could not utilize. However, *E. asburiae* JDR-1 was unable to utilize MeGAX$_2$ and MeGAX$_3$ (data not shown).

Substrate Preference of *E. asburiae* JDR-1

Figure 3A:
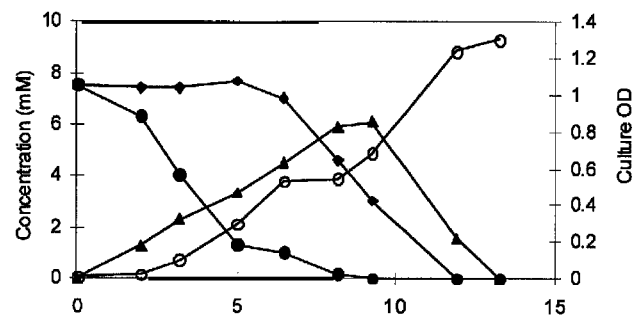
FIGS. 3A-3C: Aerobic growth of *E. asburiae* JDR-1 on different combinations of sugar substrates. Concentrations of substrates and acetic acid as a product were determined by HPLC. Growth was determined as turbidity ($OD_{600}$). A) Growth on glucose (7.5 mM) and xylose (7.5 mM). Concentrations of glucose (closed circles), xylose (diamonds) and acetic acid (triangles); $OD_{600}$ (open circles); B) Growth on glucuronic acid (10 mM) and xylose (10.5 mM). Concentrations of glucuronic acid (open squares) and xylose (diamonds); ($OD_{600}$ (open circles) C) Growth on MeGAX (6.5 mM). Concentrations of McGAX (squares): $OD_{600}$ (open circles).

*E. asburiae* JDR-1 was found to grow aerobically in minimal media containing different sole carbon sources, such as glucose, xylose, mannitol, maltose, rhamnose, mannose, glucuronate and glycerol. As noted above, it was able to quantitatively metabolize MeGAX, but was unable to utilize MeGAX$_2$ generated by acid hydrolysis, or MeGAX$_3$ generated by a GH10 endoxylanase. When growing in a minimal medium containing an eqimolar mixture of glucose and xylose, *E. asburiae* JDR-1 displayed a diauxic growth pattern typical of species of Enterobacteraceae (FIG. 3A). Glucose (8 mM) was consumed within approximately 8 hours, while xylose utilization began when glucose was almost entirely consumed and was depleted in 14 hours.

Figure 3B:
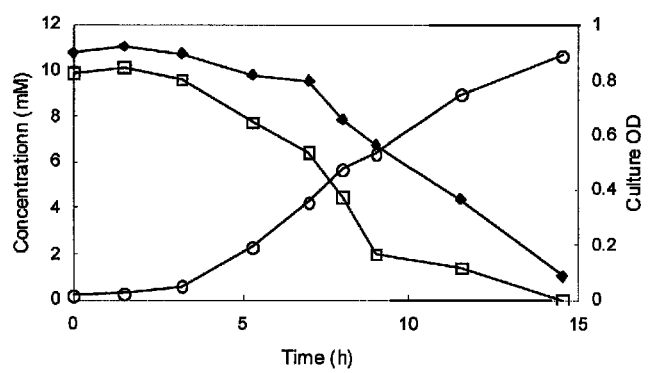
Figure 3C:
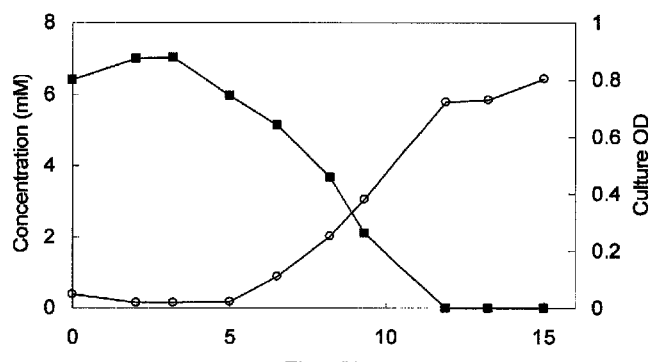

To study the process by which McGAX was utilized, *E. asburiae* JDR-1 was grown in minimal medium containing both xylose and glucuronate, products that might be generated from MeGAX. A single phase growth curve was observed in which both substrates were consumed by 15 hours (FIG. 3B). This is similar to its single phase growth curve on MeGAX, in which the 6.5 mM substrate was depleted in about 11 hours (FIG. 3C). The similarity in growth pattern with MeGAX and the combination of xylose and glucuronate as carbon sources supports the possibility that free glucuronate and free xylose may be released during the metabolism of MeGAX.

Fermentation Characteristics

Fermentation experiments were performed to evaluate the potential of *E. asburiae* JDR-1 as a biocatalyst for the production of biobased products, and define the processes involved in the metabolism of MeGAX. Using limiting amounts (0.25% w/v) of substrates and cultivation under anaerobic standing conditions, *E. asburiae* JDR-1 was able to ferment all major sugars constituting hemicellulose, including D-glucose, D-xylose, D-mannose, L-arabinose and D-galactose. The major products from xylose and galactose fermentation were acetic acid and ethanol present in similar molar quantities. Acetic acid, ethanol and small amounts of lactic acid were produced from glucose, mannose and arabinose (Table 1). Small amounts of formic acid and very small amounts of fumaric and succinic acids were detected in most fermentations. The HPLC profiles indicate that *E. asburiae* JDR-1 performs mixed acid fermentation as does *E. coli*, but with preferential formation of acetate and ethanol over lactate.

With sweetgum MeGAX$_n$ hydrolysate as substrate, *E. asburiae* JDR-1 consumed 99% of the substrate when the pH was maintained above 5, giving the major products acetic acid and ethanol (Table 2). With glucuronic acid as carbon source, acetic acid was the major fermentation product. To study the process of MeGAX metabolism, the presumed degradation products of MeGAX, xylose and glucuronate, both at 11 mM, were used as substrates. The predominant products were 20.4 mM acetate and 5.25 mM ethanol. Major fermentation products from 4.0 mM MeGAX were 8.1 mM acetic acid, 1.2 mM ethanol, and 4.3 mM methanol (Table 2).

Central Metabolic Pathways Determined by $^{13}$C-NMR

The total quantities of ethanol, acetate and lactate were determined by HPLC and the quantities of $^{13}$C labeled products were quantified from integration of differentially labeled compounds detected in the $^{13}$C-NMR spectra. This allowed determination of the fraction of each fermentation product that was differentially labeled with $^{13}$C, which helped to illustrate the central metabolic pathways *E. asburiae* JDR-1 uses. The quantities of each product and the fractions labeled with $^{13}$C are presented in Table 3.

To determine the primary pathway of xylose metabolism by *E. asburiae* JDR-1, comparisons were made for the fermentation of [2-$^{13}$C]xylose with cultures of *E. coli* B. For *E. coli* B, employing only the pentose-phosphate pathway to metabolize xylose, the prominent shift signals in the $^{13}$C-NMR spectrum of the fermentation products were assigned to [1-$^{13}$C]ethanol at 57.6 ppm, [2-$^{13}$C]lactate at 68.8 ppm, and [1-$^{13}$C]acetate at 181.0 ppm. Shift signals at 71.0 ppm and 74.5 ppm were assigned to the α- and β-anomers of unused [2-$^{13}$C]xylose, and the signal at 30.6 ppm to the methyl carbons of the acetone standard (FIG. 4B). Fractions of labeled versus total acetate, ethanol, and lactate with *E. coli* B were 0.26, 0.27, and 0.31, respectively, which was slightly less than the theoretical fraction 0.4 expected for metabolism through the pentose-phosphate pathway (Table 3). The lower quantities of labeled products as fractions of the total found for *E. coli* may reflect accuracy limitations for integration against the $^{13}$C-acetone standard, as these products all showed similar fractions (0.26-0.31) were labeled.

Figure 4A:
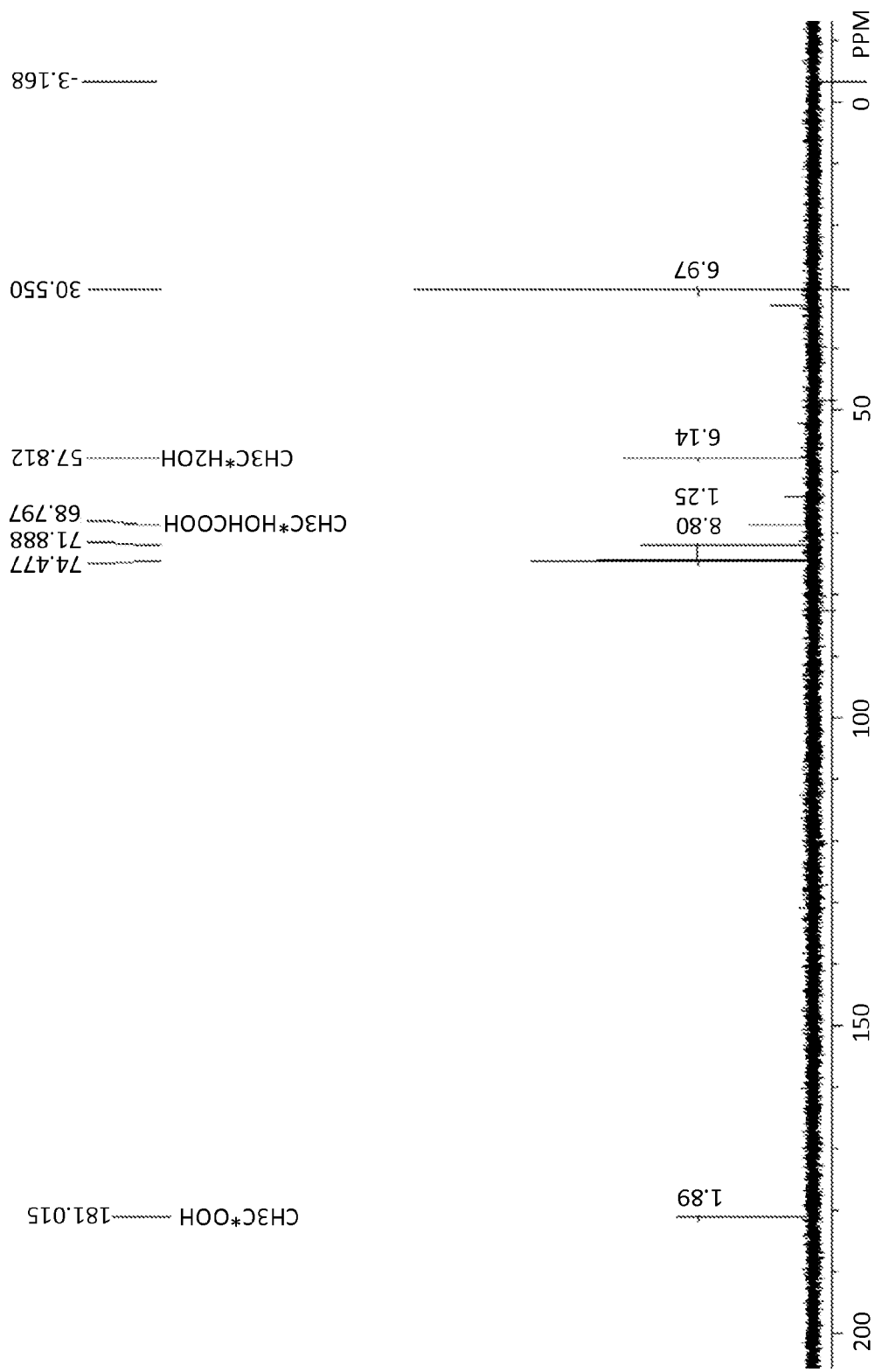
FIGS. 4A-4D: Pathway determination for the metabolism of xylose and glucose by *E. asburiae* JDR-1. Media from anaerobic cultures of *E. asburiae* JDR-1 and *E. coli* B grown with xylose or glucose enriched with $^{13}C$ in specific carbons were analyzed by 75.5 MHz $^{13}C$-NMR spectrometry. A) [2-$^{13}C$]-xylose fermented by *E. asburiae* JDR-1; B) [2-$^{13}C$]-xylose fermented by *E. coli* B; C) [1-$^{13}C$]-glucose fermented by *E. asburiae* JDR-1; D) [6-$^{13}C$]-glucose fermented by *E. asburiae* JDR-1.
Figure 4B:
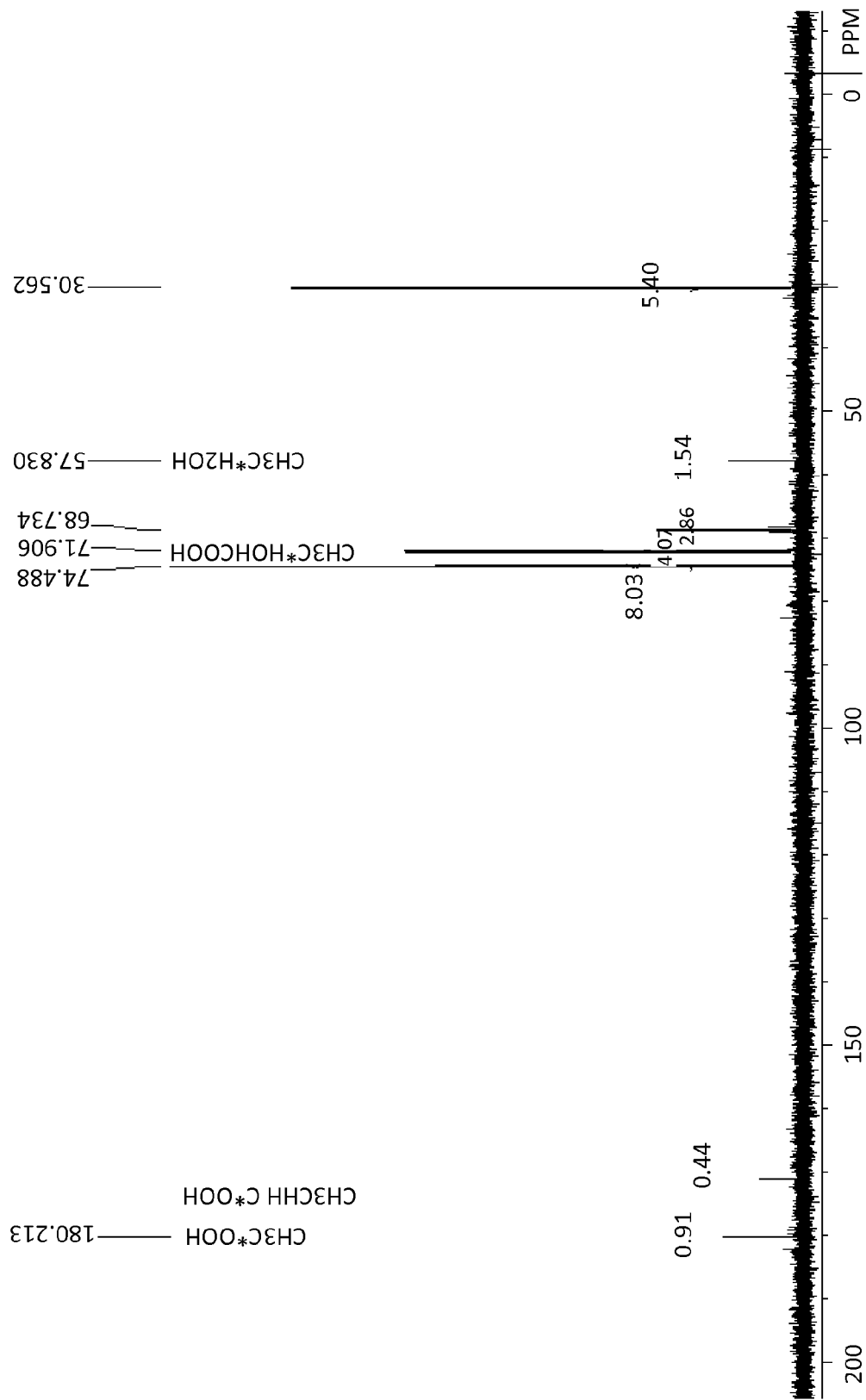

When *E. asburiae* JDR-1 fermented [2-$^{13}$C]xylose, a $^{13}$C-NMR spectrum for fermentation products was obtained with prominent signals for [1-$^{13}$C]ethanol, [2-$^{13}$C]lactate, and [1-$^{13}$C]acetate at expected shift positions of 57.8 ppm, 68.8 ppm and 181.0 ppm respectively (FIG. 4A). The fractions of labeled ethanol, labeled acetate and labeled lactate to their total amounts were 0.43, 0.4 and 0.45, respectively (Table 3), and nearly identical to the theoretical fraction of 0.4. Moreover, the fractions of labeled acetate and ethanol were not higher than the fraction of labeled lactate (Table 3). These results establish that the pentose phosphate pathway is the main metabolic pathway for xylose utilization in *E. asburiae* JDR-1.

Figure 4C:
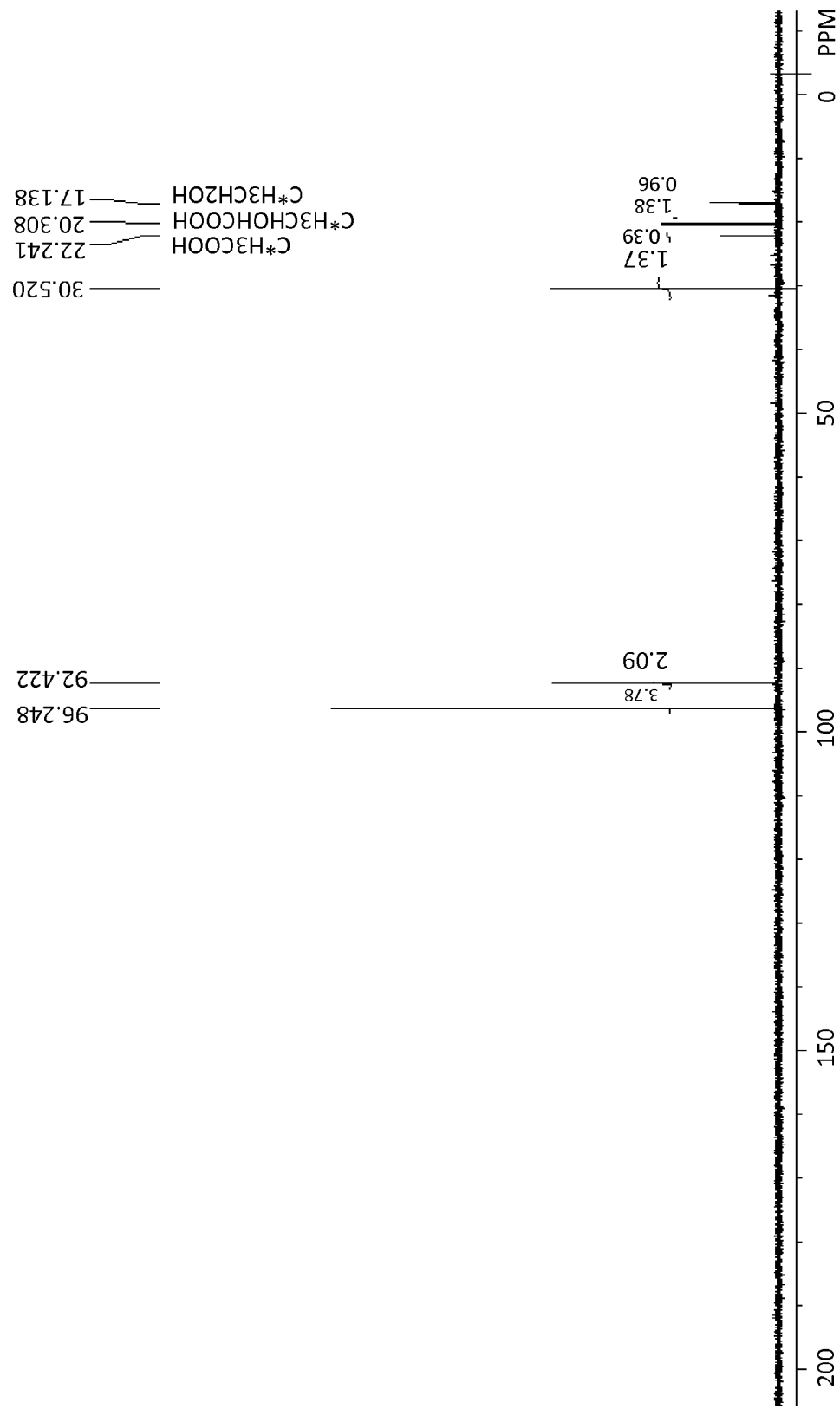
Figure 4D:
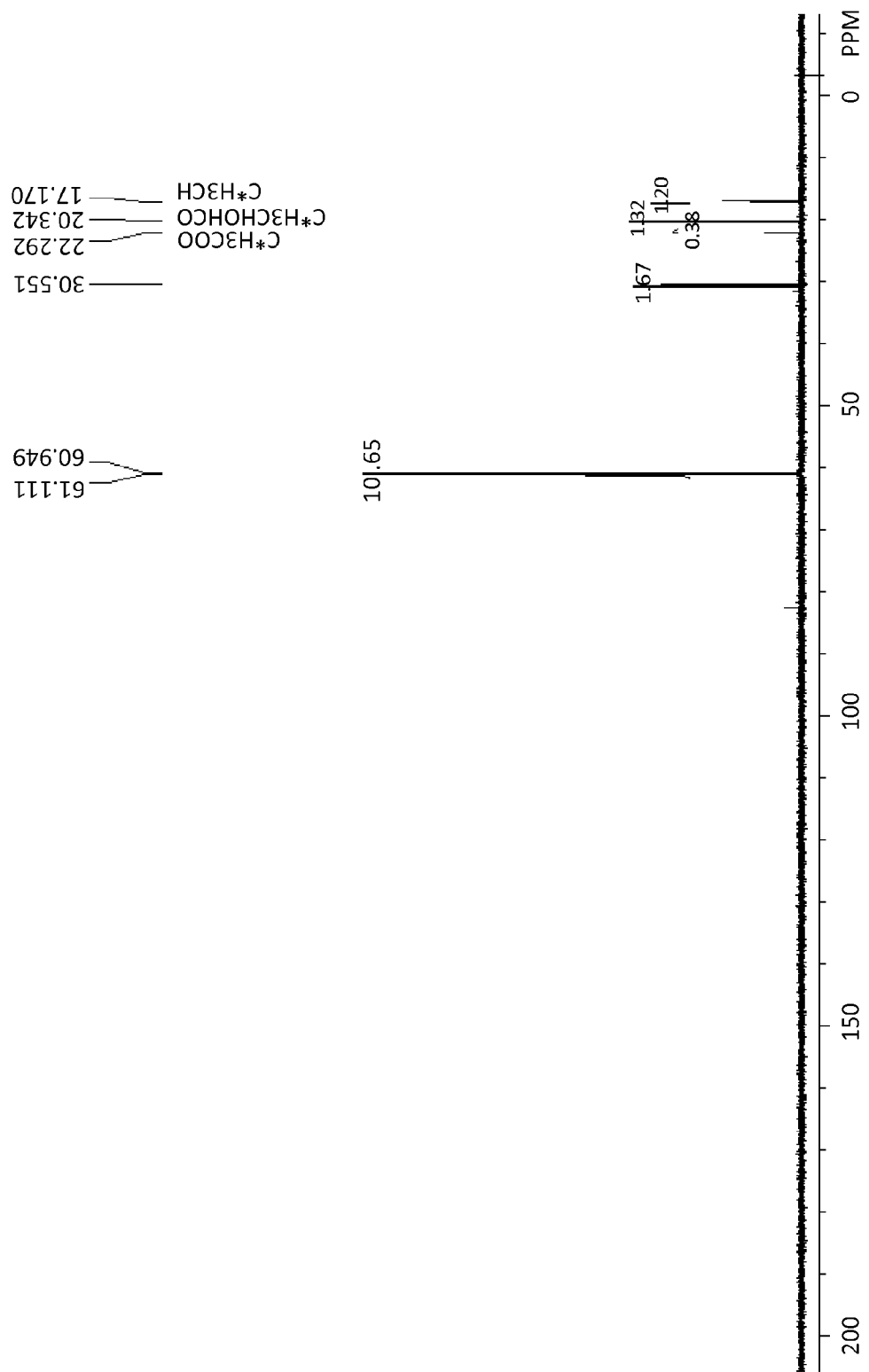

To determine the primary pathway *E. asburiae* JDR-1 utilizes to metabolize glucose, [1-$^{13}$C]glucose and [6-$^{13}$C]glucose were used as fermentation substrates. Similar $^{13}$C-NMR spectra of fermentation products were obtained from [6-$^{13}$C]glucose and [1-$^{13}$C]glucose (FIG. 4C, 4D). Shift signals at 92.4 and 96.2 ppm were assigned to the α- and β-anomers of unused [1-$^{13}$C]glucose (FIG. 4C); signals at 60.9 and 60.1 ppm were assigned to the α- and β-anomers of unused [6-$^{13}$C]glucose (FIG. 4D). The signal at 30.6 ppm was assigned to the methyl carbons of the acetone standard. Excepting the shift signals for reference and unused substrates, the prominent signals in both spectra were for [2-$^{13}$C]ethanol at 17.1 ppm, [2-$^{13}$C]acetate at 22.2 ppm and [3-$^{13}$C]lactate at 20.3 ppm with similar distributions for both substrates. The absence of [1-$^{13}$C]lactate indicates that no [1-$^{13}$C]glucose was metabolized through the Entner-Douderoff (ED) pathway. Moreover, the fractions of all labeled products of their total amounts were similar for fermentation of [6-$^{13}$C]glucose and [1-$^{13}$C]glucose; and these fractions for [6-$^{13}$C]glucose were not higher than those found for [1-$^{13}$C]glucose (Table 3), indicating little or no [1-$^{13}$C]glucose went through the pentose-phosphate pathway. Collectively, these results establish that the Embden-Meyerhof (EM) pathway is the main metabolic pathway for glucose utilization in *E. asburiae* JDR-1.

Growth and Projected ATP Yields with Different Substrates

To understand the bioenergetics in the process of MeGAX fermentation by *E. asburiae* JDR-1, molar cell dry weight yields were determined after 24 hours of growth with glucose, xylose, glucuronate and MeGAX as sole carbon sources in Zucker-Hankin minimal medium. The experiment was performed three times and the average approximate $Y_M$ values were about 10 g per mole of substrate for growth on xylose and glucuronate, 20 for growth on glucose, and 30 for growth on MeGAX (Table 4). The experimental $Y_{ATP}$ in anaerobic growth has been reported in the range of 8 to 12 gram cell dry weight per mole of ATP for bacteria (Russell & Cook Microbiol Rev 59:48-62 (1995)). An estimated $Y_{ATP}$ value at the lower end of this range, 8, was used here since this is for anaerobic growth in batch cultures in minimal medium with a relatively low concentration of carbon source (Bauchop & Elsden *J Gen Microbiol* 23:457-469 (1960); Gunsalus & Shuster in *The Bacteria* (1961)). The apparent ATP yields per mole of substrate were calculated based on the estimated $Y_{ATP}$ of 8 as 1.3 mole of ATP produced from either xylose or glucuronate, 2.6 from glucose and 4.0 from MeGAX (Table 4). These apparent ATP yields allow an estimate of the relative ATP yields obtained for the different substrates without considerations of maintenance energy or overflow metabolism (Russell & Cook *Microbiol Rev* 59:48-62 (1995)), providing insight into the metabolism of MeGAX. The ratios of the molar growth yields obtained with xylose, glucuronate, and MeGAX as carbon sources are 1.0:1.0:3.2 (Table 4), indicating that the requirement for MeGAX transport is less than that for separate transport of xylose and glucuronate.

Example 2

Genetic Engineering for Lactic Acid Production

Bacterial Strains, Media, and Fermentation Conditions

The bacterial strains constructed and used in these studies are listed in Table 5. The *E. asburiae* JDR-1 served as a starting point for genetic modification.

Sweetgum methylglucuronoxylan ($MeGAX_n$) was prepared from sweetgum stem wood (*Liquidambar styraciflua*) as previously described and characterized by $C^{13}$-NMR (Hurlbert and Preston 2001; Kardosova et al. 1998). Dilute acid hydrolysates of methyglucuronoxylan were prepared by acid hydrolysis of 1% sweetgum xylan with 0.05 M $H_2SO_4$ at 121° C. for 60 min, followed by neutralization with $BaCO_3$. Total carbohydrate concentrations of substrate preparations were determined by the phenol-sulfuric acid assay (Dubois et al. 1956) with xylose as reference or by HPLC as previously described (Bi et al. 2009). Fermentation media were supplemented with Zucker and Hankin mineral salts (ZH salts) at pH 7.4 (Zucker and Hankin 1970) or LB broth. The media were buffered with 100 mM sodium phosphate buffer (pH 7.0) or 100 mM 3-(N-morpholino) propane sulfonic acid (MOPS) buffer (pH 7.0) when necessary. Batch fermentations were carried out in medium saturated with nitrogen in tubes set in a Glas-Col minirotator at 60 rpm in a 30° C. incubator. Fermentations were inoculated to an initial optical density at 600 nm of 0.8. Fermentation products were resolved on a Bio-Rad HPX-87H column with a Waters HPLC system or an Agilent HPLC system.

Genetic Methods

Standard methods were used for most of the genetic manipulations. Qiagen kits were used for genomic DNA and plasmid extractions (Qiagen, Valencia, Calif.). Polymerase chain reaction (PCR) amplification was performed with an I-cycler thermal cycler (Biorad, Hecules, Calif.) with primers synthesized by Operon (Huntsville, Ala.). Topo cloning kits were used for cloning (Invitrogen, Carlsbad, Calif.). Electroporation was performed on a Gene pulser Xcell instrument (Biorad, Hecules, Calif.). Restriction endonucleases were purchased from New England Biolabs (Ipswich, Mass.). DNA sequencing was provided by the University of Florida Interdisciplinary Center for Biotechnology Research. The plasmids constructed are listed in Table 5.

The methods for gene deletion have been previously described (Jantama et al. 2008), with minor modifications made to apply to *E. asburiae* JDR-1. The partial sequence of *E. asburiae* JDR-1 pflB gene (gene bank accession number: EU719655) was determined on a DNA fragment amplified by PCR using specific primers based on *E. coli* pflB gene sequence. A segment of the *E. asburiae* JDR-1 als gene (FJ008982) was amplified using degenerate primers designed from conserved sequences in homologous als genes found in *Enterobacter* sp. 638, *Envinia carotovora* subsp. *atroseptica* SCR11043, *Yersinia enterocolitica* subsp. *enterocolitica* 8081 and *Serratia proteamaculans* 568.

Determination of Lactate Isomers Produced by *E. asburiae* L1

To determine the isomers of lactate formed, fermentation products were assayed with D-lactate or L-lactate dehydrogenases (Taguchi and Ohta 1991). The conditions of the colorimetric enzyme assays were similar to those used to measure lactate dehydrogenase activity (Babson and Babson 1973). $NAD^+$ was obtained from Research Products International Corp, Chicago Ill. All other reagents, substrates, and enzymes were obtained from Sigma. Iodonitrotetrazolium chloride (40 mg), 100 mg $NAD^+$ and 10 mg PMSF were dissolved in 20 ml 0.2 M Tris/HCl (pH 8.2) to obtain the colorimetric reagent. Reactions were initiated by adding 4 Kunitz units (1 mmol/min) of either L-lactate dehydrogenase (rabbit muscle, 140 U/mg protein) or D-lactate dehydrogenase (*Lactobacillus leichmanii*, 232 U/mg protein) in 100 µl colorimetric reagent and 100 µl sample at room temperature. The reduction of iodonitrotetrazolium dye was measured at room temperature at 503 nm. Sodium salts of L and D-lactate (Sigma) were used as standards to define enantiomer specificity of the reaction.

Results and Discussion

Fermentation Characteristics of the Wild Type Strain *E. asburiae* JDR-1

When growing with either 0.8% glucose, 0.5% arabinose or 0.5% xylose as the sole carbon source, the wild type strain produced several products including succinate, lactate, acetate, 2,3-butanediol and ethanol. Glucose fermentations resulted in the formation of 2,3-butanediol, ethanol and acetate as major products. Larger amount of acetate and no 2,3-butanediol was detected in 0.5% xylose and 0.5% arabinose fermentations (Table 6).

Figure 5A:
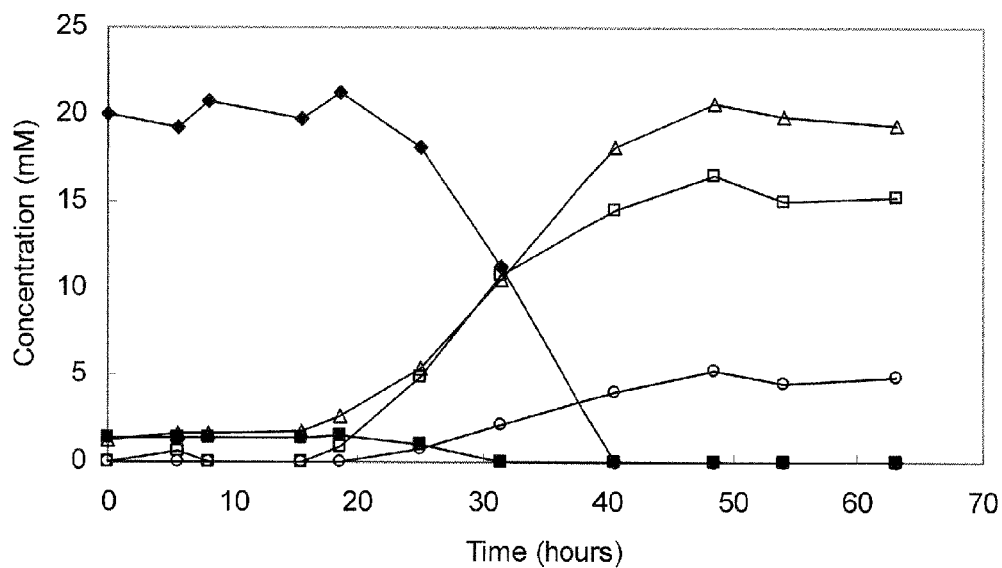
FIGS. 5A-5D: Fermentation time course for different strains in media containing 0.5% sweetgum xylan hydrolysate.

The initial concentrations of substrates in the medium containing 0.5% sweetgum hemicellulose hydrolysate were determined by HPLC to be 20 mM xylose, 1.4 mM MeGAX and a small amount of $MeGAX_2$. Previous studies indicated that MeGAX was metabolized by *E. asburiae* JDR-1 into methanol, glucuronate and xylose (Bi et al. 2009). In these previous studies glucuronate fermentation by *E. asburiae* JDR-1 generated acetate in nearly 100% yield, indicating fermentation products more reduced than acetate could only be produced from the free xylose and the xylose released from MeGAX in the hydrolysate. The theoretical maximum yield of lactate from this hydrolysate medium was 35.7 mM based on the total xylose initially present. In the fermentation of methylglucuronoxylan hydrolysate, *E. asburiae* JDR-1 utilized all of the MeGAX within 30 h and xylose within 40 h. Similar amounts of ethanol (15.6 mM) and acetate (20 mM) were produced but no 2,3-butanediol or lactate was detected (Table 6, FIG. 5A). When supplemented with LB, *E. asburiae* JDR-1 fermented the 0.5% hydrolysate more rapidly than with ZH minimal salts. Substrates were utilized within 15 h, producing 16.2 mM ethanol, 22 mM acetate, and 3.2 mM succinate, again with no 2,3-butanediol or lactate detected. (Table 6, FIG. 5C).

Fermentation Characteristics of the Engineered Strains *E. asburiae* E1 and L1

Figure 6:
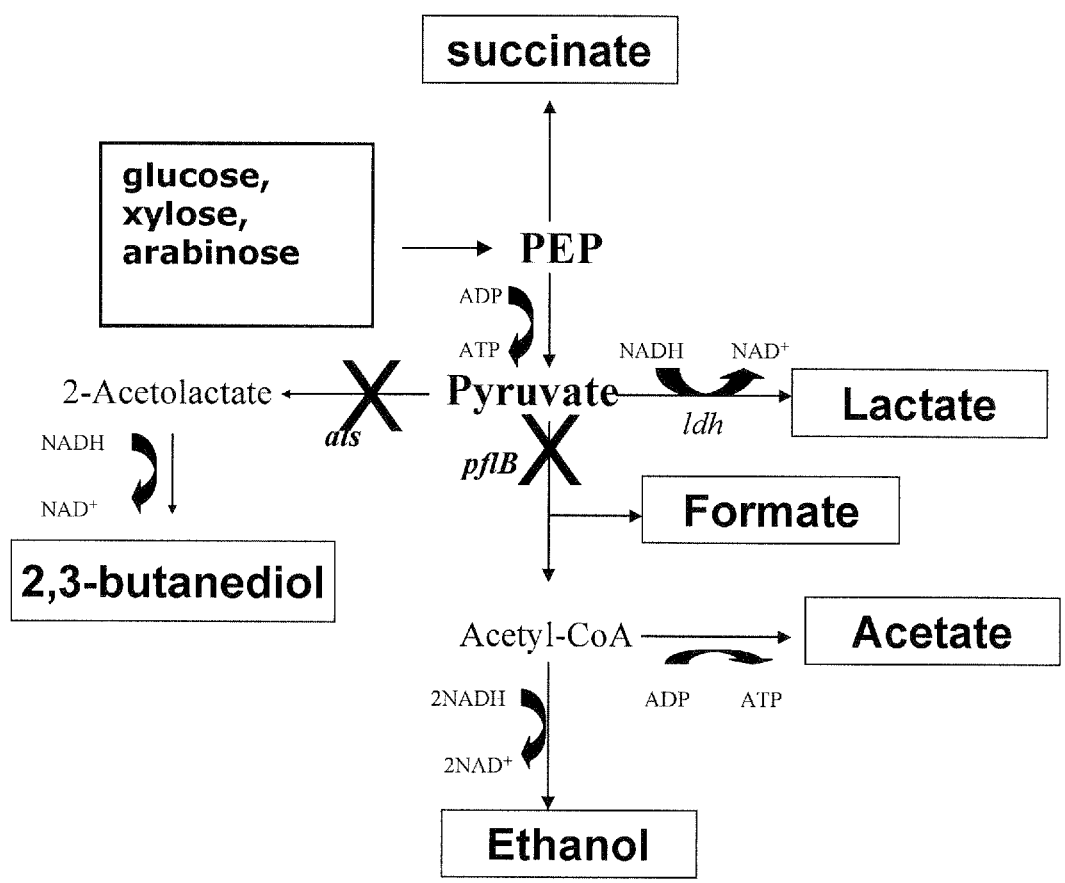
FIG. 6: Diagram to illustrate deletion of als and pflB genes modifying mixed-acid fermentation of *E. asburiae* JDR-1 into a homolactate production pathway in *E. asburiae* L1. Deletion of pathways is indicated in the figure as symbol X.

The major competing pathway to lactate production initiates from the pyruvate formate lyase catalyzed reaction, which produces formate and acetyl-CoA in the wild type strain *E. asburiae* JDR-1. Both acetate and ethanol are produced from acetyl-CoA. In order to convert more carbon flux from pyruvate to lactate, the pflB gene of JDR-1 was deleted to obtain strain *E. asburiae* E1. Since 2,3-butanediol was also produced by *E. asburiae* E1 in the fermentation of glucose (Table 6), the als gene which encodes acetolactate synthase was deleted in *E. asburiae* E1 to eliminate 2,3-butanediol production (Moat et al. 2002). The resulting strain *E. asburiae* L1 was a double mutant lacking pflB and als genes (FIG. 6).

Both *E. asburiae* E1 and L1 produced lactate as the predominant product in glucose, xylose and arabinose fermentations. *E. asburiae* E1 produced 2.9 mM 2,3-butanediol in 0.8% glucose fermentation. The L1 strain with an interrupted 2,3-butanediol-producing pathway produced no 2,3-butanediol and achieved a higher lactate yield (94.1% of the theoretical maximum). In xylose and arabinose fermentations, the L1 strain also achieved higher lactate yield than E1 strain (Table 6).

Figure 5B:
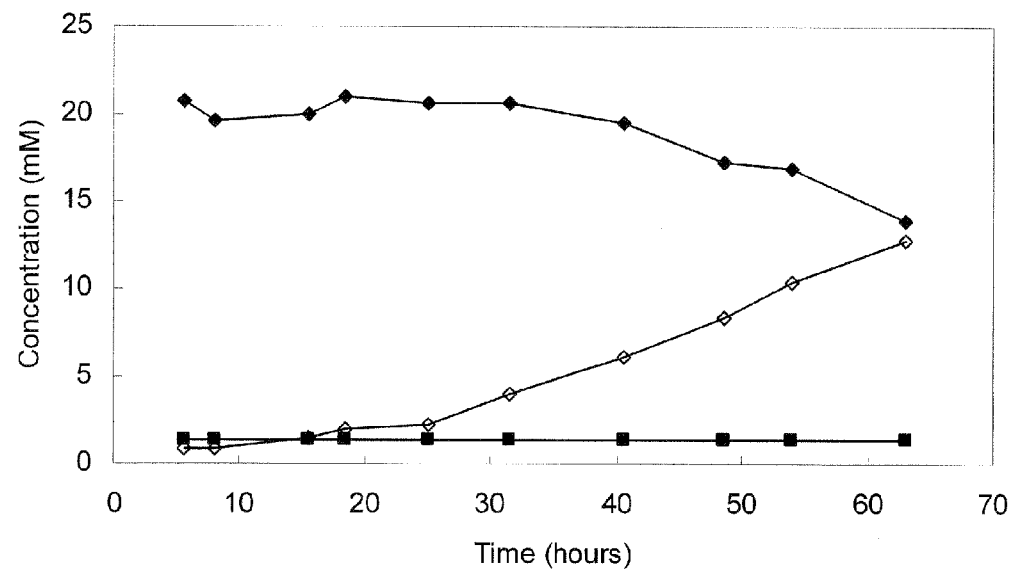
Figure 5C:
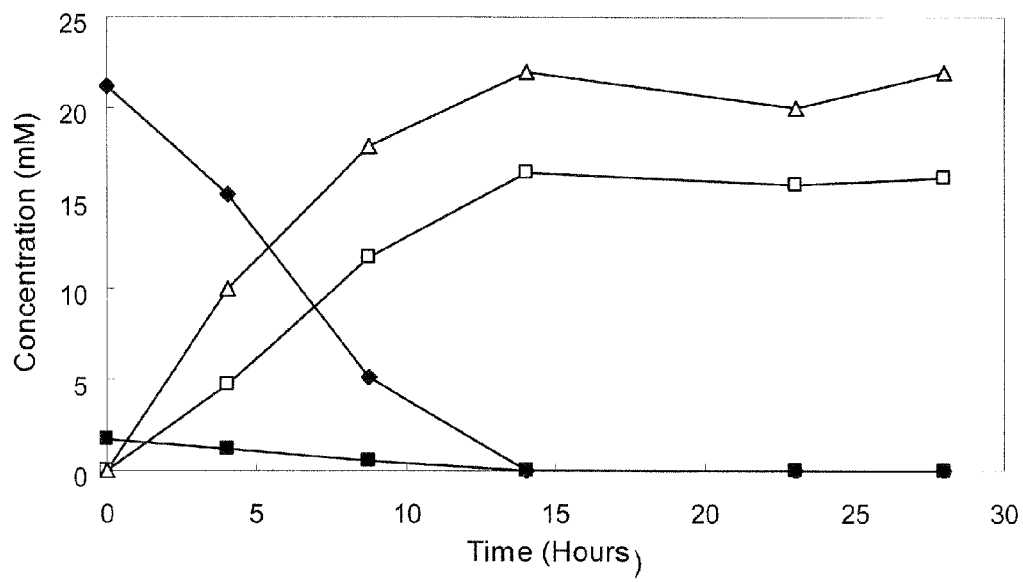
Figure 5D:
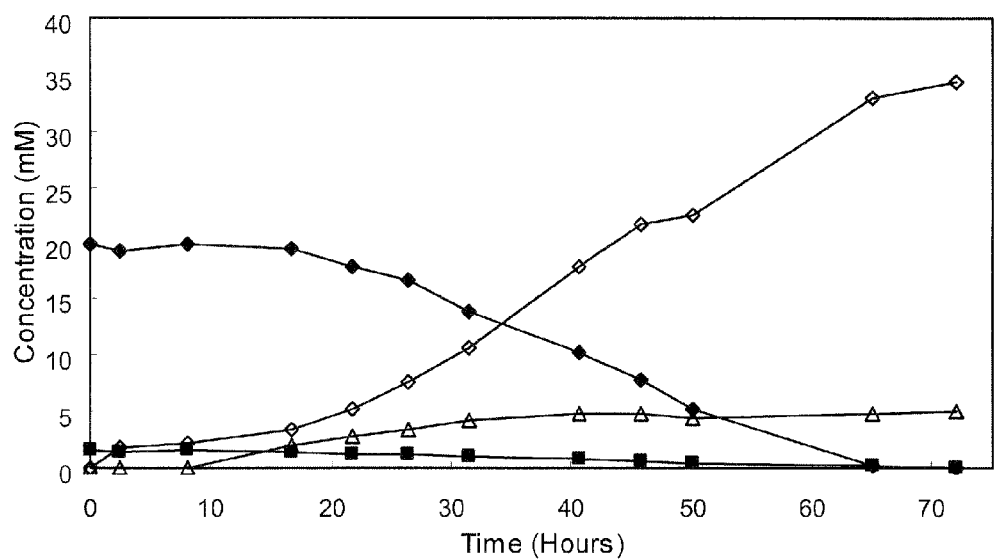

The *E. asburiae* L1 fermented slowly in the xylan hydrolysate with ZH minimal salts. After 60 h, only a portion of free xylose in the hydrolysate was utilized and the MeGAX portion was not utilized (FIG. 5B). Within 100 h, 22.2 mM lactate was produced (Table 6). The low fermentation rate of L1 in hydrolysate medium may be due to a limiting activity of lactate dehydrogenase. The absence of detectable lactate formation in the parent strain during fermentation of xylan hydrolysates also indicates a limitation in lactate dehydrogenase activity of *E. asburiae* JDR-1. The *E. asburiae* L1 strain fermented more rapidly in the xylan hydrolysate supplemented with LB, with the complete consumption of both MeGAX as well as xylose in 65 h (FIG. 5D) with the formation of 36.4 mM lactate as well as very small amount of acetate and succinate (Table 6). Both E1 and L1 were able to produce lactate at 100% of the theoretical maximum yield. The small amounts of acetate were likely derived from the glucuronate group of the 1.4 mM MeGAX present in the hydrolysate substrate.

The utilization of MeGAX by the L1 strain was markedly enhanced with LB supplementation, while the original isolate, *E. asburiae* JDR-1, readily utilized MeGAX in both minimal (FIG. 5A) and LB supplemented (FIG. 5C) media during the mixed acid fermentation that produced acetate and lactate in nearly equal amounts (Table 6). Supplementation with LB doubled the rate of utilization of xylose and nearly trebled the production rate of lactate in the L1 strain (Table 7).

D-Lactate was Produced by *E. asburiae* L1

The optical enantiomer(s) of lactate produced by *E. asburiae* L1 from the fermentation of xylan hydrolysates was determined by measuring the oxidation of lactate catalyzed by D- or L-lactate dehydrogenase with the reduction of iodonitrotetrazolium dye mediated via NADH formation as described in the Materials and Methods section. A sample of medium containing 3.6 mmol lactate (determined by HPLC) of an *E. asburiae* L1 fermentation (72 h) of 0.5% xylan hydrolysate supplemented with LB resulted in an increase in $A_{503}$ from 0 to 0.113 in 5 min when assayed with 4 units of D-lactate dehydrogenase. When the same sample was assayed under the same conditions with 4 units L-lactate dehydrogenase, there was no detectable increase in $A_{503}$. Therefore the lactate produced by *E. asburiae* L1 was D-lactate with an apparent optical purity 100%.

Conclusion

The fermentations of dilute acid hydrolysates of methylglucuronoxylan by *E. asburiae* strains E1 and L1 provide the first examples of lactate formation from the aldouronate as well as the xylose present in these hydrolysates. The efficient formation of the D(−)entantiomer demonstrates a metabolic potential for the efficient production optically pure lactate from the most predominant polysaccharide components in the hemicellulose fractions derived from woody biomass and agricultural residues. Although the relatively low production rate and dependence on rich media limit direct application of *E. asburiae* L1, metabolic evolution by adaptive culturing and further genetic engineering may overcome these limitations.

Example 3

Genetic Engineering for Ethanol Production

Bacterial Strains, Media, and Growth Conditions

The bacterial strains constructed and used in these studies are listed in Table 8. The *E. asburiae* JDR-1 served as a starting point for genetic engineering. During strain construction, cultures were grown aerobically at 30° C., 37° C., or 39° C. in Luria broth (10 g $l^{-1}$ Difco tryptone, 5 g $l^{-1}$ Difco yeast extract, and 5 g NaCl) containing either 2% (w/v) glucose, 5% sucrose or 3% (w/v) arabinose. Ampicillin (50 mg $l^{-1}$), tetracycline (12.5 mg $l^{-1}$), kanamycin (20 mg $l^{-1}$ and 50 mg $l^{-1}$), apramycin (20 mg $l^{-1}$) or chloramphenicol (10 mg and 40 mg $l^{-1}$) were added as needed.

Sweetgum methylglucuronoxylan (MeGAX$_n$) was prepared from sweetgum stem wood (*Liquidambar styraciflua*) as previously described and characterized by $C^{13}$-NMR (Hurlbert and Preston *J Bacteriol* 183:2093-2100 (2001); Kardosova et al. *Carbohydr Res* 308:99-105 (1998)). Dilute acid hydrolysates of methyglucuronoxylan were prepared by acid hydrolysis of 1% (w/v) sweetgum xylan with 0.1 N $H_2SO_4$ at 121° C. for 60 min, followed by neutralization with $BaCO_3$. Total carbohydrate concentrations of substrate preparations were determined by the phenol-sulfuric acid assay (Dubois et al. *Anal Chem* 28:350-356 (1956)) with xylose as a reference or by HPLC (Bi et al. *Appl Envron Microbiol* 75:395-404 (2009)). Minimal media were supplemented with Zucker and Hankin mineral salts (ZH salts) at pH 7.4 (Zucker and Hankin *J Bacteriol* 104:13-18 (1970)). Growth media were buffered with 100 mM sodium phosphate buffer (pH 7.0) or 100 mM 3-(N-morpholino) propane sulfonic acid (MOPS) buffer (pH 7.0) when necessary.

Genetic Methods

Standard methods were used for most of the genetic manipulations. Qiagen kits were used for genomic DNA and plasmid extraction (Qiagen, Valencia, Calif.). Polymerase chain reaction (PCR) amplification was performed with an I-cycler thermal cycler (Biorad, Hecules, Calif.) with primers synthesized by Operon (Huntsville, Ala.). Topo cloning kits were used for cloning (Invitrogen, Carlsbad, Calif.). Electroporation was performed on Gene pulser Xcell (Biorad, Hercules, Calif.). Restriction endonucleases were purchased from New England Biolabs (Ipswich, Mass.). DNA sequencing was provided by the University of Florida Interdisciplinary Center for Biotechnology Research.

Fermentation

Batch fermentations were carried out in 16- by 100-mm screw-cap tubes filled with nitrogen and sealed with rubber stoppers. The tubes were set in a Glas-Col minirotator at 60 rpm in a 30° C. incubator. Neutralized sweetgum xylan acid hydrolysate (0.5% w/v) was added to 2×ZH salts directly as growth medium buffered by 100 mM phosphate buffer or MOPS buffer at pH 7.0. Fermentations in hydrolysates were inoculated to an initial optical density at 600 nm of 1.0 (determined using a Beckman DU500 series spectrophotometer). For analysis of fermentation products, cultures were centrifuged, and the supernatants were passed through 0.22 um filters and subjected to HPLC. Products were resolved on a Bio-Rad HPX-87H column with 0.01 N $H_2SO_4$ at 65° C. Samples were delivered with a 710B WISP automatic injector and chromatography controlled with a Waters 610 solvent delivery system at a flow rate of 0.5 ml/min. Products were detected by differential refractometry with a Waters 2410 RI detector. Data analysis was performed with Waters Millennium Software. A quantitative relationship was determined between *E. asburiae* JDR-1 cell dry weight and culture OD at 600 nm. For calculation of specific consumption rates and specific production rates, the cell dry weight was determined based on the $OD^{600}$ of the fermentation culture, which was 1.0 (0.51 g $l^{-1}$) initially and did not appreciably change during the fermentation in 0.5% xylan hydrolysate.

Transformation of *E. asburiae* JDR-1 with Plasmids Carrying PET Operon

*E. asburiae* JDR-1 was grown with one of several antibiotics at different concentrations in LB and minimal media on agar plates or in liquid media to test its antibiotic resistance. Based upon its sensitivity to chloramphenicol and tetracycline respectively, plasmids pLOI555 ($cm^R$) and pLOI297 ($tet^R$), both containing the PET operon, were transformed into *E. asburiae* JDR-1 or *E. asburiae* E1 by electroporation in a 100 μl cuvette under the condition of 1.8 kV, 25 μF capacitance and 200Ω resistance. For electroporation competent cells from 25 ml exponential phase cultures were washed 3 times by suspension and centrifugation with cold 10% glycerol. Cultures were plated on LB agar containing 2% glucose and tetracycline (12.5 mg $l^{-1}$) or chloramphenicol (40 mg $l^{-1}$) to select *E. asburiae* JDR-1 and E1 carrying pLOI297 or pLO1555 respectively. Plasmids were extracted confirming their presence in *E. asburiae* cells.

Deletion of the pflB Gene in *E. asburiae* JDR-1

The method for gene deletion in *E. coli* was used as previously described (Jantama et al. *Biotechnol Bioeng* 99:1140-53 (2008); Zhang et al. *Appl Microbiol Biotechnol* 77:355-366 (2007)), with minor modifications applied to *E. asburiae* JDR-1. The pflB gene in *E. asburiae* JDR-1 was also selected as an integration site for the PET operon. Several sets of primers were designed based on sequences of pflB orthologs in other *Enterobacter* spp. to amplify this gene fragment from *E. asburiae* JDR-1. Only one set derived from *E. coli* B was found to amplify the *E. asburiae* JDR-1 pflB gene fragment. The amplified *E. asburiae* JDR-1 DNA sequence and *E. coli* K12 pflB sequence were found to have 93% identity. The plasmids constructed are listed in Table 8. The partial sequence of the *E. asburiae* JDR-1 pflB gene (gene bank accession number: EU719655) was determined within a DNA fragment amplified by PCR using specific primers based on the *E. coli* pflB sequence. The 3 kb cat-sacB cassette was obtained by digesting pLO14162 with SmaI and SfoI, and used in subsequent ligations. The pflB gene fragment amplified from *E. asburiae* JDR-1 was cloned into pCR 4-TOPO vector (Invitrogen) to obtain a plasmid, pTOPOpfl. This plasmid was diluted 500-fold and served as template for inside-out PCR amplification using the pfl inside-out primers. The resulting 5.5 kb fragment containing the replicon was ligated to the blunt-end cat-sacB cassette from pLO14162 to produce a new plasmid, pTOPO4162pfl. This 5.5 kb fragment was also used to construct a second plasmid, pTOPODpfl, by phosphorylation and self-ligation. Both pTOPO4162pfl and pTOPODpfl were then digested with XmnI, diluted 500-fold and used as templates for amplification using the pfl primer set to produce linear DNA fragments for integration step 1 (pfl'-cat-sacB-pfl") and step 2 (pfl'-pfl"), respectively. After electroporation of the step 1 fragment into *E. asburiae* JDR-1 containing pLO13240, cells were incubated for 2 hr at 30° C. The recombinant candidates were selected for chloramphenicol (20 mg $l^{-1}$) resistance in Luria broth plates after overnight incubation (15 h) at 39° C. Colonies were patched on both kanamycin (50 mg $l^{-1}$) plates and chloramphenicol (40 mg $l^{-1}$) plates. Those colonies growing on chloramphenicol (40 mg $l^{-1}$) plates but not on kanamycin (50 mg $l^{-1}$) plates were subjected for PCR confirmation. The confirmed mutant colonies were transformed with pLO13240, and prepared for electroporation with the step 2 fragment (pfl'-pfl"). After electroporation, cells were incubated at 30° C. for 4 h and then transferred into a 250-ml flask containing 100 ml of LB minus NaCl with 10% sucrose. Following an overnight incubation (30° C.), colonies were streaked on LB minus NaCl plates containing 6% w/v sucrose (39° C., 16 h). Colonies were tested for loss of apramycin and chloramphenicol resistance and confirmed by PCR. The resulting strain *E. asburiae* E1 had a disrupted pflB gene without detectable heterogonous DNA sequences.

Plasmid Stability in *E. asburiae* JDR-1

*E. asburiae* JDR-1 harboring either pLOI555 or pLOI297 was serially transferred in Luria broth containing 2% glucose without antibiotics for more than 72 generations at 30° C. One generation was defined as a 2-fold increase in culture turbidity. Appropriate dilutions of cultures were plated on Luria agar with and without antibiotic; colonies formed were counted and calculated to obtain the ratio of cells retaining antibiotic resistance to total cells. Ten colonies retaining antibiotic resistance (and therefore presumed to retain pLOI555 or pLOI297) after 72 generations were subjected to fermentation to test their ethanol producing ability.

Assay of PDC Activity

Pyruvate decarboxylase activity was assayed in engineered *E. asburiae* JDR-1 strains by monitoring the pyruvate-dependent oxidation of NADH with alcohol dehydrogenase as a coupling enzyme (Conway et al. *J Bacteriol* 169:2591-2597 (1987); Ohta et al. *Appl Environ Microbiol* 57:2810-2815 (1991)). Exponential phase anaerobic cultures were harvested and cells were disrupted using the FastPrep bead mill MP system (MP Biomedicals, Irvine, Calif.) in 0.05 M phosphate buffer. The supernatant was collected after 15 min centrifugation at 1.8 k rpm (Eppendorf centrifuge 5414). The entire process was carried out at 4° C. Heat treatment for 15 min at 60° C. was used to inactivate competing native enzymes of *E. asburiae* JDR-1 which might affect quantitative measurements of PDC activities in transformants. The enzyme activity assay of PDC was performed in the reaction mixture of 1.0 mM TPP (thiamine pyrophosphate), 1.0 mM $MgCl_2$, 0.40 mM NADH, 20 mM sodium pyruvate and 0.05 M sodium phosphate buffer, pH 6.5. The assay was started by adding 20 μl crude cell extract. Protein concentration of the crude extract was determined with BCA protein assay reagent kit (Pierce Chemical Co., Rockford, Ill.).

Results

Fermentation Characteristics of the Wild Type Strain *E. asburiae* JDR-1

*E. asburiae* JDR-1 performed a mixed-acid fermentation in low substrate concentration. When growing in 2.5% (w/v) glucose or 2% (w/v) xylose, the wild type strain produced a wide range of products, including succinate, lactate, acetate, formate, 2,3-butanediol and ethanol (Table 9). In glucose fermentation, succinate and acetate were produced at low concentrations, approximately 1 mM. Lactate was produced at approximately 10 mM, and the major products were formate, 2,3-butanediol and ethanol, each at approximately 40 mM. More acetate and less 2,3-butanediol were produced in xylose fermentation (Table 9). In both batch fermentations buffered with 0.1 M sodium phosphate (pH 7.0), the wild type strain failed to utilize all the substrates during the 48 h allotted. Even in the buffered medium the pH after fermentation decreased to 4.8, which suggested that acid production might be the main factor preventing the cells from utilizing all the substrate.

Figure 7:
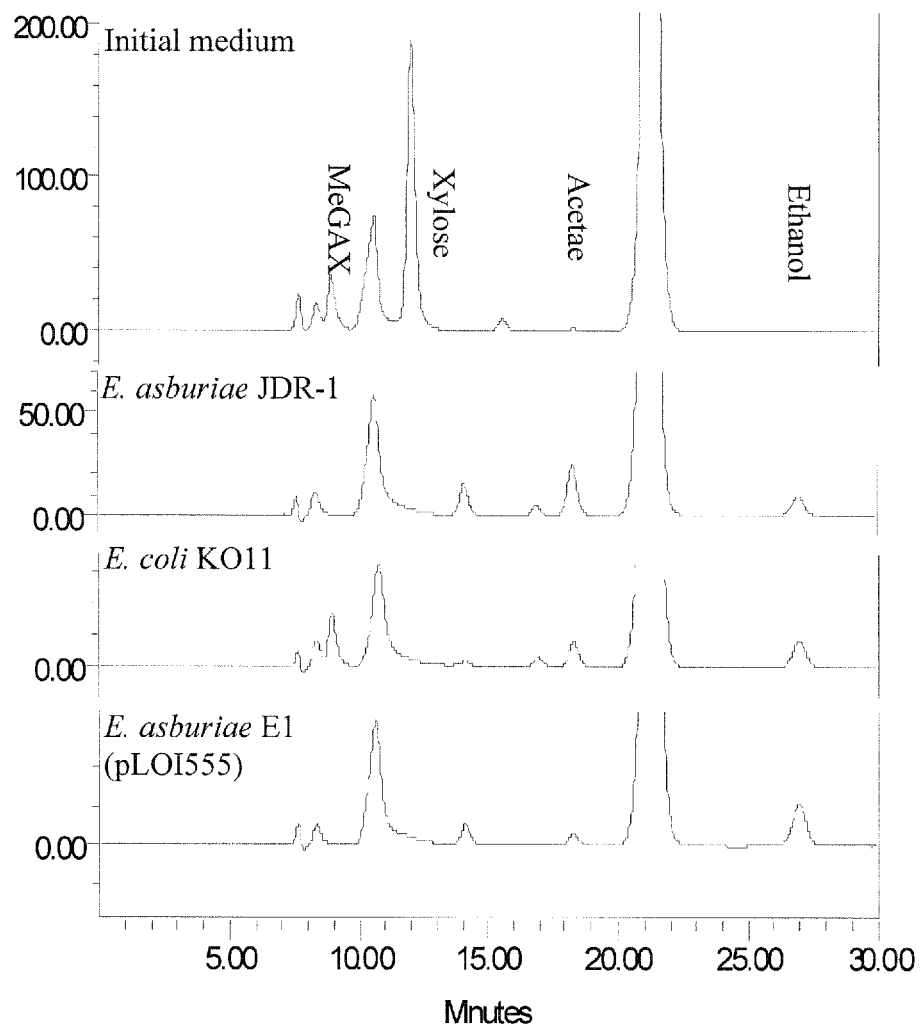
FIG. 7: HPLC profiles of fermentation media of *E. asburiae* JDR-1, *E. coli* KO11 and *E. asburiae* E1 (pLOI555) in 0.5% sweetgum xylan hydrolysate with 0.1 M MOPS buffer after 48 hours of fermentation. (The unlabeled peaks with retention times of 11 min and 21 min were for salts and buffers.)
Figure 8A:
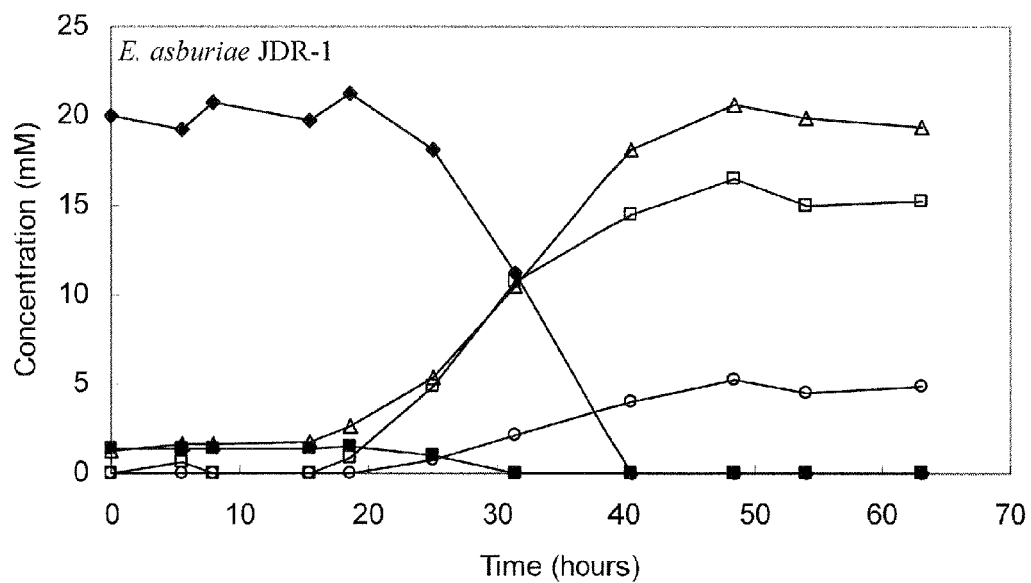
FIGS. 8A-8D: Fermentation time course for different strains in media of buffered sweetgum xylan hydrolysate.

The components in the medium containing 0.5% sweetgum hemicellulose hydrolysate were determined by HPLC to be 20 mM xylose, 1.4 mM MeGAX and a small amount of MeGAX$_2$ (FIG. 7). Previous studies suggested that MeGAX was metabolized by *E. asburiae* JDR-1 into methanol, glucuronate and xylose. Glucuronate fermentation by *E. asburiae* JDR-1 generated acetate in nearly 100% yield, indicating more reduced fermentation products (ethanol and lactate) could only come from the free xylose and the xylose released from MeGAX (Bi et al. *Appl Envron Microbiol* 75:395-404 (2009)). Therefore, the theoretical maximum yield of ethanol from this hydrolysate was calculated to be 35.7 mM based on the total amount of xylose present in hydrolysate. *E. asburiae* JDR-1 was able to completely utilize MeGAX in the 0.5% hydrolysate in about 12 hours and xylose in 20 hours after a period of several hours for adaptation to the hydrolysate medium. Similar amounts of ethanol (15.6 mM) and acetate (20 mM) were produced with small a amount of formate and no detectable 2,3-butanediol; the ethanol yield was 44.2% of the theoretical maximum (Table 10, FIG. 7, FIG. 8A). The specific consumption rates of xylose and MeGAX in the hydrolysate and specific production rates of acetate and ethanol are included in Table 11.

Fermentation Characteristics of *E. asburiae* JDR-1 (pLOI297) and *E. asburiae* JDR-1 (pLOI555)

Plasmids pLOI297 and pLOI555 were transformed into *E. asburiae* JDR-1 for overexpression of pdc and adh genes. Both transformed strains were able to completely utilize 2.5% (w/v) glucose or 2% (w/v) xylose within 48 hours, with ethanol as the predominant fermentation product. The ethanol yields of glucose fermentation were 94.1% and 95.3% for *E. asburiae* JDR-1 (pLOI297) and *E. asburiae* JDR-1 (pLOI555), respectively (Table 9). *E. asburiae* JDR-1 (pLOI555) was further tested in xylose fermentation, and the ethanol yield was even higher, greater than 98% of theoretical. There were also other fermentation products present at concentrations below 10 mM (Table 9).

*E. asburiae* JDR-1 (pLOI555) and JDR-1 (pLOI297) were tested for the fermentation of dilute acid hyrolysates of sweetgum MeGAX$_n$. Both strains consumed MeGAX as well as xylose within 18 hr and fermentation was complete within 25 hr (FIG. 8C for JDR-1 (pLOI555); data for JDR-1 (pLOI297) was not shown). The xylose specific consumption rate of JDR-1 (pLOI555) was similar to the parent strain but the MeGAX specific consumption rate was lower. Ethanol was the major fermentation product, and the yield was much higher than the parent strain. However, both strains produced substantial amount of acetate (approximately 10 mM) and had lower yields of ethanol than with either xylose or glucose as substrates (Table 11).

Figure 8B:
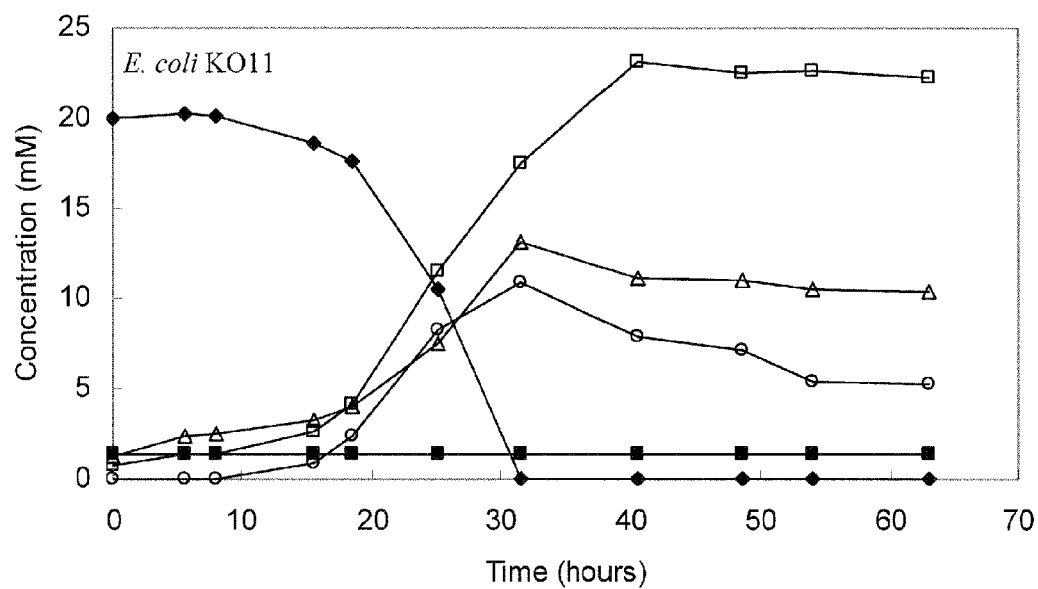

Fermentation Characteristics of *E. asburiae* E1 (pLO1555) Compared with *E. coli* KO11 and Other *E. asburiae* JDR-1 Derivatives Neither 2,3-butanediol nor lactic acid was produced in the hydrolysate fermentation by either *E. asburiae* JDR-1 (pLOI297) or JDR-1 (pLO1555). This result indicated that only the acetate production pathway initiated from pyruvate formate lyase competed for pyruvate and lowered the ethanol yield. In order to direct greater carbon flux from pyruvate to ethanol, the pflB gene of *E. asburiae* JDR-1 was deleted to obtain strain *E. asburiae* E1, followed by pLOI555 transformation. When testing this strain in hydrolysate fermentations, no formic acid was produced, and only small amount of acetate was produced (4.5 mM). After several hours of adaption, the MeGAX portion was consumed in 12 hr and the xylose portion was consumed in 20 hr (FIG. 8D). While the specific consumption rates of the substrates were close to the parent strain and JDR-1 (pLOI555), *E. asburiae* E1 (pLOI555) had a much higher specific production rate of the ethanol (0.11±0.01 g ethanol/g DCW/h) and a much lower specific production rate of the acetate (0.022±0.003 g ethanol/g DCW/h). Most of the carbon sources in the hydrolysates were converted to ethanol, achieving 99% of maximal theoretical yield (Table 10, Table 11, FIG. 7).

Figure 8C:
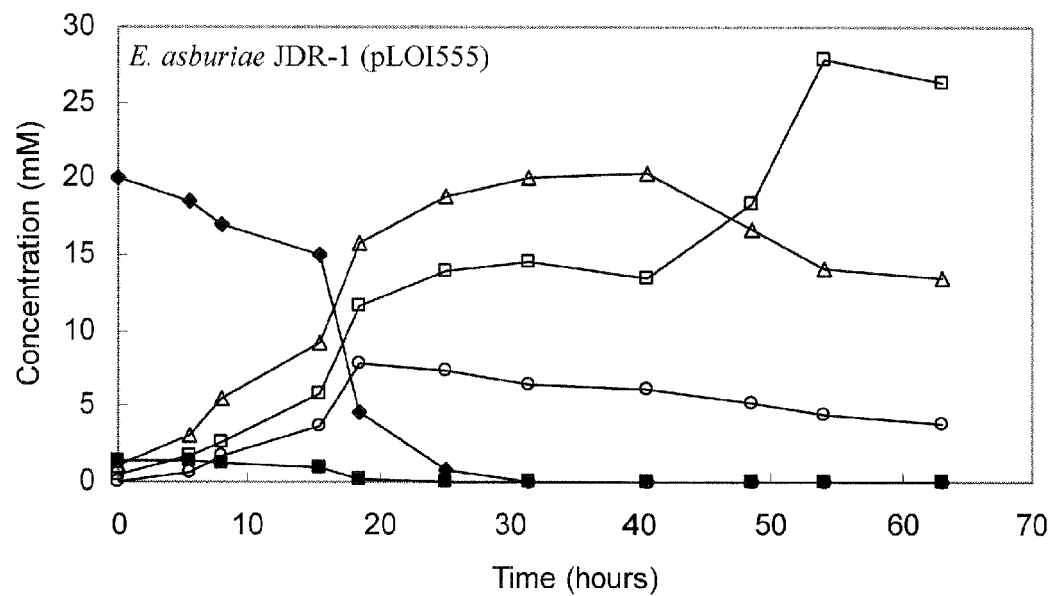
Figure 8D:
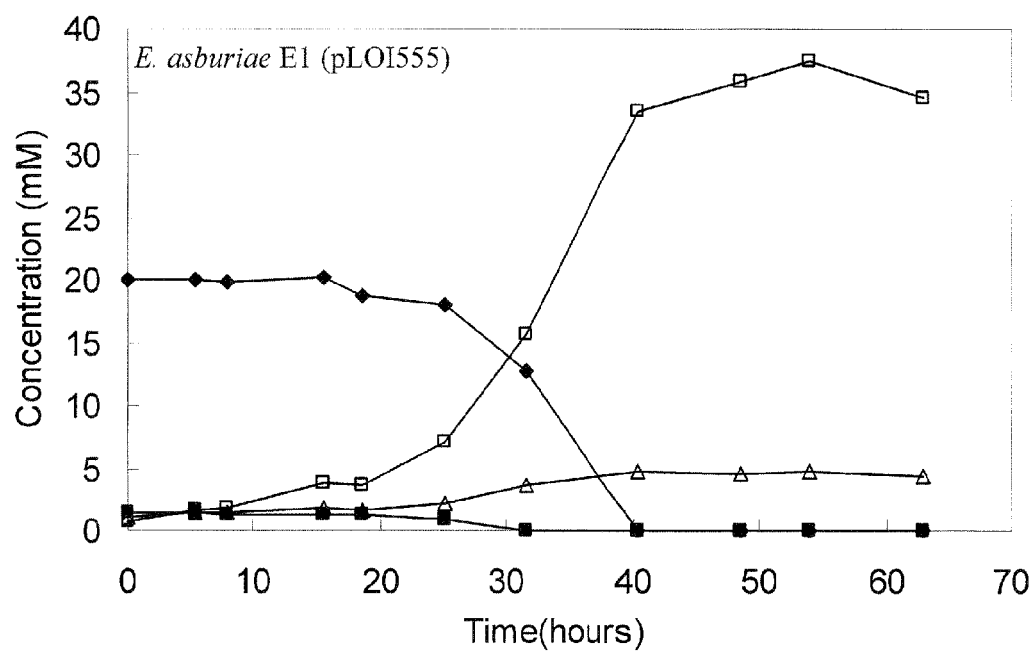

The *E. coli* KO11, which was reported to be able to produce 0.54 gram ethanol per gram glucose (Ohta et al. *Appl Environ Microbiol* 57:893-900 (1991)), could only produce ethanol at 63% of the theoretical maximum in the sweetgum xylan hydrolysate medium, and accumulated a substantial amount (10.6±0.3 mM) of acetate (FIG. 7, FIG. 8C). The sum of ethanol and acetate was 33.1 mM for *E. coli* KO11, and 40.2 mM for JDR-1 (pLO1555), 39.9 mM for JDR-1 (pLOI297) and 40.5 mM for E1 (pLOI555) (Table 10). This result indicated that *E. coli* KO11 utilized less substrate in the hydrolysate than the 3 engineered *E. asburiae* strains and produced lower quantities of products as a result of the inability of *E. coli* KO11 to utilize MeGAX in the hydrolysate (FIG. 7, FIG. 8B). The ethanol specific production rate of *E. coli* KO11 (0.074±0.006 g ethanol/g DCW/h) was much lower than *E. asburiae* E1 (pLOI555) (0.11±0.01 g ethanol/g DCW/h) (Table 11). Compared with *E. coli* KO11, *E. asburiae* E1 (pLO1555) utilized more substrate in sweetgum hydrolysate and was able to produce 57.8% more ethanol at higher rate.

PDC Activities in *E. asburiae* Strains

The PDC enzyme activity produced as a result of expression of heterologous gene pdc in engineered *E. asburiae* strains (Table 12). Because of the relative thermal stability of PDC encoded by the pdc gene of *Zymomonas mobilis*, a heat treatment at 65° C. for 15 minutes was used to inactivate competing native enzymes, e.g. activities associated with the pyruvate dehydrogenase complex, could affect measurements of PDC activity (Conway et al. *J Bacteriol* 169:2591-2597 (1987); Ohta et al. *Appl Environ Microbiol* 57:2810-2815 (1991)). While crude extracts from both strains showed pyruvate-dependent NADH oxidase activity before heat treatment (data not shown), the wild type strains were unable to oxidize NADH after the heat treatment. However, all three strains carrying plasmid with the PET operon showed substantial PDC activities after heat treatment, indicating the presence of PDC encoded by pdc genes derived from *Zymomonas mobilis* in *E. asburiae* strains which carry pLOI297 and pLOI555 plasmids and produce ethanol as the predominant fermentation product.

Plasmid Stability in *E. asburiae* JDR1

The pLOI297 transformant was relatively unstable, with only 10.7% of transformed *E. asburiae* JDR-1 cells retaining tetracycline resistance after cultivation for 72 generations without antibiotic selection pressure. The pLOI555 transformant, however, was quite stable, with 98.1% of pLOI555 transformed *E. asburiae* JDR-1 cells retaining chloramphenicol resistance after growth for 72 generations in the absence of antibiotic (Table 13). Fermentation analysis of 10 descendent colonies retaining antibiotic resistance from strains carrying pLOI297 and pLOI555 was also performed to confirm that strains with retained antibiotic resistance also retained the homoethanolgenic phenotype.

Discussion

A wild type *Enterobacter asburiae* strain with limited knowledge of its genetic and physiological properties was genetically engineered for a new metabolic potential. The methodology and protocols developed in this study may provide reference value for engineering other wild type *Enterobacter* spp. While *E. asburiae* JDR-1 was determined to be relatively resistant to ampicillin and probably other β-lactam antibiotics, it was sensitive to tetracycline (12.5 mg l$^{-1}$), kanamycin (20 mg l$^{-1}$ and 50 mg l$^{-1}$), apramycin (20 mg l$^{-1}$) and chloramphenicol (10 mg l$^{-1}$ and 40 mg l$^{-1}$). To determine if a plasmid-based system developed for use in *E. coli* could be maintained and function in *E. asburiae* JDR-1, pCR4-TOPO plasmid with a small insertion was electroporated into the competent cells and the transformants were able to be selected on a kanamycin (50 mg l$^{-1}$) plate. The transformed pCR4-TOPO plasmid in *E. asburiae* JDR-1 was qualitatively determined by DNA gel electrophoresis to have a lower concentration than in *E. coli* Top10 host (data not shown).

With these transformation systems, *E. asburiae* JDR-1 (pLOI297) and *E. asburiae* JDR-1 (pLOI555), were able to produce ethanol at 94.1% and 95.3% of theoretical yield in glucose, but failed to achieve such high yield in the dilute acid hydrolysates of methylglucuronxylan.

To decrease the formation of organic acids, acetate and formate, the pflB gene was then deleted. The convenient one-step gene inactivation method successfully applied to *E. coli* (Datsenko and Wanner *Proc Nat Acad Sci USA* 97:6640-6645 (2000)) failed to knock out the pflB gene in *E. asburiae* JDR-1, requiring the development of a different protocol. An alternative gene deletion method used PCR fragments with several hundred bases of homologous sequence at both ends instead of 40 bp used by the one-step method (Jantama et al. *Biotechnol Bioeng* 99:1140-53 (2008)). Recombinants were not selected on the plates containing levels of antibiotics used for selection of *E. coli* recombinants and required lower concentrations, kanamycin (20 mg l$^{-1}$) and chloramphenicol (10 mg l$^{-1}$) to be used. This is likely the basis for growth of non-recombinant as well as recombinant colonies and required a second selection that was achieved by patching colonies onto kanamycin (50 mg l$^{-1}$) and chloramphenicol (40 mg l$^{-1}$) plates. By maximizing DNA concentration to approximately 5 µg/µl and cell concentrations of 10$^{10}$ cells/100 µl in electroporation transformation, usually 3 to 6 *E. asburiae* JDR-1 recombinants could be obtained by this process.

The *E. asburiae* strain with a genomic pflB deletion was transformed with a plasmid, pLOI555, to obtain *E. asburiae* E1 (pLOI555), a strain capable of efficiently converting the xylose residues derived from methyglucuronoxylan to ethanol, achieving a yield at 99% of the theoretical maximum. In this respect it has been able to outperform *E. coli* KO11 in medium of sweetgum xylan hydrolysate, which has been developed as a commercial ethanologenic biocatalyst.

The specific PDC activities measured in transformed *E. asburiae* strains were noticeably lower than those measured in the engineered *Klebsiella oxytoca* M5A1(Ohta et al. *Appl Environ Microbiol* 57:2810-2815 (1991)), possibly due to lower copy number of the plasmids pLOI297 and pLOI555 in *E. asburiae* JDR-1. However, as found with engineered *Klebsiella oxytoca* strains, *E. asburiae* JDR-1 pLOI297 had higher activity than pLOI555, which may be due to the presence of the colEl replicon in pLOI297 resulting in a higher copy number than in the strain transformed with pLOI555. It was found that *E. asburiae* E1 (pLO1555) with highest ethanol yield in hydrolysate had the lowest PDC activity in the glucose culture.

The contribution of the adh gene from pLOI1555 is likely critical to homoethanol production in *E. asburiae* E1 as it was in initially generating the ethanologenic strains in *E. coli* (Ingram and Conway *Appl Environ Microbiol* 54:397-404 (1988); Ingram et al. *Appl Environ Microbiol* 53:2420-2425 (1987)). When selected genes were deleted in *E. asburiae* JDR-1 to produce lactate as the predominant product from *E. asburiae* L1, fermentations were slow and incomplete without supplementation with Luria Bertani medium (Bi et al. *Biotechnol Lett*, in press, DOI 10.1007/s10529-009-0044-z (2009)), supporting the conclusion that efficient fermentation to a targeted product requires high level of expression of the gene encoding the oxido-reductase responsible for generating that final fermentation product during the reoxidation of NADH.

Plasmid stability is critical for biocatalysts engineered with genes conferring a desired metabolic potential confined within a plasmid, as consistent traits are required for long-term applications. The plasmid pLOI297, containing colEl replicon, was present in high copy numbers in *E. coli* strains, but was unstable in *Klebsiella oxytoca* M5A1. pLOI555 derived from cryptic low-copy-number plasmids in *E. coli* B (ATCC 11303), however, was very stable in *Klebsiella oxytoca* M5A1(Ohta et al. Appl Environ Microbiol 57:2810-2815 (1991)). Similar to the studies in *Klebsiella oxytoca*, pLOI555 plasmids were found to be more stable than pLOI297 in *E. asburiae* JDR-1. The relative stability of the plasmid in *E. asburiae* E1 (pLOI555) recommend it for further development, perhaps through introduction of the pdc and adh genes into the chromosome as has been achieved for the successful development of *E. coli* KO11 and its derivatives as ethanologenic biocatalysts (Jarboe et al. *Adv Biochem Eng Biotechnol* 108:237-61 (2007)).

All patents, patent applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

TABLE 1

Fermentation products formed by *E. asburiae* JDR-1 from monosaccharides derived from hemicellulose. Anaerobic cultures were allowed to consume each carbon source, initially at 0.25% w/v. Concentrations of components resolved by HPLC were determined for duplicate cultures by differential refractometry.

| Substrate (0.25% w/v) | Fermentation products (mM) | | | |
|---|---|---|---|---|
| | Acetic Acid | Ethanol | Lactic Acid | Formic acid |
| D-Xylose | 10.1 ± 0.1 | 10.2 ± 0.7 | 0 | 1.6 ± 0.3 |
| D-Glucose | 7.2 ± 0.3 | 9.7 ± 0.5 | 1.8 ± 0.1 | 1.6 ± 0.4 |
| D-Mannose | 7.5 ± 0.1 | 9.2 ± 0.2 | 0.9 ± 0.2 | 3.2 ± 0.8 |
| D-Galactose | 9.0 ± 0.4 | 9.0 ± 0.3 | 0 | 0.7 ± 0.3 |
| L-Arabinose | 8.1 ± 0.2 | 9.5 ± 0.1 | 0.8 ± 0.2 | 1.3 ± 0.3 |

TABLE 2

Fermentation products of *E. asburiae* JDR-1 derived from MeGAX$_n$. Acetate, ethanol and formate concentrations were determined in duplicate cultures with HPLC and methanol with GC.

| Substrate (mM) | Products, mM, and yield (product/substrate) | | | |
|---|---|---|---|---|
| | Acetic | Ethanol | Methanol | Formate |
| Xylose (14.3) | 9.5 ± 0.2 (0.7) | 9.4 ± 0.7 (0.7) | ND | 1.6 ± 0.3 |
| Glucuronate (11) | 12.8 ± 0.6 (1.1) | 0 | ND | 2.8 ± 0.4 |
| MeGAX (4.0) | 8.1 ± 0.9 (2.0) | 1.2 ± 0.3 (0.3) | 4.3 ± 1.0 (1.1) | 0 |
| MeGAX$_n$ acid hydrolysate (Xylose 13.7; MeGAX 1.75)[a] | 14.3 ± 1.2 | 9.8 ± 1.1 | <2.5[b] | 0 |
| Xylose (11) + Glucuronate (11) | 20.4 ± 0.5 (1.9) | 5.3 ± 0.4 (0.5) | ND | 0 |

[a]Composition of the acid hydrolysate was determined by HPLC and differential refractometry.
[b]Due to background noise and very small product amounts, accurate data was not obtained for quantification of methanol in the MeGAX$_n$ hydrolysate.
[c]None detected.

TABLE 3

Distribution of $^{13}$C in fermentation products formed in anaerobic cultures of *E. asburiae* JDR-1 and *E. coli* B grown with differentially $^{13}$C labeled xylose and glucose. Carbons enriched in $^{13}$C in different fermentation products were determined and quantified by $^{13}$C-NMR (FIG. 3) and are noted by *. Total Products were quantified by HPLC. The fractions of labeled products to their total products were calculated and noted parenthetically in the table.

| Fermentation | Labeled products, mM, and (fraction) labeled with $^{13}$C | | |
|---|---|---|---|
| | Acetate CH3C*OOH | Ethanol CH3C*H2OH | Lactate CH3C*HOHCOOH + CH3C*HOHC*OOH |
| [2-$^{13}$C]xylose, *E. asburiae* JDR-1 | 4.8 (0.40) | 5.8 (0.43) | 0.9 (0.45) |
| [2-$^{13}$C]xylose, *E. coli* B | 3.0 (0.26) C*H3COOH | 1.9 (0.27) C*H3CH2OH | 2.8 (0.31) C*H3CHOHCOOH |
| [1-$^{13}$C]glucose, *E. asburiae* JDR-1 | 2.3 (0.34) | 4.6 (0.37) | 4.8 (0.38) |
| [6-$^{13}$C]glucose, *E. asburiae* JDR-1 | 1.9 (0.28) | 4.7 (0.35) | 5.4 (0.40) |

TABLE 4

Anaerobic molar cell dry weight and ATP yield from different substrates calculated based on estimated $Y_{ATP}$, 8, for all substrates in *E. asburiae* JDR-1.

| | Fermentation substrates | | | |
|---|---|---|---|---|
| | Glucose | Xylose | Glucuronate | MeGAX |
| $Y_M$-substrate (g/mole)[a] | 20.5 ± 1.4 | 10.2 ± 0.7 | 10.4 ± 0.3 | 32.0 ± 1.1 |
| Estimated ATP yield per mole of substrate | 2.6 | 1.3 | 1.3 | 4.0 |

[a]$Y_M$-substrate: molar cell dry weight yields for different substrates, determined in triplicate with indicated standard deviations.

TABLE 5

Bacterial strains and plasmids.

| Strain and plasmid | Relevant characteristics | Source or reference |
|---|---|---|
| Strains | | |
| *E. coli* Top10 | For general cloning | Invitrogen |
| *E. asburiae* JDR-1 | Wild type | Described herein |
| *E. asburiae* E1 | *E. asburiae* JDR-1 ΔpflB | Described herein |
| *E. asburiae* L1 | *E. asburiae* JDR-1 ΔpflB Δals | Described herein |

TABLE 5-continued

Bacterial strains and plasmids.

| Strain and plasmid | Relevant characteristics | Source or reference |
|---|---|---|
| Plasmids | | |
| PLOI3240 | Am[r] red, red recombinase protein | Wood et al. (2005) |
| pLOI4162 | bla cat; cat-sacB cassette | Jantama et al. (2008) |
| pCR 4-TOPO | bla kan amp; TOPO TA cloning vector | Invitrogen |
| pTOPOpfl | pflB (PCR) amplified from E. asburiae JDR-1 and cloned into PCR4-TOPO vector | Described herein |
| pTOPO4162pfl | cat-sacB cassette cloned into pflB in pTOPOpfl | Described herein |
| pTOPODpfl | PCR fragment amplified from pTOPOpfl, kinase treated, and self-ligated | Described herein |
| pTOPOals | als (PCR) amplified from E. asburiae JDR-1 and cloned into PCR4-TOPO vector | Described herein |
| pTOPO4162als | cat-sacB cassette cloned into als in pTOPOals | Described herein |
| pTOPODals | PCR fragment amplified from pTOPOals, kinase treated, and self-ligated | Described herein |

TABLE 6

Comparing fermentation products of wild type and genetically engineered *E. asburiae* JDR-1 strains[a]

| | Fermentation products (mM) | | | | | |
|---|---|---|---|---|---|---|
| | Ethanol | Acetate | 2,3-Butanediol | Succinate | Lactate | Lactate % yield[b] |
| *E. asburiae* JDR-1 | | | | | | |
| 0.8% glucose | 26.8 | 11.5 | 12.9 | 5.2 | 3.9 | 4.6 |
| 0.5% xylose | 20.9 | 17.5 | 0 | 4.1 | 1 | 1.9 |
| 0.5% arabinose | 24.0 | 17.1 | 0 | 4.2 | 1 | 1.9 |
| 0.5% xylan hydrolysate | 15.6 | 20 | 0 | 0 | 0 | 0 |
| 0.5% xylan hydrolysate with LB | 16.2 | 22 | 0 | 3.2 | 0 | 0 |
| *E. asburiae* E1 | | | | | | |
| 0.8% glucose | 5.6 | 0 | 2.9 | 2.7 | 77 | 91.7 |
| 0.5% xylose | 3.4 | 2.8 | 0 | 3.2 | 46.7 | 89.8 |
| 0.5% arabinose | 6.5 | 2.9 | 0 | 2.1 | 41.3 | 78 |
| 0.5% xylan hydrolysate with LB | 0 | 2 | 0 | 0 | 36.2 | 100.4 |
| *E. asburiae* L1 | | | | | | |
| 0.8% glucose | 4.4 | 0 | 0 | 1.7 | 78.9 | 94.1 |
| 0.5% xylose | 1.5 | 2.9 | 0 | 1.3 | 47.2 | 90.8 |
| 0.5% arabinose | 5.0 | 2.8 | 0 | 2.1 | 49.6 | 93.6 |
| 0.5% xylan hydrolysate[c] | 0 | 0 | 0 | 0 | 22.2 | 96 |
| 0.5% xylan hydrolysate with LB | 0 | 3 | 0 | 1.0 | 36.4 | 101.2 |

[a]Fermentations were completed within 72 h with minimal media, or otherwise as indicated footnote c. The initial concentrations of 0.8% glucose, 0.5% xylose and 0.5% arabinose media were determined by HPLC to be 42 mM, 31 mM and 31.5 mM, respectively. The 0.5% xylan hydrolysate medium was measured to contain 20 mM xylose and 1.4 mM MeGAX.

[b]Percent of actual yield of lactate to theoretical maximum yield. Maximum yield is defined as 2 mol lactate/mol glucose or 5 mol lactate/3 mol xylose.

[c]This result was obtained after fermentation for 100 h at which time 65% of the xylose in the hydrolysate was utilized.

TABLE 7

Specific consumption rates and specific production rates of
*E. asburiae* L1 in 5 g/l acid hydrolysate of sweetgum xylan[a]

| Strains | q Xylose (g xylose/g DCW/h) | q MeGAX (g MeGAX/g DCW/h) | q Lactate (g lactate/g DCW/h) |
|---|---|---|---|
| *E. asburiae* L1 in ZH salts | 0.067 ± 0.006 | 0 | 0.049 ± 0.003 |
| *E. asburiae* L1 in 0.12% LB | 0.13 ± 0.01 | 0.019 ± 0.002 | 0.13 ± 0.005 |

[a] q Xylose and q MeGAX: Xyose and MeGAX specific consumption rate respectively, as grams of substrate consumed per gram dry cell weight per hour. q Lactate: Lactate specific production rate, products generated per gram dry cell weight per hour.

TABLE 8

Bacterial strains and plasmids for engineering ethanolgenic *E. asburiae*.

| Strain and plasmid | Relevant characteristics | Source or reference |
|---|---|---|
| Strains | | |
| *E. coli* Top10 | For general cloning | Invitrogen |
| *E. coli* KO11 | pfl::(pdc⁻adhB⁻cat) Δfrd | Ohta et al. Appl Environ Microbiol 57: 893-900 (1991) |
| *E. asburiae* JDR-1 | Wild type | Described herein |
| *E. asburiae* E1 | *Enterobacter asburiae* JDR-1 ΔpflB | Described herein |
| Plasmids | | |
| PLOI3240 | Am[r] red, red recombinase protein | Wood et al. Biotechnol Progr 21: 1366-1372 (2005) |
| pLOI297 | Tc[r] pdc[+] adhB[+] | Ingram et al. Appl Environ Microbiol 55: 1943-1948 (1989) |
| pLOI555 | Cm[r] pdc[+] adhB[+] | Ohta et al. Appl Environ Microbiol 57: 2810-2815 (1991) |
| pLOI4162 | bla cat; cat-sacB cassette | Jantama et al. Biotechnol Bioeng 99: 1140-53 (2008) |
| pCR 4-TOPO | bla kan amp; TOPO TA cloning vector | Invitrogen |
| pTOPOpfl | pflB (PCR) amplified from *E. asburiae*. JDR-1 and cloned into PCR4-TOPO vector | Described herein |
| pTOPO4162pfl | cat-sacB cassette cloned into pflB in pTOPOpfl | Described herein |
| pTOPODpfl | PCR fragment amplified from pTOPOpfl, kinase treated, and self-ligated | Described herein |

TABLE 9

Comparison of sugar fermentation products of wild type and genetically engineered *E. asburiae* JDR-1. Fermentations were carried out at 30° C. in ZH minimal media for 48 hours as described in the Materials and Methods section.

| Fermentations | Fermentation products (mM) | | | | | | Ethanol yield (% of theoretical)[a] |
|---|---|---|---|---|---|---|---|
| | Succinate | Lactate | Formate | Acetate | 2,3-butanediol | Ethanol | |
| Glucose (2.5% w/v) | | | | | | | |
| *E. asburiae* JDR-1[b] | 2.0 | 9.6 | 39.1 | 1.0 | 45.9 | 45.0 | 25.6 |
| *E. asburiae* JDR-1 (pLOI297) | 1.8 | 4.7 | 9.4 | 3.8 | ND | 261.6 | 94.1 |
| *E. asburiae* JDR-1 (pLOI555) | 1.6 | 2 | 7.7 | 3.4 | ND | 265 | 95.3 |

TABLE 9-continued

Comparison of sugar fermentation products of wild type and genetically engineered E. asburiae JDR-1. Fermentations were carried out at 30° C. in ZH minimal media for 48 hours as described in the Materials and Methods section.

| Fermentations | Fermentation products (mM) | | | | | | Ethanol yield (% of theoretical)[a] |
|---|---|---|---|---|---|---|---|
| | Succinate | Lactate | Formate | Acetate | 2,3-butanediol | Ethanol | |
| Xylose (2% w/v) | | | | | | | |
| E. asburiae JDR-1[b] | 12.7 | 5.6 | 15.0 | 25.2 | 13.4 | 42.6 | 32.8 |
| E. asburiae JDR-1 (pLOI555) | 2.2 | 1.2 | 3.6 | 4.2 | ND | 217.4 | 98.0 |

[a]Percentage of amount of ethanol produced to a theoretical maximal amount. A yield of 100% is defined as 2 mole ethanol/mole glucose or 5 mole ethanol/3 mole xylose.
[b]E. asburiae JDR-1 did not completely utilize the substrates within 48 hours.

TABLE 10

Fermentation products from acid hydrolysates of sweetgum xylan. Fermentations were carried out at 30° C. in ZH minimal media for 48 hours as described in the Materials and Methods section. Results were averages of 3 experiments.

| | Fermentation products (mM) | | | Ethanol yield (% of theoretical)[a] |
|---|---|---|---|---|
| | Formic acid | Acetic acid | Ethanol | |
| E. asburiae JDR-1 | 4.9 ± 0.4 | 20.0 ± 0.7 | 15.6 ± 0.8 | 44 ± 2 |
| E. coli KO11 | 5.9 ± 1.0 | 10.6 ± 0.3 | 22.5 ± 0.2 | 63 ± 1 |
| E. asburiae JDR-1 (pLOI555) | 4.0 ± 0.4 | 13.5 ± 0.5 | 26.7 ± 1.0 | 75 ± 3 |
| E. asburiae JDR-1 (pLOI297) | 3.8 ± 0.3 | 9.9 ± 0.3 | 30.0 ± 1.5 | 84 ± 5 |
| E. asburiae E1 (pLOI555) | 0 | 4.5 ± 0.2 | 35.5 ± 1.1 | 99 ± 3 |

[a]percentage of amount of ethanol produced relative to the theoretical maximum. A yield of 100% is defined as 2 mole ethanol/mole glucose or 5 mole ethanol/3 mole xylose.

TABLE 11

Specific consumption rates and specific production rates in acid hydrolysates of sweetgum xylan (5 g/liter)[a]. Results were averages of 3 experiments.

| Strains | q Xylose | q MeGAX | q Acetate | q Ethanol |
|---|---|---|---|---|
| E. asburiae JDR-1 | 0.33 ± 0.04 | 0.087 ± 0.012 | 0.13 ± 0.01 | 0.060 ± 0.009 |
| E. coli KO11 | 0.38 ± 0.04 | ND | 0.11 ± 0.01 | 0.074 ± 0.006 |
| E. asburiae JDR-1 (pLOI555) | 0.29 ± 0.03 | 0.058 ± 0.012 | 0.14 ± 0.02 | 0.052 ± 0.004 |
| E. asburiae E1 (pLOI555) | 0.32 ± 0.28 | 0.077 ± 0.13 | 0.022 ± 0.003 | 0.11 ± 0.01 |

[a]q xylose is defined as consumed g xylose/g DCW(dry cell weight)/h; q MeGAX is defined as consumed g MeGAX/g DCW(dry cell weight)/h; q acetate is defined as produced g acetate/g DCW(dry cell weight)/h; q ethanol is defined as produced g ethanol/g DCW(dry cell weight)/h.

TABLE 12

Specific activity of PDC in cell crude extract from E. asburiae JDR-1 derived strains. Results were averages of 3 experiments.

| Strains | Specific Activity (U[a]/mg of cell protein) |
|---|---|
| E. asburiae JDR-1 | 0 |
| E. asburiae JDR-1 (pLOI297) | 1.02 ± 0.12 |
| E. asburiae JDR-1 (pLOI555) | 0.77 ± 0.13 |
| E. asburiae E1 (pLOI555) | 0.53 ± 0.10 |

[a]One U is defined as that amount of the enzyme that catalyzes the conversion of 1 μmole of substrate per minute at room temperature.

TABLE 13

Plasmid stability of pLOI297 and pLOI555 in E. asburiae JDR-1. Results were averages of 3 experiments.

| | % cells retaining antibiotic resistance | |
|---|---|---|
| Plasmids | After 36 generations | After 72 generations |
| pLOI297 | 29.5 ± 1.3 | 10.7 ± 2.6 |
| pLOI555 | 100.0 ± 2.8 | 98.1 ± 11.8 |

REFERENCES

Babson A L, Babson S R (1973) Kinetic colorimetric measurement of serum lactate dehydrogenase activity. Clin Che 19:766-769.

Bauchop, T. and S. R. Elsden. 1960. The growth of microorganisms in relation to their energy supply. J. Gen. Microbiol. 23:457-469.

Bi C, Rice J D, Preston J F (2009) Complete fermentation of xylose and methylglucuronoxylose derived from methylglucuronoxylan by *Enterobacter asburiae* strain JDR-1. Appl Environ Microbiol 75:395-404.

Bi, C., X. Zhang, J. D. Rice, L. O. Ingram and J. F. Preston. 2009. Genetic engineering of *Enterobacter asburiae* strain JDR-1 for efficient D(−) lactic acid production from hemicellulose hydrolysate. Biotechnol. Lett. In press. DOI 10.1007/s10529-009-0044-z Brenner, D. J., A. C. Mcwhorter, A. Kai, A. G. Steigerwalt, and J. J. Farmer. 1986. *Enterobacter asburiae* sp-nov, a new apecies found in clinical specimens, and reassignment of *Erwinia dissolvens* and *Erwinia nimipressuralis* to the genus *Enterobacter* as *Enterobacter dissolvens* comb-nov and *Enterobacter nimipressuralis* comb-nov. J. Clin. Microbiol. 23:1114-1120.

Conway. T., G. W. Sewell, Y. A. Osman, and L. O. Ingram. 1987. Cloning and sequencing of the alcohol dehydrogenase-II gene from *Zymomonas mobilis*. J. Bacteriol. 169:2591-2597.

Datsenko, K. A., and B. L. Wanner. 2000. One-step inactivation of chromosomal genes in *Escherichia coli* K-12 using PCR products. Proc. Nat. Acad. Sci. U.S.A. 97:6640-6645.

Dien, B. S., M. A. Cotta, and T. W. Jeffries. 2003. Bacteria engineered for fuel ethanol production: current status. Appl. Microbiol. Biotechnol. 63:258-266.

Dien, B. S., H. J. G. Jung, K. P. Vogel, M. D. Casler, J. F. S. Lamb, L. Iten, R. B. Mitchell, and G. Sarath. 2006. Chemical composition and response to dilute-acid pretreatment and enzymatic saccharification of alfalfa, reed canarygrass, and switchgrass. Biomass and Bioenergy 30:880-891.

Dubois, M., K. A. Gilles. J. K. Hamilton, P. A. Rebers, and F. Smith. 1956. Colorimetric method for determination of sugars and related substances. Anal. Chem. 28:350-356.

Gunsalus, I. C., B. L. Horecker, and W. A. Wood. 1955. Pathways of carbohydrate metabolism in microorganisms. Bacteriol. Rev. 19:79-128.

Gunsalus, I. C. and C. W. Shuster. 1961. Energy yielding metabolism in bacteria, p. 1-58. In I. C. Gunsalus and R. Y. Stanier. (ed.), The Bacteria. Academic Press Inc., New York.

Hasona, A., Y. Kim, F. G. Healy, L. O. Ingram, and K. T. Shanmugam. 2004. Pyruvate formate lyase and acetate kinase are essential for anaerobic growth of *Escherichia coli* on xylose. J. Bacteriol. 186:7593-7600.

Hoffmann, H., S. Stindl, W. Ludwig, A. Stumpf, A. Mehlen, J. Heesemann, D. Monget, K. H. Schleifer, and A. Roggenkamp. 2005. Reassignment of *Enterobacter dissolvens* to *Enterobacter cloacae* as *E. cloacae* subspecies *dissolvens* comb. nov and emended description of *Enterobacter asburiae* and *Enterobacter kobei*. Syst. Appl. Microbiol. 28:196-205.

Hugouvieuxcottepattat, N. and J. Robertbaudouy. 1987. Hexuronate catabolism in *Erwinia chrysanthemi*. J. Bacteriol. 169:1223-1231.

Hurlbert, J. C. and J. F. Preston. 2001. Functional characterization of a novel xylanase from a corn strain of *Erwinia chrysanthemi*. J. Bacteriol. 183:2093-2100.

Ingram, L. O., H. C. Aldrich, A. C. C. Borges, T. B. Causey, A. Martinez, F. Morales, A. Saleh, S. A. Underwood, L. P. Yomano, S. W. York, J. Zaldivar, and S. D. Zhou. 1999. Enteric bacterial catalysts for fuel ethanol production. Biotechnol. Prog. 15:855-866.

Ingram, L. O., F. Alterthum, and K. Ohta. 1989. Efficient ethanol production from xylose, lactose and glucose by recombinant *Escherichia coli*. Appl. Environ. Microbiol. 55:1943-1948.

Ingram, L. O., and T. Conway. 1988. Expression of different levels of ethanologenic enzymes from *Zymomonas mobilis* in recombinant strains of *Escherichia coli*. Appl. Environ. Microbiol. 54:397-404.

Ingram L O, Conway T, Clark D P, Sewell G W, Preston J (1987) Genetic engineering of ethanol production in *Escherichia coli*. Appl Environ Microbiol 53:2420-2425.

Jacobs A. Larsson P T, Dahlman O (2001) Distribution of uronic acids in xylans from various species of soft- and hardwood as determined by MALDI mass spectrometry. Biomacromolecules 2:979-990.

Jantama K, Haupt M J, Svoronos S A, Zhang X L, Moore J C Shanmugam K T, Ingram L O (2008) Combining metabolic engineering and metabolic evolution to develop non-recombinant strains of *Escherichia coli* C that produce succinate and malate. Biotechnol Bioeng 99:1140-1153.

Jarboe, L. R., T. B. Grabar, L. P. Yomano, K. T. Shanmugan, and L. O. Ingram. 2007. Development of ethanologenic bacteria. Biofuels. 108:237-261.

Jarboe, L. R., T. B. Grabar, L. P. Yomano, K. T. Shanmugan, and L. O. Ingram. 2007. Development of ethanologenic bacteria. Adv. Biochem. Eng. Biotechnol. 108:237-61.

Kardosova, A., M. Matulova, and A. Malovikova. 1998. (4-O-methyl-alpha-D-glucurono)-D-xylan from *Rudbeckia fulgida*, var. *sullivantii* (Boynton et Beadle). Carbohydr. Res. 308:99-105.

Kheshgi, H. S., R. C. Prince, and G. Marland. 2000. The potential of biomass fuels in the context of global climate change: focus on transportation fuels. Annual Review of Energy and the Environment. 25:199-244.

Lee Y. Y., P. Iyer and R. W. Torget. 1999. Dilute-acid hydrolysis of lignocellulosic biomass. Adv. Biochem. Eng./Biotechnol. 65:93-115.

Linton, K. J. and C. F. Higgins. 1998. The *Escherichia coli* ATP-binding cassette (ABC) proteins. Molecular Microbiology 28:5-13.

McMillan, J. D. 1997. Bioethanol production: Status and prospects. Renewable Energy. 10:295-302.

Moat A G, Foster J W, Spector M P (2002) Microbial physiology 4th edn. Wiley-Liss, New York.

Moat, A. G., Foster, J. W., and Spector. M. P. 2002. Fermentation pathways. p. 412-433. In Moat, A. G., Foster, J. W., and Spector, M. P. (eds), Microbial Physiology, 4th ed. Wiley-Liss, New York, N.Y., USA.

Nong, G., V. Chow, J. D. Rice, F. J. St. John and J. F. Preston. An aldouronic acid-utilization operon in *Paenibacillus* sp. JDR encodes an alpha-glucuronidase with activity on aldouronic acids generated by acid and enzyme-mediated digestion of methylglucuronoxylan. ASM National Meeting, Atlanta, Ga., 2005.

Ohta, K., D. S. Beall, J. P. Mejia, K. T. Shanmugam, and L. O. Ingram. 1991. Genetic improvement of *Escherichia coli* for ethanol production chromosomal integration of *Zymonionas mobilis* genes encoding pyruvate decarboxylase and alcohol dehydrogenase II. Appl. Environ. Microbiol. 57:893-900.

Ohta, K., D. S. Beall, J. P. Mejia, K. T. Shanmugam, and L. O. Ingram. 1991. Metabolic engineering of *Klebsiella oxytoca* M5A1 for ethanol production from xylose and glucose. Appl. Environ. Microbiol. 57:2810-2815.

Patel, M. A., M. S. Ou, R. Harbrucker, H. C. Aldrich, M. L. Buszko, L. O. Ingram, and K. T. Shanmugam. 2006. Isolation and characterization of acid-tolerant, thermophilic bacteria for effective fermentation of biomass-derived sugars to lactic acid. Appl. Environ. Microbiol. 72:3228-3235.

Pordesimo, L. O., B. R. Hames, S. Sokhansanj, and W. C. Edens. 2005. Variation in corn stover composition and energy content with crop maturity. Biomass and Bioenergy 28:366-374.

Preston, J. F., J. C. Hurlbert, J. D. Rice, A. Ragunathan, and F. J. St John. 2003. Microbial strategies for the depolymerization of glucuronoxylan: leads to biotechnological applications of endoxylanases, p. 191-210. In S. D. Mansfield and J. N. Sandler (ed), Applications of Enzymes to Lignocellulosics. American Chemical Society, Washington D.C.

Preston, J. F., J. D. Rice, L. O. Ingram, and N. T. Keen. 1992. Differential depolymerization mechanisms of pectate lyases secreted by *Erwinia chrysanthemi* EC16. J. Bacteriol. 174:2039-2042.

Puchta, H., and B. Hohn. 1991. A transient assay in plant cells reveals a positive correlation between extrachromosomal recombination rates and length of homologous overlap. Nucleic Acids Res. 19:2693-2700.

Qian, Y., L. P. Yomano, J. F. Preston, H. C. Aldrich, and L. O. Ingram. 2003. Cloning, characterization, and functional expression of the *Klebsiella oxytoca* xylodextrin utilization operon (xynTB) in *Escherichia coli*. Appl. Environ. Microbiol. 69:5957-5967.

Robertbaudouy, J., R. Portalier, and F. Stoeber. 1981. Regulation of hexuronate system genes in *Escherichia coli* K12 multiple regulation of the uxu operon by exur and uxur gene products. J. Bacteriol. 145:211-220, Rodriguez, M., E. A. Martinez, S. W. York, K. Zuobi-Hasona, L. O. Ingram, K. T.

Shanmugam and J. F. Preston. 2001. Properties of the hemicellulose fractions of lignocellulosic biomass affecting bacterial ethanol production. Abstracts of the 101$^{st}$ National Meetings of the American Society of Microbiology meetings in Orlando, Fla., USA. P 535 (2001).

Russell, J. B. and G. M. Cook. 1995. Energetics of bacterial growth balance of anabolic and catabolic reactions. Microbiol. Rev. 59:48-62.

Saha B C (2003) Hemicellulose bioconversion. J Ind Microbio Biotechnol 30:279-291.

Saha B C, Iten L B, Cotta M A, Wu Y V (2005) Dilute acid pretreatment, enzymatic saccharification, and fermentation of rice hulls to ethanol. Biotechnol Prog 21:816-822.

SanFrancisco, M. J. D. and R. W. Keenan. 1993. Uptake of galacturonic acid in *Erwinia* chrysanthemi ec16. J. Bacteriol. 175:4263-4265.

Scott, A. I. and R. L. Baxter. 1981. Applications of C-13 NMR to metabolic studies. Annu. Rev. Biophys. Bioeng. 10:151-174.

Shanmugam, K. T. and L. O. Ingram. 2008. Engineering biocatalysts for production of commodity chemicals. J. Mol. Microbiol. Biotechnol. 15:8-15.

Sharma, V., V. Kumar. G. Archana, and G. N. Kumar. 2005. Substrate specificity of glucose dehydrogenase (GDH) of *Enterobacter asburiae* PSIS and rock phosphate solubilization with GDH substrates as C sources. Can. J. Microbiol. 51:477-482.

Shulami, S., G. Gat, A. L. Sonenshein, and Y. Shoham. 1999. The glucuronic acid utilization gene cluster from *Bacillus stearothermophilus* T6. J. Bacteriol. 181:3695-3704.

Simoni, R. D., S. Roseman, and M. H. Saier, Jr. 1976. Sugar transport. Properties of mutant bacteria defective in proteins of the phosphoenolpyruvate: sugar phosphotransferase system. J. Biol. Chem. 251:6584-6597.

Smalley, A. J., P. Jahrling, and Vandermark, P J. 1968. Molar growth yields as evidence for oxidative phosphorylation in *Streptococcus faecalis* strain 10Cl. J. Bacteriol. 96:1595-1600.

St John, F. J., J. D. Rice, and J. F. Preston. 2006. *Paenibacillus* sp strain JDR-2 and XynA(1): a novel system for methylglucuronoxylan utilization. Appl. Environ. Microbiol. 72:1496-1506.

Sun, J. X., X. F. Sun, R. C. Sun, and Y. Q. Su. 2004. Fractional extraction and structural characterization of sugarcane bagasse hemicelluloses. Carbohydrate Polymers 56:195-204.

Sun, R. C., J. M. Fang, J. Tomkinson, Z. C. Geng, and J. C. Liu. 2001. Fractional isolation, physico-chemical characterization and homogeneous esterification of hemicelluloses from fast-growing poplar wood. Carbohydrate Polymers 44:29-39.

Taguchi H, Ohta T (1991) D-lactate dehydrogenase is a member of the D-isomer-specific 2-hydroxyacid dehydrogenase family—cloning, sequencing, and expression in *Escherichia coli* of the D-Lactate dehydrogenase gene of *Lactobacillus plantarum*. J Biol Chem 266:12588-12594.

Timell T E (1964) Wood hemicelluloses. Adv Carbohydr Chem 19:247-302.

von Sivers, M. and G. Zacchi. 1996. Ethanol from lignocellulosics: A review of the economy. Bioresour. Technol. 56:131-140.

Wood B E, Yomano L P, York S W, Ingram L O (2005) Development of industrial medium required elimination of the 2,3-butanediol fermentation pathway to maintain ethanol yield in an ethanologenic strain of *Klebsiella oxytoca*. Biotechnol Prog 21:1366-1372.

Zhang. X., K. Jantama, J. C. Moore, K. T. Shanmugam, and L. O. Ingram. 2007. Production of L-alanine by metabolically engineered *Escherichia coli*. Appl. Microbiol. Biotechnol. 77:355-366.

Zucker, M. and L. Hankin. 1970. Regulation of pectate lyase synthesis in *Pseudomonas fluorescens* and *Erwinia carotovora*. J. Bacteriol. 104:13-18.

Zuobi-Hasona, K., F. J. St. John, J. D. Rice and J. F. Preston. 2001. Oligosaccharides containing glucuronoxylose as substrates for selecting bacteria for depolymerization of hemicellulose. Abstracts of the 101$^{st}$ National Meetings of the American Society of Microbiology meetings in Orlando, Fla., USA. p 534 (2001).

I claim:

1. An isolated *E. asburiae* strain comprising the following genetic modifications: incorporation and expression of a gene encoding alcohol dehydrogenase, incorporation of a gene encoding pyruvate decarboxylase and inactivation of pyruvate formate lyase in said strain.

2. The isolated *E. asburiae* strain of claim 1, wherein said strain comprises incorporation and overexpression of a *Zymomonas mobilis* gene encoding alcohol dehydrogenase, incorporation and overexpression of a *Zymomonas mobilis* gene encoding pyruvate decarboxylase and disruption or mutation of the pyruvate formate lyase gene such that pyruvate formate lyase activity is reduced or eliminated in said strain.

3. The isolated *E. asburiae* stain according to claim 1, wherein said *E. asburiae* stain is selected from *E. asburiae* JDR-1, E1, and L1.

4. A composition comprising a methylglucuronoxylose (MeGAX) containing acid hydrolyzed lignocellulosic hydrolysate and an *E. asburiae* strain according to claim 1.

5. A composition comprising culture medium and an *E. asburiae* strain according to claim 1.

6. A process for fermenting biomass comprising inoculating a culture medium comprising biomass with a *E. asburiae* stain according to claim 1 and fermenting said biomass containing culture medium and, optionally, recovering fermentation product from the substrate.

7. The process according to claim 6, wherein said culture medium contains methylglucuronoxylose (MeGAX).

8. The process according to claim 6, wherein said culture medium comprises an acid hydrolyzed lignocellulosic hydrolysate.

9. A process for fermenting MeGAX comprising:
   (a) forming a substrate from biomass materials;
   (b) subjecting the substrate to acid hydrolysis;

(c) inoculating the acid hydrolyzed substrate with the *Enterobacter asburiae* strain of claim 1 and fermenting MeGAX under conditions favorable for cell viability and conversion of MEGAX to a fermentation product; and (d) optionally, recovering said fermentation product.

10. The process of claim 9, wherein the biomass materials contain hemicellulose.

11. The process of claim 9, wherein the acid hydrolysis is dilute acid hydrolysis.

* * * * *

UNITED STATES PATENT AND TRADEMARK OFFICE
CERTIFICATE OF CORRECTION

PATENT NO. : 8,993,287 B2
APPLICATION NO. : 13/122985
DATED : March 31, 2015
INVENTOR(S) : James Faulker Preston It is certified that error appears in the above-identified patent and that said Letters Patent is hereby corrected as shown below:

In the Specification

Column 1,
Line 22, "DE FC36-990010476," should read --DE FC36-99GO10476,--.

Column 8,
Line 63, "fh.j," should read --f.h.j,--.

Column 9,
Line 13, "e.fh.k," should read --e.f.h.k,--.
Line 19, "e.j.k.m, e.k.l.m," should read --e.j.k.m, e.j.l.m, e.k.l.m,--.
Line 23, "fi.k.m, f.j.k.l," should read --f.i.k.m, f.i.l.m, f.j.k.l,--.
Line 27, "h.j.k.m, h.k.l.m," should read --h.j.k.m, h.j.l.m, h.k.l.m,--.
Line 32, "d.c.g.h.l," should read --d.e.g.h.l,--.
Line 43, "d.g.b.i.l," should read --d.g.h.i.l,--.
Line 46, "d.g.k.l.m, d.h.i.j.l," should read --d.g.k.l.m, d.h.i.j.k, d.h.i.j.l,--.
Line 57, "e.g.j.k.m, e.g.k.l.m," should read --e.g.j.k.m, e.g.j.l.m, e.g.k.l.m,--.
Line 61, "f.g.h.l.m, f.g.i.j.l," should read --f.g.h.l.m, f.g.i.j.k, f.g.i.j.l,--.
Line 65, "fi.k.l.m," should read --f.i.k.l.m,--.

Column 10,
Line 7, "d.e.fj.k.l," should read --d.e.f.j.k.l,--.
Line 8, "d.e.fk.l.m," should read --d.e.f.k.l.m,--.
Line 36, "e.gj.k.l.m," should read --e.g.j.k.l.m,--.
Line 47, "d.e.f.gj.l.m," should read --d.e.f.g.j.l.m,--.
Line 55, "d.c.h.i.j.l.m, d.e.h.i.k.l.m, d.c.h.j.k.l.m," should read
    --d.e.h.i.j.l.m, d.e.h.i.k.l.m, d.e.h.j.k.l.m--.
Line 59, "d.f.gj.k.l.m," should read --d.f.g.j.k.l.m,--.
Line 66, "e.f.gj.k.l.m," should read --e.f.g.j.k.l.m,--.

Signed and Sealed this
Twenty-seventh Day of October, 2015

Michelle K. Lee
*Director of the United States Patent and Trademark Office*

CERTIFICATE OF CORRECTION (continued)
U.S. Pat. No. 8,993,287 B2

Column 11,
Line 2, "e.g.ij.k.l.m," should read --e.g.i.j.k.l.m,--.
Line 51, "d.g.h, e.f.h," should read --d.g.h, e.f.g, e.f.h,--.
Line 57, "b.c.fg," should read --b.c.f.g,--.

Column 12,
Line 7, "b.c.d.e.g." should read --b.c.d.e.g.h,--.
Line 23, "in Ingrain" should read --in Ingram--.
Line 37, "h&c;" should read --b&c;--.
Line 65, "a; h;" should read --a; b;--.

Column 13,
Line 7, "a&c&d&e&f&b&c" should read --a&c&d&e&f; b&c--.
Lines 14-15, "($F_1F_0$)HtATP" should read --($F_1F_0$)$H^+$-ATP--.

Column 14,
Line 8, "a&b&c&c&f;" should read --a&b&c&e&f;--.

Column 17,
Line 24, "foi mate" should read --formate--.

Column 20,
Line 52, "containing MeGAX" should read --containing $MeGAX_n$--.
Line 66, "MeGAX" should read --$MeGAX_n$--.

Column 21,
Line 18, "McGAX" should read --MeGAX--.

Column 24,
Lines 26-27, "(1 mmol/min)" should read --(1 μmol/min)--.

Column 25,
Line 59, "3.6 mmol" should read --3.6 μmol--.

Column 26,
Line 25, "5 g NaCl)" should read --5 g $l^{-1}$ NaCl)--.
Line 28, "(10 mg and" should read --(10 mg $l^{-1}$ and--.